US012338267B2

(12) United States Patent
Church et al.

(10) Patent No.: US 12,338,267 B2
(45) Date of Patent: Jun. 24, 2025

(54) VIRAL VECTORS EXHIBITING IMPROVED GENE DELIVERY PROPERTIES

(71) Applicant: PRESIDENT AND FELLOWS OF HARVARD COLLEGE, Cambridge, MA (US)

(72) Inventors: George M. Church, Brookline, MA (US); Eric Kelsic, Cambridge, MA (US); Pierce Ogden, Cambridge, MA (US); Sam Sinai, Cambridge, MA (US)

(73) Assignee: PRESIDENT AND FELLOWS OF HARVARD COLLEGE

( * ) Notice: Subject to any disclaimer, the term of this patent is extended or adjusted under 35 U.S.C. 154(b) by 744 days.

(21) Appl. No.: 17/055,318

(22) PCT Filed: May 8, 2019

(86) PCT No.: PCT/US2019/031307
§ 371 (c)(1),
(2) Date: Nov. 13, 2020

(87) PCT Pub. No.: WO2019/221992
PCT Pub. Date: Nov. 21, 2019

(65) Prior Publication Data
US 2021/0230229 A1 Jul. 29, 2021

Related U.S. Application Data

(60) Provisional application No. 62/671,949, filed on May 15, 2018.

(51) Int. Cl.
*C07K 14/005* (2006.01)
*C12N 7/00* (2006.01)
*C12N 15/86* (2006.01)

(52) U.S. Cl.
CPC .............. *C07K 14/005* (2013.01); *C12N 7/00* (2013.01); *C12N 15/86* (2013.01); *C12N 2750/14122* (2013.01); *C12N 2750/14143* (2013.01); *C12N 2750/14145* (2013.01)

(58) Field of Classification Search
None
See application file for complete search history.

(56) References Cited

U.S. PATENT DOCUMENTS

| | | | |
|---|---|---|---|
| 6,156,303 A | 12/2000 | Russell et al. | |
| 2009/0215879 A1 | 8/2009 | Diprimio et al. | |
| 2014/0050701 A1* | 2/2014 | Zhong ................ | C12N 15/8645 435/456 |
| 2014/0341852 A1 | 11/2014 | Srivastava et al. | |
| 2017/0096683 A1 | 4/2017 | Scaria et al. | |

FOREIGN PATENT DOCUMENTS

| | | |
|---|---|---|
| WO | 2001068888 A2 | 9/2001 |
| WO | 2002053703 A2 | 7/2002 |
| WO | 2003052051 A2 | 6/2003 |
| WO | 2004111248 A2 | 12/2004 |
| WO | 2005005610 A2 | 1/2005 |
| WO | 2005033321 A2 | 4/2005 |
| WO | 2008124724 A1 | 10/2008 |
| WO | 2013170078 A1 | 11/2013 |
| WO | 2013173512 A1 | 11/2013 |
| WO | 2015/121501 A1 | 2/2015 |
| WO | 2017106236 A1 | 12/2016 |
| WO | 2017147477 A1 | 2/2017 |

OTHER PUBLICATIONS

Wu P, Xiao W, Conlon T, Hughes J, Agbandje-McKenna M, Ferkol T, Flotte T, Muzyczka N. Mutational analysis of the adeno-associated virus type 2 (AAV2) capsid gene and construction of AAV2 vectors with altered tropism. J Virol. Sep. 2000;74(18):8635-47. doi: 10.1128/jvi.74.18.8635-8647.2000. PMID: 10954565.*

Wu P, Xiao W, Conlon T, Hughes J, Agbandje-McKenna M, Ferkol T, Flotte T, Muzyczka N. Mutational analysis of the adeno-associated virus type 2 (AAV2) capsid gene and construction of AAV2 vectors with altered tropism. J Virol. Sep. 2000;74(18):8635-47. PMID: 10954565.. (Year: 2000).*

Wu et al. "Mutational analysis of the adeno-associated virus type 2 (AAV2) capsid gene and construction of AAV2 vectors with altered tropism." Journal of Virology 74(18): 8635-8647 (2000).

Aslanidi et al. "Optimization of the capsid of recombinant adeno-associated virus 2 (AAV2) vectors: the final threshold?." PloS one 8.3 (2013): e59142.

Perabo et al. "In vitro selection of viral vectors with modified tropism: the adeno-associated virus display." Molecular therapy 8.1 (2003): 151-157.

Wooley et al. "A directed evolution approach to select for novel Adeno-associated virus capsids on an HIV-1 producer T cell line." Journal of virological methods 250 (2017): 47-54.

De Silva et al. "Single residue AAV capsid mutation improves transduction of photoreceptors in the Abca4-/- mouse and bipolar cells in the rd1 mouse and human retina ex vivo." Gene Therapy 23(11): 767-774 (2016).

Buning et al. "Capsid modifications for targeting and improving the efficacy of AAV vectors." Molecular therapy Methods & clinical development 12: 248-265 (2019).

Gao et al. "Clades of Adeno-associated viruses are widely disseminated in human tissues." Journal of virology 78.12: 6381-6388 (2004).

(Continued)

*Primary Examiner* — Benjamin P Blumel
*Assistant Examiner* — Jeffrey Mark Sifford
(74) *Attorney, Agent, or Firm* — NIXON PEABODY LLP; David S. Resnick; Jeanne N. Jodoin

(57) ABSTRACT

The technology described herein provides viral capsid polypeptides bearing mutations that alters tissue tropism of a virus comprising the viral capsid polypeptide. In various embodiments, tissue tropisim to the heart, kidney, liver, lung, spleen, or blood is altered.

16 Claims, 6 Drawing Sheets

Specification includes a Sequence Listing.

(56) References Cited

OTHER PUBLICATIONS

Gao. “Adeno-associated virus isolate hu. 63 capsid protein VP1 (cap gene, complete cds. ” Retrieved from NCBI Database, accession No. AY530624 (2004).
Kanaan et al. “Rationally engineered AAV capsids improve transduction and volumetric spread in the CNS.” Molecular Therapy-Nucleic Acids 8: 184-197 (2017).
Yu et al. “A muscle-targeting peptide displayed on AAV2 improves muscle tropism on systemic delivery.” Gene therapy 16.8: 953-962 (2009).
Tseng et al. “Mapping the AAV capsid host antibody response toward the development of second generation gene delivery vectors.” Frontiers in immunology 5: 9 (2014).
UNIPROT. Accession No. A0A513ZUC6_9VIRU. Retrieved from the Internet at <https://www.uniprot.org/uniprotkb/A0A513ZUC6/entry> (2018).

* cited by examiner

SEQUENCE LISTING

```
<160> NUMBER OF SEQ ID NOS: 20

<210> SEQ ID NO 1
<211> LENGTH: 735
<212> TYPE: PRT
<213> ORGANISM: Adeno-associated virus 2

<400> SEQUENCE: 1

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
```

-continued

```
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735
```

<210> SEQ ID NO 2
<211> LENGTH: 161
<212> TYPE: PRT
<213> ORGANISM: Adeno-associated virus 2

<400> SEQUENCE: 2

```
Gln Tyr Leu Tyr Tyr Leu Ser Arg Thr Asn Thr Pro Ser Gly Thr Thr
1               5                   10                  15

Thr Gln Ser Arg Leu Gln Phe Ser Gln Ala Gly Ala Ser Asp Ile Arg
            20                  25                  30

Asp Gln Ser Arg Asn Trp Leu Pro Gly Pro Cys Tyr Arg Gln Gln Arg
        35                  40                  45

Val Ser Lys Thr Ser Ala Asp Asn Asn Asn Ser Glu Tyr Ser Trp Thr
    50                  55                  60

Gly Ala Thr Lys Tyr His Leu Asn Gly Arg Asp Ser Leu Val Asn Pro
65                  70                  75                  80

Gly Pro Ala Met Ala Ser His Lys Asp Asp Glu Glu Lys Phe Phe Pro
                85                  90                  95

Gln Ser Gly Val Leu Ile Phe Gly Lys Gln Gly Ser Glu Lys Thr Asn
            100                 105                 110

Val Asp Ile Glu Lys Val Met Ile Thr Asp Glu Glu Glu Ile Arg Thr
        115                 120                 125

Thr Asn Pro Val Ala Thr Glu Gln Tyr Gly Ser Val Ser Thr Asn Leu
    130                 135                 140

Gln Arg Gly Asn Arg Gln Ala Ala Thr Ala Asp Val Asn Thr Gln Gly
145                 150                 155                 160

Val
```

<210> SEQ ID NO 3
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 3

```
Asp Glu Glu Glu Ile Ala Thr Thr Asn Pro Val Ala Thr Glu Gln Tyr
1               5                   10                  15

Gly Asp Val Ser Glu Asn Leu Met His Phe Gln Asn
            20                  25
```

<210> SEQ ID NO 4
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 4

```
Asp Glu Glu Glu Ile Arg Gln Thr Asn Pro Val Ala Thr Glu Gly Tyr
1               5                   10                  15

Gly Glu Val Ser Thr Asn Leu Met His Gly Asn Lys
            20                  25
```

<210> SEQ ID NO 5
<211> LENGTH: 30
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 5

Asp Glu Glu Glu Ile Arg Thr Thr Asn Pro Val Ala Thr Glu Gln Tyr
1 5 10 15

Gly Ile Val Asn Ser Thr Thr Asn Leu Asn Glu Gly Asn Arg
20 25 30

<210> SEQ ID NO 6
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Asp Glu Glu Glu Ile Arg Thr Thr Asn Pro Val Ala Thr Glu Cys Tyr
1 5 10 15

Gly Ser Val Ser Thr Asp Leu Gln Ser Gly Asn Leu
20 25

<210> SEQ ID NO 7
<211> LENGTH: 31
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

Asp Glu Asn Glu Ile Arg Thr Thr Asn Pro Val Ala Thr Glu Ile Tyr
1 5 10 15

Gly Ser Val Ser Thr Glu Asn Leu Gln Asn Asn Gly Asp Asn Arg
20 25 30

<210> SEQ ID NO 8
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

Asp Glu Glu Glu Ile Arg Thr Thr Asn Pro Val Ala Thr Glu Gln Tyr
1 5 10 15

Gly Ser Val Ser Glu Thr Asn Pro Leu Val Gln Asn Gly Asp Asp Arg
20 25 30

<210> SEQ ID NO 9
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

Asp Glu Glu Glu Ile Arg Thr Thr Asn Pro Val Ala Thr Glu Gln Tyr
1 5 10 15

Gly Asp Val Ser Glu Asn Leu Met His Phe Gln Asn 20 25

<210> SEQ ID NO 10
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

Asp Glu Glu Glu Ile Arg Thr Thr Asn Pro Val Ala Thr Glu Gln Tyr
1 5 10 15

Gly Val Val Ser Asp Asn Leu Gln Arg Gly Asn Arg
20 25

<210> SEQ ID NO 11
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Asp Glu Cys Glu Ile Arg Thr Thr Asn Pro Val Ala Thr Glu Gln Tyr
1 5 10 15

Gly Ser Val Gly Glu Asn Leu Gln Arg Gly Asn Arg
20 25

<210> SEQ ID NO 12
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

Asp Glu Glu Glu Ile Arg Thr Thr Asn Pro Val Ala Thr Glu Gln Tyr
1 5 10 15

Gly Val Val Ser Glu Asn Leu Gln Arg Gly Asn Arg
20 25

<210> SEQ ID NO 13
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

Asp Glu Ser Glu Ile Thr Thr Thr Asn Pro Val Ala Thr Glu Gln Tyr
1 5 10 15

Gly Trp Val Ser Thr Asn Gln Gln Arg Gly Asn Arg
20 25

<210> SEQ ID NO 14
<211> LENGTH: 28
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 14

His Glu Leu Glu Ile Ala Thr Thr Asn Pro Val Ala Thr Glu Gln Tyr
1               5                   10                  15

Gly Ser Ala Ser Thr Asn Ile Gln Arg Gly Asn Arg
            20                  25


<210> SEQ ID NO 15
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Glu Glu Glu Ile Ala Thr Thr Asn Pro Val Ala Thr Glu Gln Tyr
1               5                   10                  15

Gly Gly Val Ser Thr Asn Leu Gln Arg Gly Asn Arg
            20                  25


<210> SEQ ID NO 16
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Glu Glu Glu Ile Val Thr Thr Asn Pro Val Ala Thr Glu Gln Tyr
1               5                   10                  15

Gly Asn Val Ser Thr Asn Leu Gln Arg Gly Asn Arg
            20                  25


<210> SEQ ID NO 17
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Glu Asp Glu Ile Ser Thr Thr Asn Pro Val Ala Thr Glu Gln Tyr
1               5                   10                  15

Gly Ser Cys Ser Thr Asn Leu Gln Arg Gly Asn Arg
            20                  25


<210> SEQ ID NO 18
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Glu Glu Glu Ile Arg Thr Thr Asn Pro Val Ala Thr Glu Gln Tyr
1               5                   10                  15

Gly Ser Val Ser Thr Asn Leu Gln Arg Gly Asp Arg
            20                  25


<210> SEQ ID NO 19
<211> LENGTH: 28
```

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asn Glu Glu Glu Ile Arg Thr Thr Asn Pro Cys Ala Thr Glu Val Tyr
1               5                   10                  15

Gly Ser Val Ser Thr Asn Leu Gln Arg Gly Asn Arg
            20                  25


<210> SEQ ID NO 20
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Glu Gln Glu Ile Val Thr Thr Asn Pro Val Ala Thr Glu Val Tyr
1               5                   10                  15

Gly Thr Val Ser Thr Asn Leu Gln Arg Gly Asn Arg
            20                  25
```

VIRAL VECTORS EXHIBITING IMPROVED GENE DELIVERY PROPERTIES

CROSS-REFERENCE TO RELATED APPLICATION

This application is a 35 U.S.C. § 371 National Phase Entry Application of International Application No. PCT/US19/31307 filed May 8, 2019, which designates the U.S. and claims benefit under 35 U.S.C. § 119(e) of the U.S. Provisional Application No. 62/671,949 filed May 15, 2018, the contents of which is incorporated herein by reference in their entireties.

GOVERNMENT SUPPORT

This invention was made with government support under HG008525 and HG005550 awarded by National Institutes of Health (NIH). The government has certain rights in this invention.

SEQUENCE LISTING

The instant application contains a Sequence Listing which has been submitted electronically in ASCII format and is hereby incorporated by reference in its entirety. Said ASCII copy, created on May 31, 2019, is named 002806-092110WOPT_SL.txt and is 15,134 bytes in size.

TECHNICAL FIELD OF THE INVENTION

This invention is related to viral vectors with modified tropism.

BACKGROUND OF THE INVENTION

Adeno-associated virus (AAV) is an attractive agent for use as gene delivery vector. Its simple structure also makes it an attractive target for genetic improvement programs. Nonetheless, there is a continuing need in the art to improve delivery of DNA using AAV and other viral vectors. In particular, there is a need in the art for viral vectors with modified tissue or cell tropism.

SUMMARY OF THE INVENTION

Described herein are viral vectors with modified tropism. Such vectors provide an improvement in the degree of tissue targeting attainable with such vectors. In particular, viral vectors with capsid polypeptide mutations that modify tropism of the viral particles relative to particles with wild-type capsid polypeptide are described. Through systematic mutation of viral capsid polypeptides, specific amino acid residues and amino acid regions have been identified that when mutated increase or decrease tropism of the virus for certain tissue or cell types. This provides the ability to increase the targeting of a given tissue or cell type by a viral vector, or, conversely, to decrease the targeting of a given tissue or cell type by a viral vector depending upon the site-specific mutation(s) introduced to the capsid polypeptide. Indeed, it has been found herein that not only can one improve the tropism of a viral vector by incorporating amino acid changes that increase tropism for a desired tissue, but nucleic acid delivery can also be improved to a given tissue or cell type by reducing the efficiency with which a viral vector infects tissues or cells other than the desired tissue or cell. Mutations that achieve both of these effects, and their use to improve delivery to desired or targeted tissues or cell types are described herein. Further, it has surprisingly been found that one can combine, within a single viral capsid polypeptide, mutations that improve tropism for a desired or targeted tissue or cell type with mutations that reduce tropism for a non-desired tissue or cell type, and thereby further improve targeting efficiency of the vector.

One aspect of the technology described herein provides a viral capsid polypeptide bearing a mutation relative to SEQ ID NO: 1 (WT AAV2) that alters tissue tropism of a virus comprising the viral capsid polypeptide, wherein the mutation is selected from the mutations in any one of Tables 1-7.

In one embodiment of any aspect, the tissue is heart, kidney, liver, lung, spleen, or blood.

In one embodiment of any aspect, the tropism to the tissue is increased. In one embodiment of any aspect, the tropism to the tissue is decreased.

Another aspect of the technology described herein provides a viral capsid polypeptide bearing a mutation that corresponds to a mutation of the polypeptide of SEQ ID NO: 1, the mutation selected for the group consisting of the mutations in Tables 1-9 relative to SEQ ID NO: 1.

Yet another aspect of the technology described herein provides a viral capsid polypeptide comprising a region corresponding to the amino acid sequence of SEQ ID NO: 2, wherein the region corresponding to the amino acid sequence of SEQ ID NO: 2 comprises a mutation relative to SEQ ID NO: 2 that alters tissue tropism of a virus comprising the viral capsid polypeptide, wherein the mutation is selected from the mutations in any one of Tables 10-15.

Another aspect of the technology described herein provides a nucleic acid encoding any of the the viral capsid polypeptides described herein.

Another aspect of the technology described herein provides a viral particle comprising any of the the viral capsid polypeptides described herein.

Another aspect of the technology described herein provides a method of delivering a nucleic acid to a cell, the method comprising; contacting the cell with a viral particle comprising any of the the viral capsid polypeptides described herein Another aspect of the technology described herein provides a method of delivering a nucleic acid to a blood cell, the method comprising; contacting a blood cell with a viral particle comprising a viral capsid polypetide comprising a mutation of Table 1.

Another aspect of the technology described herein provides a method of delivering a nucleic acid to a heart cell, the method comprising; contacting a heart cell with a viral particle comprising a viral capsid polypetide comprising a mutation of Table 2

Another aspect of the technology described herein provides a method of delivering a nucleic acid to a kidney cell, the method comprising; contacting a kidney cell with a viral particle comprising a viral capsid polypetide comprising a mutation of Table 3.

Another aspect of the technology described herein provides a method of delivering a nucleic acid to a liver cell, the method comprising; contacting a liver cell with a viral particle comprising a viral capsid polypetide comprising a mutation of Table 4.

Another aspect of the technology described herein provides a method of delivering a nucleic acid to a lung cell, the method comprising; contacting a lung cell with a viral particle comprising a viral capsid polypetide comprising a mutation of Table 5

Another aspect of the technology described herein provides a method of delivering a nucleic acid to a spleen cell, the method comprising; contacting a spleen cell with a viral particle comprising a viral capsid polypetide comprising a mutation of Table 6.

In one embodiment of any aspect, the delivering is at least 1.1-fold more efficient as compared to a wild-type viral capsid polypeptide.

Another aspect of the technology described herein provides a method of reducing tissue tropism of a virus comprising a viral capsid polypeptide corresponding to the viral capsid polypeptide of SEQ ID NO: 1, the method comprising introducing a mutation set out in any of Tables 7-9 (deenrichment Tables).

Another aspect of the technology described herein provides a method of increasing delivery of a nucleic acid to a cell of a kidney, heart, or lung, the method comprising; contacting a cell of a kidney, heart, or lung with a viral particle comprising a viral capsid polypetide comprising a mutation that reduces delivery of a nucleic acid to a cell of a liver, blood, or spleen.

In one embodiment of any aspect, the mutation that reduces delivery of a nucleic acid to a cell of a liver, blood, or spleen is selected from any of Tables 7-9.

Another aspect of the technology described herein provides a method of delivering a nucleic acid to a lung cell, the method comprising; contacting a lung cell with a viral particle comprising a viral capsid polypetide comprising a mutation of Table 5 and a mutation selected from any of Tables 7-9.

Another aspect of the technology described herein provides a method of delivering a nucleic acid to a heart cell, the method comprising; contacting a heart cell with a viral particle comprising a viral capsid polypetide comprising a mutation of Table 2 and a mutation selected from any of Tables 7-9.

Another aspect of the technology described herein provides a method of delivering a nucleic acid to a kidney cell, the method comprising; contacting a kidney cell with a viral particle comprising a viral capsid polypetide comprising a mutation of Table 3 and a mutation selected from any of Tables 7-9.

Another aspect of the technology described herein provides an AAV2 capsid polypeptide comprising a mutation in the region of amino acids selected the group consisting of: 440-460 of SEQ ID NO: 1, 475-505 of SEQ ID NO: 1, 518-532 of SEQ ID NO: 1, and 560-590 of SEQ ID NO: 1 that alters tissue tropism of a virus comprising the viral capsid polypeptide.

Another aspect of the technology described herein provides an AAV2 capsid polypeptide comprising a mutation in the region of amino acids 561-588 of SEQ ID NO: 1 that increases tissue tropism of a virus to the kidney, wherein the mutated region of amino acid 561-588 of SEQ ID NO: 1 has a sequence selected from the group consisting of:

(SEQ ID NO: 3)
DEEEIATTNPVATEQYGDVSENLMHFQN;

(SEQ ID NO: 4)
DEEEIRQTNPVATEGYGEVSTNLMHGNK;

(SEQ ID NO: 5)
DEEEIRTTNPVATEQYGIVnStTNLNEGNR;

(SEQ ID NO: 6)
DEEEIRTTNPVATECYGSVSTDLQSGNL;

-continued (SEQ ID NO: 7)
DENEIRTTNPVATEIYGSVSTeNLQNnGdNR;

(SEQ ID NO: 8)
DEEEIRTTNPVATEQYGSVSeTNpLvQNGdDR;

(SEQ ID NO: 9)
DEEEIRTTNPVATEQYGDVSENLMHFQN.

Another aspect of the technology described herein provides an AAV2 capsid polypeptide comprising a mutation in the region of amino acids 561-588 of SEQ ID NO: 1 that increases tissue tropism of a virus to the liver, wherein the mutated region of amino acid 561-588 of SEQ ID NO: 1 has a sequence selected from the group consisting of:

(SEQ ID NO: 10)
DEEEIRTTNPVATEQYGVVSDNLQRGNR;

(SEQ ID NO: 11)
DECEIRTTNPVATEQYGSVGENLQRGNR;

(SEQ ID NO: 12)
DEEEIRTTNPVATEQYGVVSENLQRGNR;

(SEQ ID NO: 13)
DESEITTTNPVATEQYGWVSTNQQRGNR;

(SEQ ID NO: 14)
HELEIATTNPVATEQYGSASTNIQRGNR;

(SEQ ID NO: 15)
DEEEIATTNPVATEQYGGVSTNLQRGNR.

Another aspect of the technology described herein provides an AAV2 capsid polypeptide comprising a mutation in the region of amino acids 561-588 of SEQ ID NO: 1 that increases tissue tropism of a virus to the lung, wherein the mutated region of amino acid 561-588 of SEQ ID NO: 1 has a sequence selected from the group consisting of:

(SEQ ID NO: 16)
DEEEIVTTNPVATEQYGNVSTNLQRGNR;

(SEQ ID NO: 17)
DEDEISTTNPVATEQYGSCSTNLQRGNR;

(SEQ ID NO: 18)
QEEEIRTTNPVATEQYGSVSTNLQRGDR;

(SEQ ID NO: 19)
NEEEIRTTNPCATEVYGSVSTNLQRGNR;

(SEQ ID NO: 20)
DEQEIVTTNPVATEVYGTVSTNLQRGNR.

Another aspect of the technology described herein provides a method of altering tropism of a virus comprising a capsid polypeptide corresponding to the polypeptide of SEQ ID NO: 1, the method comprising introducing a mutation in at least 2 regions selected from the group consisting of: amino acids 440-460 of SEQ ID NO: 1, amino acids 475-505 of SEQ ID NO: 1, amino acids 518-532 of SEQ ID NO: 1, and amino acids 560-590 of SEQ ID NO: 1.

Another aspect provides a viral capsid polypeptide bearing a mutation relative to SEQ ID NO: 1 (WT AAV2) that alters packaging efficiency of a virus comprising the viral capsid polypeptide, wherein the mutation is selected from the mutations in Table 16.

Definitions

As used herein the term "alters tropism" refers to a mutation or set of mutations that changes the efficiency with which a viral vector delivers a nucleic acid to a given tissue or cell type. The tropism of a virus or viral vector is generally defined by the structure of its outer surface that interacts with receptors or other cell surface determinants on target cells. For AAV vectors, among others, viral vector tropism is determined primarily by viral capsid polypeptides, and as described herein, the tropism of such vectors can be changed by changing the amino acid sequence of the viral capsid polypeptide. An amino acid change that changes the efficiency of viral vector delivery of a nucleic acid to a target cell or tissue type by at least 10% relative to a reference vector, often, but not necessarily relative to a wild-type vector, is an altered tropism. To be clear, an altered tropism can be an increase/enrichment by at least 10% (1.1×) or a decrease/de-enrichment by at least 10% (0.9×).

As used herein, the term "increases tropism: or "increased tropism" refers to an increase in efficiency of viral vector delivery of a nucleic acid to a target cell or tissue type by at least 0.1-fold or 10% relative to a reference vector. In various embodiments, the increase in efficiency of viral vector delivery of a nucleic acid to a target cell or tissue is at least 1.1× (i.e., 10% greater), 1.2× (i.e., 20% greater), at least 1.5× (i.e., 50% greater), at least 2.0× (i.e., doubled), at least 5.0× or at least 10.0× greater relative to the reference vector.

As used herein, the term "decreases tropism" or "decreased tropism" refers to a decrease in efficiency of viral vector delivery of a nucleic acid to a target cell or tissue type by at least 10% relative to a reference vector. In various embodiments, the efficiency of viral vector delivery of a nucleic acid to a target cell or tissue is at most 0.9× (10% lower, or 90% of reference), at most 0.8× (20% lower, or 80% of reference), at most 0.7× (30% lower, or 70% of reference), at most 0.5× (50% lower, or 50% of reference), at most 0.3× (70% lower, or 30% of reference), at most 0.2× (80% lower, or 20% of reference), at most 0.1× (90% lower, or 10% of reference) or lower relative to the reference vector.

As used herein, the term "corresponding to," when used in reference to an amino acid or polynucleotide sequence means that a given amino acid or polynucleotide sequence in one polypeptide or polynucleotide molecule has structural properties, functional properties, or both that are similar relative to an amino acid or polynucleotide sequence in a similar location in another polypeptide or polynucleotide molecule. Homologues of a given polypeptide in different species "correspond to" each other, as do regions or domains of homologous polypeptides from different species. Similarly, capsid polypeptides of different serotypes of viral vectors, including but not limited to adeno-associated virus (AAV) vectors, "correspond to" each other, as do regions of such polypeptides, defined, for example by alignment of their amino acid sequences. While other alignment parameters can be used to define such regions, for the avoidance of doubt, alignment can be performed using BLAST® (Basic Local Alignment Search Tool) using default parameters of version BLAST+ 2.8.0 released Mar. 28, 2018.

DETAILED DESCRIPTION OF THE INVENTION

Figure 1:
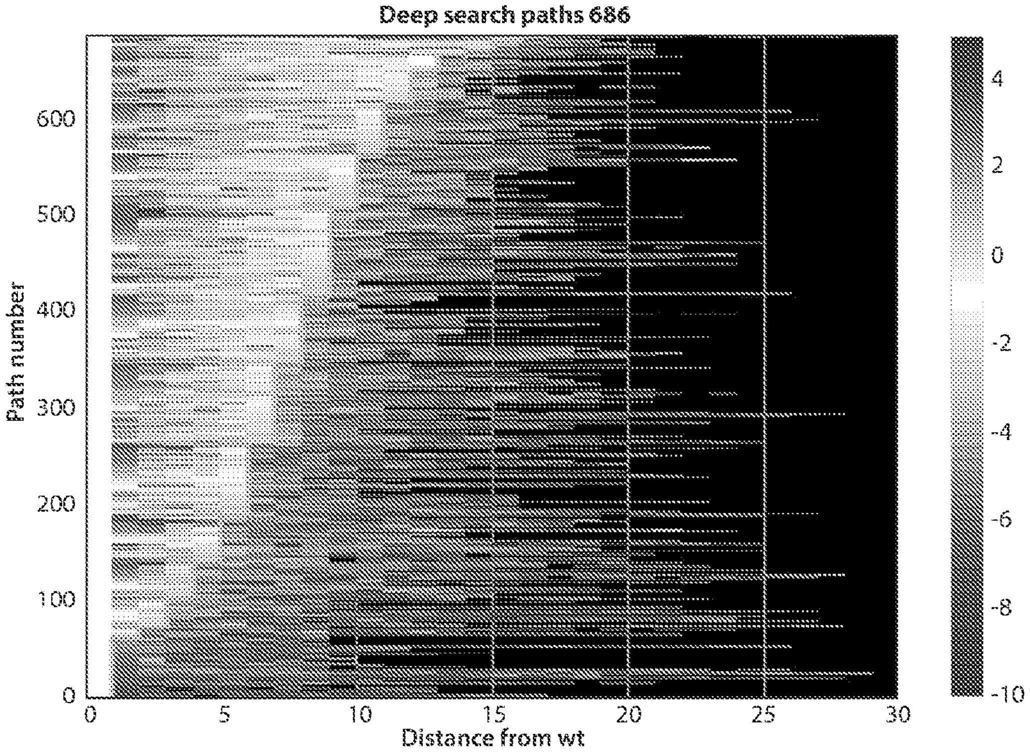
FIG. 1 shows a heat map of all path numbers searched versus that distance from wild-type (e.g., the number of mutations relative to wild-type). Beneficial mutations, neutral mutations, and deleterious mutations are shown. Most mutations are deleterious.
Figure 2:
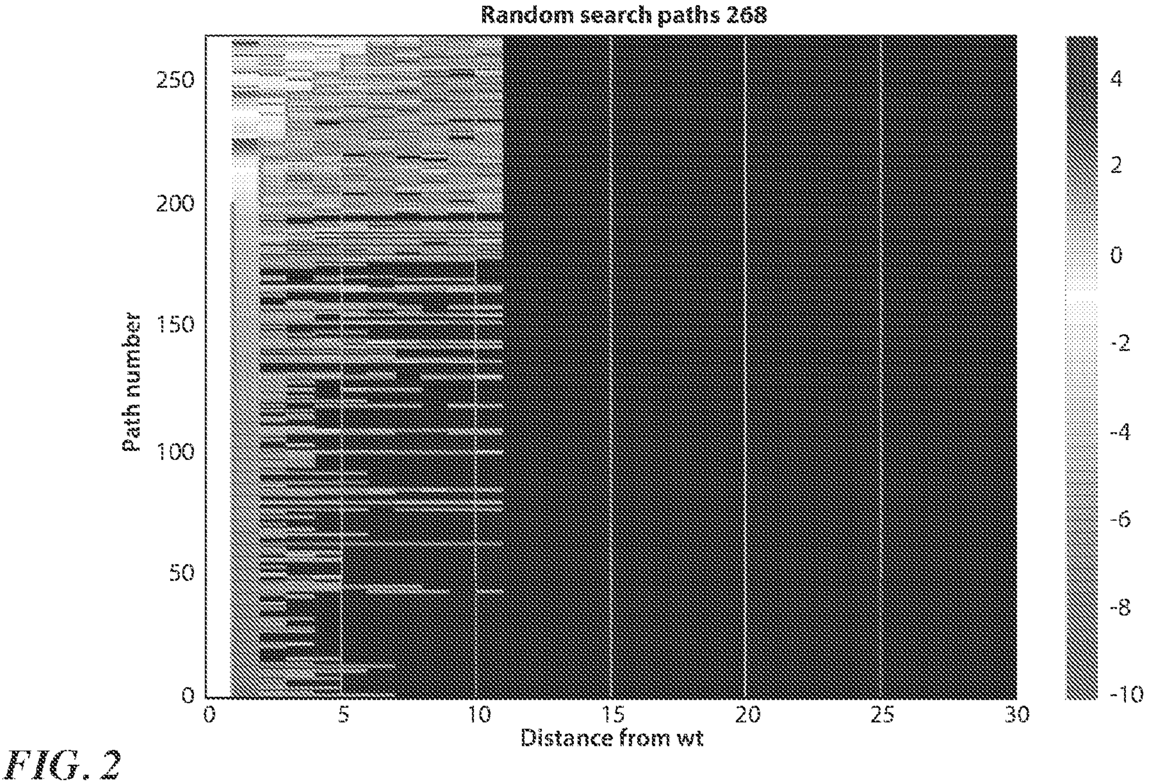
FIG. 2 shows a heat map of a subset of path numbers searched versus that distance from wild-type (e.g., the number of mutations relative to wild-type. Beneficial mutations, neutral mutations, and deleterious mutations are shown. Heat map highlights that longer paths quickly die off.

Described herein are viral vectors with modified tropism. Such vectors provide an improvement in the degree of tissue targeting attainable with such vectors. In particular, viral vectors with capsid polypeptide mutations that modify tropism of the viral particles relative to particles with wild-type capsid polypeptide are described. Through systematic mutation of viral capsid polypeptides, specific amino acid residues and amino acid regions have been identified that when mutated increase or decrease tropism of the virus for certain tissue or cell types. This provides the ability to increase the targeting of a given tissue or cell type by a viral vector, or, conversely, to decrease the targeting of a given tissue or cell type by a viral vector depending upon the site-specific mutation(s) introduced to the capsid polypeptide. Indeed, it has been found herein that not only can one improve the tropism of a viral vector by incorporating amino acid changes that increase tropism for a desired tissue, but nucleic acid delivery can also be improved to a given tissue or cell type by reducing the efficiency with which a viral vector infects tissues or cells other than the desired tissue or cell. Mutations that achieve both of these effects, and their use to improve delivery to desired or targeted tissues or cell types are described herein. Further, it has surprisingly been found that one can combine, within a single viral capsid polypeptide, mutations that improve tropism for a desired or targeted tissue or cell type with mutations that reduce tropism for a non-desired tissue or cell type, and thereby further improve targeting efficiency of the vector.

Viruses are typically tropic for certain types of cells and or tissues in the natural host. Changes in this tropism, either increased or decreased, may be determined by selection on a natural host cell or tissue or selection on a non-natural host cell or tissue. Indeed, experiments were performed to select for increased infectivity for the following tissues: blood, brain, heart, kidney, liver, lung, and spleen. Substitution, deletion or insertion mutations that increased the infectivity in these tissues were found. These determinations were also combined with the ability of the mutant plasmids to be packaged into virions.

As detailed below herein, particular mutations have been identified and assessed for effects on viral DNA packaging and viral infectivity of particular tissues. These particular mutations are in the capsid protein. Isolated and purified compositions comprising mutant capsid proteins and nucleic acids encoding them may be used for further viral improvement, for virus preparation and manufacture, and for safety and efficacy studies. Once a mutant protein sequence is identified as beneficial, any nucleic acid codon or codons that specify such protein sequence can be used. Mutations can be combined together in a single viral nucleic acid or a single viral protein sequence for improved properties. The following describes mutations to viral capsid polypeptides that permit viral genome packaging, yet modify viral vector tropism, either positively, negatively, or both when mutations are combined, relative to given tissues or cell types. Also described are methods of using mutated viral capsid polypeptides and viral vectors comprising them to introduce nucleic acids to desired tissue or cell types with improved selectivity for those tissue or cell types. The following provides a description of the various mutations and considerations for their use to generate viral vectors with improved properties.

Generating Variants and Viral Particles

A DNA library of AAV capsid variants was created. Initially each mutant capsid was generated with a single mutation. All possible single amino acid substitutions, insertions and deletions for AAV2 were generated. In a subsequent step, several mutations were combined within the capsid gene. Libraries of AAV2 capsid gene sequence variants were cloned into a plasmid containing the AAV Inverted Terminal Repeat regions (ITRs). The final ITR plasmids contained a cytomegalovirus (CMV) promoter upstream of the Cap gene.

AAV virus libraries were produced from the DNA libraries. The capsid library plasmids, AAV pHelper plasmids, and plasmids containing the AAV2 Rep gene were co-transfected into HEK-293 cells using PEI. Capsids were purified using standard techniques for cell lysis (freeze-thaw or addition of 5 M NaCl), treatment with benzonase to remove unpackaged genomes, and purification and concentration by iodixanol ultra-centrifugation In vivo packaging ability of viral capsid variants was measured. The number of viruses that were packaged ("virus") compared to the number of input viral genomes ("plasmid") were determined. Measuring the frequency of capsid (or other library component) mutants before and after selection reveals which mutations are beneficial and which are deleterious based on the particular selection method.

Evaluating Viral Tropism

To investigate viral tropism, virus libraries were injected into mice intravenously. Blood was collected 1 hour after injection and tissue samples were collected 1-2 weeks after injection. Viral DNA was extracted from bulk biological samples using standard techniques.

The frequencies of capsid variants in biological samples, the virus libraries and the DNA libraries were measured using high-throughput DNA sequencing. Mutant frequencies were normalized by dividing the number of reads matching each mutant by the number of reads matching the AAV2 WT sequence within each sample.

Selection values, indicating enrichment or de-enrichment within a particular sample, are calculated relative to an initial library. Selection values greater than 1 indicate enrichment relative to WT. Selection values less than 1 indicate de-enrichment relative to WT.

For packaging selection, the frequencies in the viral library were compared to those in the DNA library as a reference. Enrichment means that a mutant packaged more efficiently than the WT.

For tissue selection, the frequencies in tissue samples were compared to those in the viral library as a reference. Enrichment means that a mutant was delivered more efficiently than the WT to the specified tissue. De-enrichment means that a mutant was delivered less efficiently that WT to the specified tissue.

Viral Capsid Polypeptide

Viral tropism refers to the cell or tissue type(s) in a host that recruit and support the growth of a virus. Various factors impact the viral tropism, including the expression of cell surface receptors and/or ligands, transcription factor expression, and expression of tropogens (e.g., cell surface glycoproteins). One aspect of the invention provides a viral capsid polypeptide bearing a mutation relative to wild-type adeno-associated virus 2 (AAV2, e.g., SEQ ID NO: 1) that alters tissue tropism of a virus comprising the viral capsid polypeptide, wherein the mutation is selected from the mutations in any one of Tables 1-9. In one embodiment, the tissue is blood, heart, kidney, liver, lung, or spleen.

In one embodiment, the tropism is increased, e.g, the virus comprising the mutated viral capsid polypeptide more efficiently delivers nucleic acid to the target cell type as compared a virus comprising the wildtype viral capsid polypeptide. In one embodiment, tropism is at least 1.1-fold (e.g., 10% greater than reference level, or 110% of the level reference level) more efficient as compared to a wild-type viral capsid polypeptide. In one embodiment, the the delivery of a nucleic acid is at least 1.5-fold, at least 2-fold, at least 4-fold, at least 5-fold, at least 10-fold, or more, more efficient as compared a virus comprising the wildtype viral capsid polypeptide. One of ordinary skill in the art can measure the delivery efficiency of a viral particle comprising any of the viral capsid polypeptides described herein, e.g., using PCR-based assays on an isolated targeted cell or tissue type (e.g., blood, heart, kidney, liver, lung, or spleen) to assess if the nucleic acid is expressed in that targeted cell type. The expression of the nucleic acid delivered by a viral particle comprising either a viral capsid polypeptide as described herein or a wild-type viral capsid polyprotein can be compared to determine the change in expression as a measure of the efficiency of delivery.

In one embodiment, the tropism is decreased, e.g, the virus comprising the mutated viral capsid polypeptide less efficiently delivers nucleic acid to the target cell type as compared a virus comprising the wildtype viral capsid polypeptide. In one embodiment, the tropism is decreased by at least 10%. In other embodiments, the tropism is decreased by at least 20%, at least 30%, at least 40%, at least 50%, at least 60%, at least 70%, at least 80%, at least 90%, at least 99%, or more as compared to a virus comprising the wildtype viral capsid polypeptide. Methods for measuring tropism are described herein above.

The following describes single amino acid capsid alterations that increase the tropism of a virus (e.g., AAV2) for a given tissue or cell type, e.g., blood, heart, kidney, liver, lung, or spleen. In one embodiment, a single mutation described herein is introduced to the amino acid sequence of wild-type AAV2 capsid protein (e.g., SEQ ID NO: 1) to increase or decrease tissue or cell type tropism or a virus.

```
                                        (SEQ ID NO: 1)
MAADGYLPDWLEDTLSEGIRQWWKLKPGPPPPKPAERHKDDSRGLVLPG

YKYLGPENGLDKGEPVNEADAAALEHDKAYDRQLDSGDNPYLKYNHADA

EFQERLKEDTSFGGNLGRAVFQAKKRVLEPLGLVEEPVKTAPGKKRPVE

HSPVEPDSSSGTGKAGQQPARKRLNFGQTGDADSVPDPQPLGQPPAAPS

GLGTNTMATGSGAPMADNNEGADGVGNSSGNWHCDSTWMGDRVITTSTR

TWALPTYNNHLYKQISSQSGASNDNHYFGYSTPWGYFDENRFHCHFSPR

DWQRLINNNWGFRPKRLNFKLENIQVKEVTQNDGTTTIANNLTSTVQVF

TDSEYQLPYVLGSAHQGCLPPFPADVEMVPQYGYLTLNNGSQAVGRSSF

YCLEYFPSQMLRTGNNFTFSYTFEDVPFHSSYAHSQSLDRLMNPLIDQY

LYYLSRTNTPSGTTTQSRLQFSQAGASDIRDQSRNWLPGPCYRQQRVSK

TSADNNNSEYSWTGATKYHLNGRDSLVNPGPAMASHKDDEEKFFPQSGV
```

-continued

```
LIFGKQGSEKTNVDIEKVMITDEEEIRTTNPVATEQYGSVSTNLQRGNR

QAATADVNTQGVLPGMVWQDRDVYLQGPIWAKIPHTDGHFHPSPLMGGF

GLKHPPPQILIKNTPVPANPSTTESAAKFASFITQYSTGQVSVEIEWEL

QKENSKRWNPEIQYTSNYNKSVNVDFTVDTNGVYSEPRPIGTRYLTRNL
```

As used herein, “mutation” refers to any change in the amino acid sequence, e.g., a substitution, insertion, or deletion of at least one amino acid. For the mutations described herein, a substitution at a particular position is denoted by the wildtype amino acid followed by the position of the substituted amino acid followed by the identity of the substituted amino acid(s) in a parenthetical, e.g., Q101(A) means glutamine is substituted with alanine at position 101. If multiple amino acids can be substituted at a particular position, the parenthetical lists all possible single substitutions, e.g., P31(IKRT) means that proline at position 31 is substituted with any one of isoleucine, lysine, arginine, or threonine. To denote an insertion, the amino acid position contains a decimal followed by an amino acid(s); the amino acid(s) following the decimal are inserted following the position indicated, e.g, 28.5(AGVY) means any one of alanine, glycine, valine, or tyrosine is inserted immediately after amino acid 28 and immediately before amino acid 29. To denote a deletion of an amino acid, “(-)” follows the amino acid position, e.g., A35(-) means amino acid 35 (alanine) is deleted from the sequence.

The following provides mutations to the AAV2 capsid polypeptide of SEQ ID NO: 1 that provide tropism altered by the indicated degree for cells of the indicated tissues.

TABLE 1

Amino acid alterations conferring more efficient delivery to blood.

| Amino acid alteration | Fold increase of efficiency |
|---|---|
| D4(F), D13(HQ), Q21(FS), W22(F), W23(EGLTVY), 23.5(Y), L25(C), K26(N), 28.5(AGVY), P29(DEGSTVY), P31(IKRT), 32.5(F), K33(AFLPST), 33.5(IP), 34.5(EY), A35(-), E36(CDGV), 36.5(CW), R37(GV), 37.5(DHNW), H38(K), 38.5(DHQ), G49(W), V65(KT), K77(EG), D80(KW), R81(TY), Q82(AIL), L83(Q), D84(N), S85(FQR), G86(Q), N88(FH), K92(Q), H95(W), A98(Q), E99(T), Q101(A), E102(HIKT), K105(Y), E106(T), 107.5(F), T108(W), F110(QTW), G112(A), N113(Y), R116(AK), A117(C), Q120(DH), R124(AQ), V125(HITW), P128(G), L129(E), 129.5(P), L131(C), V132(D), 132.5(D), E134(N), 134.5(K), P135(-I), V136(AI), K137(E), 138.5(HKP), A139(FHWY), 139.5(IK), 141.5(FG), 144.5(P), P145(FG), E147(T), 147.5(Y), H148(-Q), S149(DFT), 151.5(I), E152(Y), 152.5(AV), S157(H), T159(H), A162(K), Q164(HRSW), Q165(I), P166(HNQ), 177.5(C), A179(P), 179.5(W), V182(L), D184(W), 188.5(CF), G189(CHQSY), 189.5(AEF), Q190(FNVY), 190.5(CE), P191(FH), 191.5(N), P192(NR), 192.5(F), A193(KQ), A194(-NQ), 194.5(EQW), P195(-), T202(WY), T205(CDF), A209(C), N214(D), G217(D), 237.5(N), A248(C), Q263(T), S264(G), Y272(F), R310(K), N312(E), T324(S), 324.5(R), D327(E), T344(EGHY), S346(Q), L380(V), S384(A), Q401(N), S412(A), 417.5(S), V418(C), L433(V), 445.5(D), S446(-), 446.5(DE), R447(-PWY), 447.5(DEHQ), T448(-DEH), 448.5(D), N449(H), T450(FS), 452.5(P), G453(V), T454(APQ), T455(GMS), T456(A), 456.5(A), 457.5(MT), Q464(R), 464.5(Y), S468(M), C482(MSW), Y483(W), R484(ILQV), 485.5(M), Q486(DE), R487(ACDEFGILMNPQSTVWY), 488.5(DE), S489(DE), 490.5(DE), T491(FN), 491.5(DE), A493(FS), 493.5(ENST), 494.5(E), N495(DEW), 495.5(DE), N496(DE), 496.5(DE), N497(AMP), 498.5(ST), 500.5(D), S501(D), 501.5(DE), 502.5(DE), 503.5(DE), G504(DE), 504.5(E), 505.5(E), K507(-EF), P521(I), M523(C), S525(T), 525.5(DE), K527(PQW), D528(Q), E531(DGMN), K532(ADEFGILMNPQSTVY), 532.5(DEMN), F533(DEY), 533.5(CDEGSV), 536.5(V), V539(C), V571(DE), Q575(A), Y576(M), 577.5(E), V579(VV), 579.5(CDEN), S580(ADE), 580.5(DEILMPY), T581(DSWY), 581.5(DEFILMPQV), N582(-ACDEPQ), 582.5(GP), L583(-DEGPT), 583.5(DEIPV), Q584(-DEFLNTY), 584.5(ADEIMVY), R585(-ADEFGHILMNPQSTVWY), 585.5(DE), G586(-DEP), 586.5(DEFHINVY), N587(-DE), 587.5(DEGPY), R588(-ACDEFGHILMNPQSTVWY), | 1.1-fold |

TABLE 1-continued

| Amino acid alterations conferring more efficient delivery to blood. | |
|---|---|
| Amino acid alteration | Fold increase of efficiency |
| 588.5(DEFQTY), Q589(DEFMNY), 589.5(DEGINS), A590(DEW), 590.5(DEFY), A591(EFPQSY), 591.5(CDEQWY), T592(FY), 592.5(DEQ), A593(GLMTVW), 593.5(CDEILY), 594.5(CDEP), 595.5(C), N596(S), T597(AS), V600(AILST), L601(L), G603(G), V605(C), D608(N), R609(R), V611(C), P616(M), H623(INY), T624(C), L639(C), H641(S), 1646(C), N656(AH), 657.5(Q), T660(H), S662(HWY), 662.5(I), A664(W), F666(M), A667(FR), K688(P), V708(WY), and N734(S) | |
| 445.5(D), S446(-), 446.5(DE), R447(-P), 447.5(DEHQ), T448(-DE), N449(H), T454(P), 464.5(Y), C482(M), R484(ILQV), 485.5(M), Q486(DE), R487(ACDEFGILMNPQSTVWY), 488.5(E), S489(DE), 490.5(DE), T491(N), N495(DEW), 495.5(DE), N496(DE), 496.5(DE), S501(D), 501.5(D), 502.5(DE), 503.5(DE), G504(DE), K507(-E), 525.5(D), E531(GMN), K532(ADEFGILMNPSTVY), 532.5(DEM), F533(DE), 533.5(CDEGSV), V571(DE), 577.5(E), V579(V), 579.5(CDE), S580(DE), 580.5(DEILMY), T581(W), 581.5(DEFILMPQV), N582(-ACDEP), 582.5(GP), L583(-DEPT), 583.5(DEIPV), Q584(-DEFLTY), 584.5(DEIV), R585(-ADEFGHILMNPQSTVWY), 585.5(DE), G586(-DE), 586.5(DEFHY), N587(-DE), 587.5(DEP), R588(-ACDEFGHILMNPQSTVWY), 588.5(DEFY), Q589(DEFY), 589.5(DEIN), A590(DEW), 590.5(DE), A591(PY), 591.5(CDEY), T592(FY), 592.5(DE), 593.5(CDE), 594.5(CDE), 595.5(C), N596(S), and A667(FR) | 1.5-fold |
| 445.5(D), S446(-), 446.5(DE), R447(-P), 447.5(EHQ), T448(D), T454(P), 464.5(Y), R484(ILQV), 485.5(M), Q486(DE), R487(ACDEFGILMNPQSTVWY), 488.5(E), S489(DE), 490.5(D), N495(DEW), 495.5(DE), N496(DE), 496.5(DE), S501(D), 501.5(D), 502.5(E), 503.5(DE), G504(DE), K507(-), K532(ADEGILMNPSTV), 532.5(DE), F533(DE), 533.5(CDEGSV), V571(DE), 577.5(E), 579.5(DE), S580(DE), 580.5(DEILMY), T581(W), 581.5(DEFILMPQV), N582(-DEP), 582.5(GP), L583(-DEP), 583.5(DEIPV), Q584(-DEFY), 584.5(DEIV), R585(-ADEFGHILMNPQSTVWY), 585.5(DE), G586(-DE), 586.5(DEY), N587(-DE), 587.5(DEP), R588(-ACDEFGHILMNPQSTVWY), 588.5(DE), Q589(DE), 589.5(DEIN), A590(DEW), 590.5(DE), A591(PY), 591.5(DE), T592(FY), 592.5(DE), 593.5(DE), and 594.5(CDE) | 2-fold |
| N496(DE), S501(D), G504(D), K532(DE), 581.5(DEIPV), N582(DE), 582.5(G), L583(-DE), 583.5(DEP), Q584(-DE), 584.5(DE), R585(-ADEFGHILMNPQSTVWY), 585.5(DE), G586(-D), 586.5(DE), N587(-DE), 587.5(DEP), R588(-ACDEFGHILMNPQSTVY), 588.5(DE), 589.5(DE), A590(DE), 590.5(D), 593.5(E), and 594.5(E) | 5-fold |
| R585(D) | 10-fold |

TABLE 3

| Amino acid alterations conferring more efficient delivery to kidney. | |
|---|---|
| Amino acid alteration | Fold increase of efficiency |
| D13(Q), E17(D), Q21(F), W23(G), L25(C), 28.5(Y), P29(D), P31(KRST), K33(ART), 34.5(AY), 35.5(E), E36(DGV), 36.5(S), R37(GK), 37.5(DHSW), H38(KN), 38.5(Q), E63(S), V65(K), A70(K), K77(KQ), A78(E), D80(W), R81(HTY), Q82(I), S85(FGQ), N88(V), K92(Q), E99(A), Q101(N), E102(T), R103(T), E106(W), F110(K), G112(AS), R116(IKQ), V118(AF), Q120(FH), R124(E), L126(DH), E127(L), L129(A), 129.5(P), G130(E), L131(Q), E134(P), 134.5(KPRSWY), P135(-), 135.5(V), V136(AR), 137.5(K), 138.5(PW), 140.5(PV), 141.5(A), 145.5(FY), V146(P), 146.5(E), 147.5(Y), H148(-EQ), S149(D), P150(F), 150.5(Y), V151(IN), 152.5(V), P153(P), A162(T), Q164(EL), Q165(I), D180(NW), S181(E), Q186(WY), L188(F), 188.5(Q), G189(DEQ), 189.5(AKN), Q190(FY), 190.5(EQT), P191(KPP), 191.5(F), P192(V), 192.5(EIK), A193(-), 194.5(DE), T200(Y), N201(HY), T205(D), G217(D), Q263(A), S264(G), R310(K), D327(E), T344(AHP), V387(M), R389(S), T410(Q), A425(S), 446.5(D), 447.5(HQ), N449(ACGS), T456(AG), 456.5(G), R459(HK), Q464(A), A467(GNP), S468(AG), D469(AEQST), I470(LMV), R471(K), C482(M), Q486(D), R487(P), S489(E), 490.5(N), T491(F), A493(FI), N495(E), 495.5(DE), N496(EHS), 496.5(D), N497(P), S498(M), Y500(M), S501(D), 501.5(D), G504(D), N518(S), H526(CS), K532(DER), 532.5(D), F533(Y), K544(ILTV), T550(G), K556(N), D561(Q), R566(AV), S578(TV), V579(V), S580(A), 580.5(IMY), 581.5(EFILMPQV), N582(-ACDEP), 582.5(GP), L583(-DEIP), 583.5(DEIPV), Q584(-EFY), 584.5(DEILV), R585(-DEINPQVW), 585.5(D), G586(-), 586.5(DEIY), N587(-D), 587.5(DEP), R588(-ACDEGHLNPQTV), 588.5(DE), Q589(MP), 589.5(DE), A590(DEPV), 590.5(DE), A591(PST), | 1.1-fold |

TABLE 3-continued

| Amino acid alterations conferring more efficient delivery to kidney. | |
|---|---|
| Amino acid alteration | Fold increase of efficiency |
| 591.5(C), A593(M), 593.5(CE), T597(ASW), Q598(L), V600(A), V611(C), H623(IY), H627(F), P630(M), L639(C), H641(NQS), S658(AP), T659(V), F666(M), and V708(WY) | |
| R389(S), D469(AQ), 1470(L), R471(K), 490.5(N), 495.5(DE), N496(EHS), S498(M), S501(D), K532(D), 580.5(I), 581.5(EILMPV), N582(-D), 582.5(GP), L583(DE), 583.5(DEIPV), Q584(-EFY), 584.5(IL), R585(-IP), G586(-), N587(-), 587.5(P), R588(-CDGV), 588.5(D), 589.5(DE), A591(P), 591.5(C), 593.5(C), T597(W), and V600(A) | 1.5-fold |
| R389(S), R471(K), K532(D), 581.5(IM), L583(DE), 583.5(D), 584.5(L), G586(-), N587(-), 587.5(P), R588(-), 591.5(C), and 593.5(C) | 2-fold |

TABLE 2

| Amino acid alterations conferring more efficient delivery to heart. | |
|---|---|
| Amino acid alteration | Fold increase of efficiency |
| E17(D), W23(GKRY), 23.5(Y), L25(C), P29(D), P31(INRT), K33(LP), 33.5(P), A35(E), 35.5(EKPQ), E36(DG), 36.5(PS), R37(K), 37.5(HSW), H38(K), 38.5(D), K39(Q), G49(W), A70(KW), K77(EKQ), R81(Y), Q82(I), S85(FQ), K92(Q), A98(Q), Q101(AN), R103(T), E106(W), T108(W), L114(F), R116(FIKQ), V118(AFV), A121(T), G130(EW), L131(C), E134(DNP), 134.5(KLS), P135(-), 135.5(V), V136(R), 136.5(A), 138.5(H), 140.5(PV), 141.5(GP), V146(G), H148(-Q), 148.5(V), P150(FN), 150.5(Y), V151(IN), 151.5(EI), E152(F), 152.5(VW), T159(K), K161(F), A162(KN), Q164(AEFW), N172(Y), 179.5(W), D180(NW), V182(I), D184(W), Q186(F), 188.5(T), G189(DEQY), 189.5(DEFIKV), Q190(-F), 190.5(EIQT), P191(H), 191.5(N), P192(G), 192.5(FK), A193(-), A194(-ENT), 194.5(EW), P195(-), T205(F), S243(C), I260(L), Q263(A), S264(G), S267(S), R310(K), D327(E), T344(EP), S346(Q), S356(N), Q359(D), S384(S), V387(M), R389(S), T414(V), V418(C), S422(G), L433(A), 1438(N), Y444(F), 448.5(S), N449(A), T450(M), S452(M), T454(LQ), 455.5(A), T456(AV), Q457(DLV), S458(AP), 458.5(Q), R459(FH), Q464(AI), A467(CGNPQ), S468(ADG), D469(AENQST), I470(LMV), R471(CKM), C482(M), Q486(N), R487(ACGIMQSTV), S489(AD), 490.5(N), T491(FLW), 492.5(M), A493(M), N496(DHSY), N497(PV), S498(FM), Y500(M), T506(S), V517(I), S525(AG), H526(CNST), E531(D), K532(ADEFGILMNQRST), I541(C), K544(CGTVY), Q545(E), K549(Q), N551(Y), V552(Q), K556(DNY), D561(Q), R566(ASV), T567(S), S578(TV), V579(V), S580(A), T581(WY), 581.5(IV), N582(DE), L583(DE), 584.5(EIV), R585(-ADFGHILMNQSTVWY), G586(DE), N587(DE), 587.5(D), R588(ACDEFHILMNQSTVY), 588.5(DE), Q589(M), A590(P), A591(ETY), 591.5(CDE), T592(F), 594.5(D), T597(ANSW), Q598(L), V600(AS), W606(F), V611(C), T624(C), H641(QS), L647(F), N656(A), P657(P), S658(P), T659(A), S662(FQ), A664(L), A667(N), Q687(K), V708(WY), N709(A), and N734(P) | 1.1-fold |
| 37.5(H), S264(G), D327(E), R389(S), D469(AQS), 1470(LM), R471(K), R487(A), S489(D), 490.5(N), T491(W), N496(D), S498(M), K532(ADEL), D561(Q), N582(DE), L583(E), 584.5(V), R585(-AGHIMNQSTVWY), N587(DE), R588(ADEFILMNQSTVY), 588.5(DE), Q589(M), 591.5(D), T597(W), and V600(A) | 1.5-fold |
| R471(K), K532(D), N582(D), L583(E), R585(Q), N587(DE), R588(MQTV), and 588.5(E) | 2-fold |

TABLE 4

| Amino acid alterations conferring more efficient delivery to liver. | |
|---|---|
| alterations conferring more Amino acid alteration | Fold increase of efficiency |
| E17(D), P31(Q), K33(HV), 35.5(KW), E36(D), 36.5(EY), R37(QT), 37.5(H), H38(K), A70(EG), K77(Q), A78(DE), D80(KW), R81(HY), Q82(A), L83(I), D84(N), S85(FGQ), N88(F), L91(Y), A98(Q), E99(AL), Q101(NT), E102(KT), R103(QW), K105(D), E106(A), 107.5(F), F110(QT), | 1.1-fold |

TABLE 4-continued

| Amino acid alterations conferring more efficient delivery to liver. | |
|---|---|
| alterations conferring more<br>Amino acid alteration | Fold increase of efficiency |
| V118(CFV), Q120(DN), R124(Q), V125(IT), L126(T), E127(S), L129(HP), 129.5(P), 133.5(T), E134(HRV), 134.5(S), P135(L), 139.5(IQ), P140(I), G141(P), K142(V), 145.5(A), H148(FP), 148.5(D), 149.5(D), 150.5(H), 151.5(K), E152(S), 152.5(A), P153(P), S157(Y), T159(KN), 163.5(Q), Q164(AF), 177.5(F), D178(C), A179(Q), G189(DFQS), 189.5(HISTVY), Q190(F), 190.5(EKLN), P191(GT), 191.5(DN), 192.5(A), A193(-), A194(N), 194.5(W), S196(A), T205(N), A212(E), A248(C), 1260(M), Q263(A), S264(G), Y275(W), Q325(T), D327(E), T329(H), T331(Q), T344(AHPY), S356(GN), M371(H), V387(M), R389(S), T414(Y), S423(S), L433(AC), I438(CS), Y444(F), N449(S), T450(IV), S452(A), 455.5(A), T456(V), Q457(T), S458(AP), R459(HKT), L460(CN), A467(CGPQ), S468(G), D469(AENQST), I470(LMV), R471(CKM), C482(IM), Y483(M), Q486(N), 490.5(N), T491(DE), A493(MP), N496(HS), S498(AFLM), Y500(M), T503(V), T506(ACV), K507(S), V517(I), S525(G), H526(ACNST), K532(HINQWY), F533(Y), K544(C), 545.5(D), T550(E), I554(L), K556(ENY), M558(F), D561(Q), E563(D), R566(ACGNSTV), T567(S), S578(DEIT), V579(V), S580(A), T581(DM), L583(I), A590(IP), A591(DEQS), T592(S), A593(DET), N596(C), T597(ACDHLNQW), Q598(ILMV), V600(AST), W606(F), Q607(M), V611(C), H623(NQ), T624(A), L639(C), H641(STVW), N656(H), 657.5(A), S658(W), 658.5(T), S662(F), A663(D), A664(PS), F666(HM), Q687(K), V708(FW), N709(A), and N734(P) | |
| L91(Y), V118(V), G189(F), S264(G), Y275(W), V387(M), R389(S), R459(H), L460(N), A467(CGPQ), D469(AEQST), 1470(LM), R471(K), C482(I), Q486(N), N496(H), S498(M), H526(CNS), K532(N), K544(C), T550(E), K556(Y), R566(AGTV), A590(P), A591(E), A593(DE), T597(HNQ), V611(C), V708(W), and N709(A) | 1.5-fold |
| R389(S), A467(G), D469(AEQS), I470(L), R471(K), Q486(N), N496(H), S498(M), H526(S), T550(E), A593(DE), and T597(N) | 2-fold |

TABLE 5

| Amino acid alterations conferring more efficient delivery to lung. | |
|---|---|
| Amino acid alteration | Fold increase of efficiency |
| E17(D), W23(T), L25(C), K33(T), 35.5(DE), E36(DV), 36.5(AP), 37.5(DSW), H38(N), 38.5(DQ), K39(P), 42.5(Y), E63(DR), A70(K), K77(EQR), R81(L), L83(I), D84(N), S85(FQ), K92(Q), A98(FQ), E99(V), Q101(N), E102(T), K105(F), F110(K), R116(FIQ), V118(V), E127(GL), L129(A), 129.5(P), 134.5(HKS), 135.5(PV), V136(P), 137.5(K), 140.5(APT), 141.5(AP), 145.5(FY), V146(HI), H148(-EQW), S149(W), 149.5(D), P150(I), V151(N), 151.5(NS), E152(S), 152.5(V), P153(P), S157(W), T159(EIQ), K161(F), A162(W), Q164(DEHLW), S181(E), D184(W), Q186(Y), L188(F), G189(DEQ), 189.5(DEK), 190.5(EINY), P191(GP), 192.5(P), A193(Q), A194(N), 194.5(D), T205(D), N214(D), Q263(AN), S264(G), S267(S), R310(K), T324(S), D327(E), T329(H), T344(AP), S356(N), V387(M), R389(S), T410(DQ), T414(R), V418(C), Y444(F), N449(Q), T450(I), S452(M), T454(IQ), T455(G), S458(AP), 458.5(Q), R459(F), Q461(G), A467(CGNPQ), S468(G), D469(AENQST), I470(LMV), R471(K), 490.5(N), T491(QW), N497(P), N518(M), P521(V), F533(Y), V539(C), K544(C), Q545(N), T550(A), K556(N), D561(Q), S578(T), S580(A), Q589(M), A590(P), A593(T), T597(AS), V600(A), W606(F), V611(C), H623(NY), L639(C), H641(NQS), I646(C), N656(A), P657(P), S658(AP), 658.5(Q), T659(AHV), S662(FQ), A667(N), S679(C), V708(W), and N709(A) | 1.1-fold |
| S264(G), A467(G), D469(AQT), I470(M), R471(K), 490.5(N), and V600(A) | 1.5-fold |

TABLE 6

| Amino acid alterations conferring more efficient delivery to spleen. | |
|---|---|
| Amino acid alteration | Fold increase of efficiency |
| E12(C), E17(D), Q21(DF), W23(G), 23.5(Y), P29(Y), P31(IT), 33.5(P), E36(D), 36.5(C), 37.5(HW), H38(K), 38.5(Q), E63(PS), V65(K), K77(E), D80(GKW), R81(GLTY), Q82(I), L83(I), D84(EN), S85(FQR), N88(F), H95(W), A98(Q), E99(AT), E102(IT), K105(F), E106(W), 107.5(F), T108(W), F110(KQW), G112(A), N113(Y), R116(F), Q120(HK), R124(A), V125(T), L129(E), 129.5(P), G130(ALW), L131(C), 132.5(D), 133.5(I), E134(N), 134.5(KRS), P135(-), 135.5(PVY), V136(-), 136.5(I), 138.5 (GHP), A139(FHNVW), 139.5(F), P140(E), 140.5(W), G141(E), 141.5(FG), K142(N), 142.5(I), 144.5(P), P145(F), V146(P), 147.5(LQVY), H148(QY), 148.5(W), S149(D), 149.5(P), P150(Y), 150.5(Q), 151.5(IP), E152(WY), 152.5(A), P153(P), A162(K), Q164(EPRS), P166(Q), A179(P), D184(W), 188.5(D), G189(DEQVY), 189.5(AHY), Q190(F), 190.5(ELQY), 191.5(D), P192(NRY), 192.5(F), A193(K), A194(N), 194.5(EW), P195(-), N201(Y), T205(CDHN), A209(C), N214(D), E216(D), Q263(N), S264(A), Y272(F), N312(K), D327(E), 327.5(G), T344(AEHPY), F370(F), M371(H), V372(I), Q401(N), L445(I), S458(A), R459(K), S468(G), D469(Q), T491(LQ), Y500(W), F533(Y), I541(C), M558(F), V579(V), S580(A), Q589(MN), A590(P), A591(S), A593(MT), T597(AMY), V600(AIT), V605(C), W606(F), D608(N), V611(C), H623(Y), T624(C), L639(C), H641(NQS), 658.5(T), T659(N), S662(H), 662.5(I), A664(Q), A667(F), T716(A), and N734(A) | 1.1-fold |
| Q589(M), and V600(A) | 1.5-fold |

TABLE 7

| Amino acid alterations that reduce delivery to liver. | |
|---|---|
| Amino acid alteration | Fold increase of efficiency |
| 4.5(HNV), 21.5(F), 23.5(E), 42.5(T), 45.5(M), K51(Y), Y52(D), P55(Y), G58(C), 82.5(D), 98.5(C), 144.5(N), P166(K), G174(H), D180(M), 180.5(M), 183.5(M), 184.5(M), G217(F), Q259(P), Q263(-), S264(-), 265.5(D), S267(E), 267.5(E), N268(E), 268.5(E), 269.5(D), N270(HY), R307(Y), 324.5(K), 379.5(DE), L380(E), N381(DMQ), 382.5(D), 383.5(E), 386.5(D), V387(E), G406(E), 412.5(Q), 431.5(Y), R432(-), D439(K), 444.5(CM), 445.5(ACDEGHILMNQS), S446(-), 446.5(ACEFGHIMNPQSTVWY), R447(-IPWY), 447.5(DEFGHIMNPQVW), T448(-DEGHILMNPQVWY), 448.5(DENP), N449(P), 449.5(E), G453(K), 453.5(Y), T454(F), 454.5(Y), T456(H), L460(WY), 460.5(W), S463(QV), 463.5(F), 469.5(E), R471(EG), D472(MT), S474(I), 475.5(SW), 476.5(L), 478.5(L), P479(T), 479.5(D), G480(Y), C482(W), 483.5(QV), R484(EFGHILMSVY), 484.5(N), 485.5(IKM), Q486(AFIMVWY), 486.5(FV), R487(DEFPY), 487.5(FW), V488(EH), 488.5(DEILMPQSWY), S489(-EFHKLMPQTY), 489.5(DGMPQRT), K490(-P), 490.5(HPQ), T491(P), 491.5(PW), 492.5(H), A493(H), 493.5(H), D494(FR), 494.5(AFGHILMNPVY), N495(-ADEFGHILPQSTVWY), 495.5(ACDFGILMNPSTV), N496(-EGL), 496.5(ADEFGHILNPSVY), N497(-), 497.5(ADEFGIPQSY), S498(-CEIPR), 498.5(DEGNPSVY), E499(CI), 499.5(ACDEGILMNPQSTVWY), Y500(-ACEGIKNP), 500.5(ADEFGHILMNPQSTVWY), S501(-IL), 501.5(ACDEFGHILMNQRSTVWY), W502(I), 502.5(ADEFGMNY), T503(E), 503.5(DEFGILMNQSW), G504(-DEHILMNPQSVWY), 504.5(ACDFHILMNPSTVWY), A505(DEILMNPY), 505.5(ACDEFGILMQTV), T506(M), 506.5(ACISVW), K507(-EF), 510.5(K), N511(EY), 523.5(A), 524.5(CGHST), 525.5(ACDFGILNPQSTVWY), H526(DKLP), 526.5(ACDEFGHMPQSVWY), K527(-DW), 527.5(ADEGHILMPQSVWY), D528(FPSW), 528.5(DPT), D529(ES), 529.5(DGLMNV), E530(NPW), 530.5(AEFIMNQTVWY), 531.5(ADFIKLNPQRSTVY), K532(-), 532.5(ACDFGHIKLMPQSTVWY), F533(D), 533.5(ACDFGHILNPQSTVWY), 534.5(F), P535(-F), Q536(-PW), 536.5(CITV), V571(DH), T573(IW), 573.5(T), 575.5(WY), Y576(V), 576.5(W), G577(D), 577.5(DEHIQS), 578.5(CDEILTVY), V579(DW), 579.5(DEINQTVY), S580(-DEQY), 580.5(DMNV), T581(-), 581.5(CDGILMPQY), N582(-FHP), 582.5(DFGHPTVW), 583.5(DEGMNSTVY), Q584(-DEFGHLNPVWY), 584.5(CEILP), R585(D), 585.5(DGI), G586(-), 586.5(ADFILMNQSV), N587(-H), 587.5(ADHMPQTW), R588(-GP), Q589(-D), 589.5(CDEHKNTV), A590(DEFKLMN), 590.5(DEKMQTWY), A591(-), 591.5(GHI), 592.5(ACEGILMTWY), A593(-P), 593.5(AFLMNPQSTVWY), 594.5(ACFGILMPTVWY), 595.5(ACFGILMS), 596.5(EY), 597.5(F), | 0.1-fold |

TABLE 7-continued

Amino acid alterations that reduce delivery to liver.

| Amino acid alteration | Fold increase of efficiency |
| --- | --- |
| 600.5(F), 606.5(P), D608(W), D610(Y), Q614(T), 617.5(I), S679(F), 705.5(Q), K706(ES), V710(M) | |
| 4.5(FHNV), G5(C), L11(C), E17(F), G18(D), I19(N), 21.5(F), 23.5(DEN), 24.5(H), L25(GH), 25.5(CKY), 28.5(T), P30(DY), 30.5(DKLRY), P32(E), 37.5(M), 42.5(T), 45.5(M), K51(Y), Y52(D), P55(Y), 55.5(K), G58(CE), G62(Q), 79.5(C), 82.5(D), G86(C), 87.5(Q), 90.5(E), Y93(N), 98.5(CE), 103.5(V), K105(M), 116.5(E), 123.5(FQ), 125.5(ES), 132.5(W), K143(Y), 144.5(N), P145(-E), 148.5(M), S156(T), 157.5(N), G163(K), Q164(M), P166(CIK), N172(W), 173.5(NQ), G174(H), D180(M), 180.5(M), 183.5(M), 184.5(M), 189.5(M), G217(F), T251(V), Q259(P), S261(ANT), Q263(-W), S264(-EVW), 265.5(D), 266.5(E), S267(EN), 267.5(E), N268(EQ), 268.5(E), 269.5(D), N270(HQY), H271(EIV), F273(HW), R307(Y), 324.5(K), Q349(AS), F365(W), L378(V), 379.5(DE), L380(E), 380.5(E), N381(ACDGMQS), N382(S), 382.5(D), 383.5(E), 386.5(D), V387(EW), 387.5(P), G406(DEQ), 406.5(Q), N408(G), 412.5(Q), 417.5(M), H426(N), Q428(EH), 431.5(Y), R432(-), D439(K), 444.5(CLM), 445.5(ACDEGHILMNQST), S446(-ELNV), 446.5(ACDEFGHILMNPQSTVWY), R447(-DEFIPWY), 447.5(ACDEFGHILMNPQVWY), T448(-DEFGHILMNPQVWY), 448.5(DEFHNPY), N449(-P), 449.5(E), T450(-), 450.5(E), 451.5(N), G453(FK), 453.5(INY), T454(F), 454.5(DY), T456(H), 456.5(E), R459(P), 459.5(P), L460(WY), 460.5(W), S463(KQV), 463.5(F), 464.5(SY), 466.5(E), 469.5(E), R471(EGQ), D472(MT), S474(I), R475(H), 475.5(SW), 476.5(L), W477(F), 477.5(L), 478.5(L), P479(T), 479.5(D), G480(Y), 481.5(G), C482(W), 483.5(QV), R484(EFGHILMQSTVY), 484.5(N), 485.5(EIKM), Q486(ACEFILMPVWY), 486.5(FV), R487(DEFKLMPSTY), 487.5(FW), V488(EGHMNY), 488.5(ACDEGILMPQSWY), S489 (-EFHIKLMNPQTVY), 489.5(ADGLMPQRST), K490(-DP), 490.5(DHPQ), T491(P), 491.5(AEFHLPTVWY), S492(-), 492.5(EGHQ), A493(H), 493.5(EHMNQ), D494(FR), 494.5(AFGHILMNPVY), N495 (-ADEFGHILMPQSTVWY), 495.5(ACDEFGILMNPSTVWY), N496 (-EGLMQ), 496.5(ADEFGHILNPSTVWY), N497(-CHW), 497.5(ADEFGIMNPQSTY), S498(-CDEINPRW), 498.5(ADEFGILMNPQSVWY), E499(CIPS), 499.5(ACDEGILMNPQRSTVWY), Y500(-ACEGHIKLNPTV), 500.5(ADEFGHILMNPQSTVWY), S501(-DILP), 501.5(ACDEFGHILMNPQRSTVWY), W502(-CEFILSV), 502.5(ADEFGILMNPSTVWY), T503(AEFGMQ), 503.5(ADEFGILMNPQSTVW), G504(-CDEFHILMNPQSTVWY), 504.5(ACDEFGHILMNPQSTVWY), A505(DEFHILMNPQTVWY), 505.5(ACDEFGILMPQTVWY), T506(MP), 506.5(ACIPSTVW), K507 (-EFY), H509(F), 509.5(K), 510.5(K), N511(ACDELWY), 512.5(S), R513(H), D514(LV), S515(I), 523.5(A), 524.5(CGHST), S525(M), 525.5(ACDFGILMNPQSTVWY), H526(DKLP), 526.5(ACDEFGHILMNPQSTVWY), K527(-DEFHPWY), 527.5(ACDEFGHILMPQSVWY), D528(EFMPSVW), 528.5(DEPT), D529(ES), 529.5(DEGLMNPV), E530(NPVW), 530.5(AEFGHIKLMNQRSTVWY), E531(CFIV), 531.5(ADFGIKLMNPQRSTVY), K532(-), 532.5(ACDEFGHIKLMPQSTVWY), F533(ADEGQSV), 533.5(ACDEFGHILNPQSTVWY), F534(I), 534.5(F), P535(-F), Q536 (-DFPW), 536.5(ACITV), S537(-), 537.5(T), G538(-), V539(H), 542.5(Q), 544.5(F), S547(-), 548.5(H), 550.5(EKM), 551.5(IMQ), E555(HN), V571(DEFHLMQY), T573(CHIW), 573.5(T), E574(LM), 575.5(WY), Y576(CGHV), 576.5(EFWY), G577(DW), 577.5(ACDEHIMQSV), 578.5(ACDEFILSTVY), V579(DW), 579.5(CDEFGILMNQTVY), S580 (-DEFILMNQY), 580.5(ADEFGLMNTV), T581(-), 581.5(ACDEGILMNPQTVY), N582(-AFGHMPWY), 582.5(DFGHPTVW), L583(-DGP), 583.5(DEGMNPSTVY), Q584(-ADEFGHILMNPTVWY), 584.5(CEILP), R585(-DPV), 585.5(DEGILMVW), G586(-), 586.5(ADEFGILMNQSTVY), N587(-H), 587.5(ADEHILMNPQSTVW), R588(-GPWY), 588.5(GHLMP), Q589(-DENTVY), 589.5(ACDEFHKNTVW), A590(DEFHKLMNQY), 590.5(CDEFGIKMQSTWY), A591(-), 591.5(CFGHILMPST), T592(-), 592.5(ACDEFGILMNQSTVWY), A593(-P), 593.5(ACFGILMNPQSTVWY), D594(L), 594.5(ACEFGHILMPQSTVWY), 595.5(ACFGILMNQSVW), 596.5(EY), 597.5(F), G599(W), 600.5(F), 606.5(P), D608(W), D610(Y), 610.5(F), Q614(T), 617.5(I), M634(C), 662.5(W), S679(FIY), E681(D), 704.5(AI), 705.5(Q), K706(EST), 709.5(Q), V710(M), 710.5(D) | 0.2-fold |
| 4.5(FHNV), G5(-C), 5.5(K), W10(CEKQRS), 10.5(HI), L11(C), 11.5(K), E12(I), D13(IY), E17(F), G18(D), I19(NQ), 21.5(FY), W22(V), 22.5(IM), W23(D), 23.5(ADEFHLNQT), 24.5(DEHIN), L25(GHN), 25.5(CIKLQVY), K26(Y), 26.5(N), 28.5(EILNST), P29(W), P30(DY), 30.5(DKLRY), P32(EGS), 37.5(M), S42(-), 42.5(T), 43.5(V), 45.5(M), K51(CY), Y52(D), | 0.3-fold |

TABLE 7-continued

| Amino acid alteration | Fold increase of efficiency |
| --- | --- |
| Amino acid alterations that reduce delivery to liver. | |
| P55(Y), 55.5(KY), G58(CE), D60(C), K61(-), G62(Q), L73(K), 78.5(D), 79.5(C), 81.5(W), 82.5(D), 83.5(Y), 84.5(Q), G86(C), 87.5(EQ), P89(H), 90.5(E), Y93(N), 93.5(Y), A96(QV), 98.5(CE), 103.5(V), K105(M), 105.5(C), 111.5(A), 112.5(CQ), N113(DW), 113.5(N), G115(-FP), 116.5(EQ), 117.5(FQ), V118(DR), 118.5(AC), F119(Q), 120.5(GR), 122.5(Q), 123.5(AFQT), R124(-), 124.5(CHK), 125.5(AEFS), L126(-), P128(F), 129.5(F), 130.5(K), 132.5(W), A139(D), P140(D), K142(D), 142.5(E), K143(VY), 143.5(EPTY), R144(P), 144.5(AN), P145(-E), 145.5(EMT), 148.5(M), 150.5(M), S156(T), 157.5(N), G163(K), Q164(M), 164.5(KP), P166(-CIK), 166.5(T), N172(DW), 173.5(INQ), G174(HTY), 174.5(K), D180(M), 180.5(M), 183.5(M), 184.5(M), G189(M), 189.5(M), Q190(M), P192(M), G217(F), S225(R), H229(D), 237.5(Q), T251(V), Q259(PS), S261(ANT), Q263(-DFW), S264(-DEVW), 265.5(ADS), A266(S), 266.5(AE), S267(ENP), 267.5(E), N268(EQ), 268.5(E), 269.5(D), N270(HQY), H271(EINV), F273(HW), R307(Y), P308(-), 324.5(K), Q325(K), A333(N), Q349(AS), F365(W), A367(P), L378(V), T379(G), 379.5(DE), L380(EMQ), 380.5(E), N381(ACDGMQS), N382(CEST), 382.5(D), 383.5(E), 384.5(D), A386(PT), 386.5(D), V387(EW), 387.5(P), S390(DT), 395.5(W), P399(Q), G406(DEQ), 406.5(Q), N408(DGM), F409(H), 412.5(Q), 416.5(E), 417.5(KM), H426(N), Q428(EH), S429(GP), L430(V), 431.5(Y), R432(-I), D439(KNY), 444.5(CLM), L445(FY), 445.5(ACDEGHILMNQST), S446(-ELNV), 446.5(ACDEFGHILMNPQSTVWY), R447(-DEFILMPVWY), 447.5(ACDEFGHILMNPQSVWY), T448(-ACDEFGHILMNPQVWY), 448.5(DEFGHINPY), N449(-DEHP), 449.5(ELP), T450(-), 450.5(E), 451.5(N), G453(AFKLQ), 453.5(INY), T454(FIN), 454.5(DFY), 455.5(H), T456(DEHN), 456.5(EH), S458(DEW), 458.5(HLMN), R459(-P), 459.5(P), L460(WY), 460.5(W), F462(Y), S463(GKQV), 463.5(F), 464.5(SY), 466.5(E), S468(CD), 469.5(E), R471(DEGQV), D472(LMTWY), S474(I), R475(H), 475.5(SW), 476.5(L), W477(F), 477.5(L), 478.5(L), P479(GT), 479.5(D), G480(Y), 481.5(GHY), C482(W), 483.5(QV), R484(EFGHILMQSTVY), 484.5(N), Q485(AG), 485.5(EIKM), Q486(ACEFILMPVWY), 486.5(FV), R487(ACDEFGKLMNPQSTVY), 487.5(FW), V488(EFGHMNQY), 488.5(ACDEFGILMPQSWY), S489 (-EFHIKLMNPQTVWY), 489.5(ADEGLMPQRSTV), K490(-DGP), 490.5(CDHMPQTY), T491(-P), 491.5(AEFGHILPQTVWY), S492(-), 492.5(EGHLQ), A493(-H), 493.5(DEHIKMNPQ), D494(FR), 494.5(AFGHILMNPQTVY), N495(-ADEFGHILMPQSTVWY), 495.5(ACDEFGILMNPSTVWY), N496(-EGLMPQW), 496.5(ADEFGHILMNPSTVWY), N497(-CGHLWY), 497.5(ADEFGILMNPQSTY), S498(-CDEINPRW), 498.5(ADEFGHILMNPQSVWY), E499(CIPS), 499.5(ACDEGILMNPQRSTVWY), Y500(-ACEGHIKLNPSTV), 500.5(ADEFGHILMNPQSTVWY), S501(-DILPVW), 501.5(ACDEFGHILMNPQRSTVWY), W502(-ACDEFGILMPQSV), 502.5(ADEFGILMNPQSTVWY), T503(-ADEFGHLMNQW), 503.5(ADEFGILMNPQSTVW), G504(-CDEFHILMNPQSTVWY), 504.5(ACDEFGHILMNPQSTVWY), A505(-CDEFHILMNPQTVWY), 505.5(ACDEFGILMPQSTVWY), T506(FLMP), 506.5(ACIPSTVW), K507(-EFY), H509(FK), 509.5(K), 510.5(K), N511(ACDEGLMSWY), 512.5(S), R513(H), D514(CFILMV), S515(I), N518(V), P521(M), 523.5(A), A524(G), 524.5(ACGHST), S525(M), 525.5(ACDEFGILMNPQSTVWY), H526(DIKLMPV), 526.5(ACDEFGHILMNPQSTVWY), K527 (-DEFHPSWY), 527.5(ACDEFGHILMPQSTVWY), D528(EFMPSVW), 528.5(DEPT), D529(ES), 529.5(DEGLMNPV), E530(NPVW), 530.5(ACDEFGHIKLMNQRSTVWY), E531(CFILV), 531.5(ADFGIKLMNPQRSTVY), K532(-CP), 532.5(ACDEFGHIKLMNPQSTVWY), F533(ADEGIQSV), 533.5(ACDEFGHILNPQSTVWY), F534(ILVY), 534.5(F), P535(-F), Q536 (-ADFGHPWY), 536.5(ACILTV), S537(-), 537.5(T), G538(-), V539(H), 542.5(Q), 543.5(P), K544(-), 544.5(FY), 545.5(W), 546.5(Q), S547(-), 547.5(NSY), E548(F), 548.5(CH), 549.5(D), 550.5(EKMQ), N551(P), 551.5(AEIMQ), 552.5(V), E555(HN), D561(I), 565.5(Y), R566(D), 567.5(E), P570(Q), 570.5(M), V571(ADEFHLMQY), T573(ACGHIWY), 573.5(T), E574(CFLM), 575.5(WY), Y576(ACGHIMV), 576.5(EFWY), G577(DW), 577.5(ACDEHIMQSTV), S578(F), 578.5(ACDEFILNSTVY), V579(DW), 579.5(ACDEFGILMNQTVWY), S580(-DEFILMNQY), 580.5(ACDEFGLMNTV), T581(-P), 581.5(ACDEGILMNPQTVY), N582 (-ADFGHKMPSWY), 582.5(DFGHNPSTVW), L583(-DGPW), 583.5(DEGMNPSTVY), Q584(-ADEFGHILMNPTVWY), 584.5(CEFGHILPV), R585(-CDILNPVY), 585.5(DEFGILMNPQSTVW), G586(-), 586.5(ADEFGHILMNQSTVY), N587(-EFHY), 587.5(ADEHILMNPQSTVW), R588(-ADGPSWY), 588.5(DFGHLMP), Q589(-DEINRTVY), 589.5(ACDEFHIKMNPTVWY), A590(DEFHKLMNQY), 590.5(ACDEFGIKLMQSTVWY), A591(-P), | |

TABLE 7-continued

| Amino acid alterations that reduce delivery to liver. | |
|---|---|
| Amino acid alteration | Fold increase of efficiency |
| 591.5(ACFGHILMNPQSTV), T592(-M), 592.5(ACDEFGILMNQSTVWY), A593(-P), 593.5(ACEFGILMNPQSTVWY), D594(LT), 594.5(ACDEFGHILMNPQSTVWY), V595(WY), 595.5(ACDFGHILMNQSTVW), N596(EPQ), 596.5(DEY), T597(P), 597.5(F), Q598(G), G599(W), 600.5(F), L601(W), P602(C), 606.5(P), D608(W), D610(Y), 610.5(F), Q614(T), I617(K), 617.5(I), H629(W), M634(C), 640.5(N), 657.5(C), 658.5(C), 659.5(C), T660(H), F661(I), 661.5(C), 662.5(W), 663.5(CW), 665.5(RW), F666(C), 667.5(Y), S679(FIY), E681(D), 699.5(E), 703.5(AEL), 704.5(AILN), 705.5(QY), K706(EST), S707(L), 707.5(Y), V708(N), 708.5(I), N709(P), 709.5(PQ), V710(M), 710.5(D), D711(G), T716(R), S721(H), P723(D), R724(F) | |
| 1.5(M), A3(CD), 3.5(I), 4.5(AFHNVY), G5(-C), 5.5(FKM), 6.5(N), W10(ACEGKPQRSTY), 10.5(HI), L11(AC), 11.5(K), E12(FI), D13(EIKWY), T14(CDQ), L15(HT), E17(CFVY), G18(D), I19(EGHNQT), R20(Q), 21.5(FWY), W22(IV), 22.5(IMWY), W23(DK), 23.5(ADEFGHLNQSTWY), 24.5(CDEHILN), L25(EFGHNQR), 25.5(CEIKLNQRSTVWY), K26(Y), 26.5(NQ), P27(T), 28.5(AEFILNPQSTW), P29(DEQRSTW), P30(DFHQRSY), 30.5(DEKLNQRTY), P31(H), 31.5(AFV), P32(EGIRS), 32.5(DEKNP), K33(Q), 33.5(CKNVWY), 34.5(FQ), A35(HNQY), E36(H), 36.5(IN), R37(DN), 37.5(M), H38(W), 38.5(G), K39(F), 39.5(DY), D40(-ACNY), 40.5(Y), D41(H), 41.5(NW), S42(-LVW), 42.5(DT), R43(AT), 43.5(PV), 45.5(M), Y50(HW), K51(ACLMVY), Y52(D), P55(Y), 55.5(EKY), 56.5(K), G58(CE), 58.5(F), L59(CGK), 59.5(H), D60(CY), K61(-IS), 61.5(G), G62(Q), A68(T), L73(HK), E74(TW), 77.5(K), A78(FY), 78.5(ADIQ), Y79(C), 79.5(CK), 80.5(F), 81.5(HW), 82.5(DK), 83.5(HKY), 84.5(NQ), 85.5(KS), G86(-C), 86.5(Q), 87.5(DEFQ), P89(CH), 89.5(GL), 90.5(EMY), L91(Q), 92.5(RY), Y93(GN), 93.5(Y), 94.5(Y), A96(QV), A98(C), 98.5(CE), F100(K), 101.5(E), E102(FQ), 103.5(SV), L104(N), 104.5(EKN), K105(M), 105.5(CRY), E106(CF), 106.5(HNY), D107(CKY), 107.5(N), T108(-), 108.5(QY), S109(N), 109.5(Y), 111.5(AW), 112.5(CQ), N113(DIKLRW), 113.5(FN), G115(-DFMPV), 115.5(DHLVW), R116(EP), 116.5(EHIKLPQTWY), A117(EKR), 117.5(EFKLPQW), V118(-DKPR), 118.5(ACEGP), F119(CQS), 119.5(AHKLNQRSVY), 120.5(GKLPR), A121(E), 121.5(FG), K122(FNW), 122.5(HIQW), K123(CDHT), 123.5(AFKNQT), R124(-IP), 124.5(CHKPRS), V125(-DPQ), 125.5(ACEFGQRSW), L126(-R), 126.5(CER), E127(-), 127.5(LNSY), P128(CFI), 128.5(AHKTW), L129(DKR), 129.5(F), 130.5(CKSY), 131.5(DEHP), V132(C), 132.5(IW), 135.5(W), 136.5(EM), K137(CDY), 137.5(DLNQSY), 138.5(DNQ), A139(DF), 139.5(D), P140(DE), 140.5(CDEKN), G141(EFKLMQWY), 141.5(DEY), K142(DEGPY), 142.5(DEKPSY), K143(EGVY), 143.5(ELPQSTY), R144(HPSTVW), 144.5(ACFHNSTY), P145(-DENSVY), 145.5(EGMPQT), V146(DE), 146.5(R), E147(FGHKLQY), 147.5(K), 148.5(MR), S149(MPQ), 149.5(CMW), P150(M), 150.5(EM), V151(-), 152.5(HK), S156(AT), 157.5(N), G160(Y), 160.5(N), K161(Y), 161.5(F), G163(CFK), 163.5(DNR), Q164(M), 164.5(KPY), Q165(CHN), 165.5(FIPTV), P166 (-ACFIKLNQRSTY), 166.5(FINTY), R168(K), R170(K), N172(-DSVW), 172.5(F), 173.5(DFHINQ), G174(ACDHQSTWY), 174.5(IK), Q175(ANRT), 175.5(I), T176(CG), 176.5(N), G177(-Q), D178(-IW), A179(K), 179.5(CY), D180(MNY), 180.5(M), 181.5(TY), 182.5(CLS), 183.5(M), 184.5(MY), P185(TW), 185.5(FQ), Q186(N), 186.5(CKY), P187(F), 187.5(QY), L188(MT), G189(IM), 189.5(MQ), Q190(MW), P192(CKM), 192.5(HM), 193.5(W), 194.5(M), S196(-), L198(VW), G199(D), 199.5(W), T200(N), M203(DEHW), T205(Y), G206(EKY), S207(D), G208(E), P210(CH), D213(HW), N214(F), N215(I), G217(DEFHITVY), A218(Q), G220(CMN), N223(DH), S225(CR), H229(ADV), T233(DHV), 237.5(HNQ), R238(H), 238.5(T), I240(H), T242(HY), T246(I), T251(V), N254(C), L256(AGKMS), K258(Q), Q259(AGKPRS), 260.5(Q), S261(ACGNT), 262.5(D), Q263 (-DFGHLTWY), S264(-DEILQVWY), 265.5(ADENS), A266(S), 266.5(AE), S267(AENP), 267.5(E), N268(AEQ), 268.5(E), 269.5(D), N270(ACDGHQSY), H271(EINV), F273(HW), G280(A), F282(WY), D295(E), R307(-CDMY), P308(-N), L311(Y), K314(CFLQTVWY), I318(F), T324(L), 324.5(K), Q325(HKR), 325.5(R), D327(Q), T329(C), T330(K), T331(H), I332(CS), 332.5(K), A333(DHNY), L336(I), T339(C), V342(M), T344(FI), S346(F), Q349(AMS), F365(W), A367(P), L378(AV), T379(CG), 379.5(DE), L380(CEMNQTV), 380.5(E), N381(ACDGMQS), N382(CDEST), 382.5(D), 383.5(E), S384(G), 384.5(D), Q385(EKLTV), 385.5(K), A386(EHPTVW), 386.5(CDE), V387(CDETWY), 387.5(EKP), G388(M), R389(I), S390(ADGT), 395.5(W), Y397(AN), P399(Q), Q401(FIY), L403(C), R404(K), T405(SY), G406(DENQ), 406.5(Q), N408(DFGMQ), 408.5(N), F409(CH), T410(FM), S412(VW), 412.5(Q), Y413(M), T414(F), E416(G), 416.5(CE), D417(MN), 417.5(KM), V418(Q), P419(W), F420(LM), A425(FQ), H426(N), S427(AN), Q428(EHN), S429(GP), L430(MV), 431.5(Y), R432(-I), 433.5(F), L437(N), | 0.5-fold |

TABLE 7-continued

Amino acid alterations that reduce delivery to liver.

| Amino acid alteration | Fold increase of efficiency |
|---|---|
| D439(KNSY), 444.5(CLM), L445(FMY), 445.5(ACDEGHILMNQSTV), S446(-EGHILMNTV), 446.5(ACDEFGHILMNPQSTVWY), R447(-DEFGILMNPTVWY), 447.5(ACDEFGHILMNPQSVWY), T448(-ACDEFGHILMNPQSVWY), 448.5(ACDEFGHILMNPQY), N449(-DEHMPW), 449.5(AEHLNPS), T450(-CNP), 450.5(DEFGLT), P451(-I), 451.5(NP), S452(NP), 452.5(AL), G453(-AEFIKLNQST), 453.5(FINY), T454(DFHIN), 454.5(DFY), T455(-DEMNY), 455.5(HP), T456(DEFGHIN), 456.5(DEH), Q457(GP), 457.5(ADWY), S458(DEFW), 458.5(DEHILMNT), R459(-P), 459.5(DP), L460(HWY), 460.5(W), Q461(DFI), F462(Y), 462.5(N), S463(CGKNQV), 463.5(F), Q464(K), 464.5(SY), A465(G), 466.5(E), S468(CDEY), 469.5(E), R471(DEGQTV), D472(LMSTWY), Q473(F), S474(CI), R475(H), 475.5(SW), N476(ST), 476.5(L), W477(F), 477.5(L), 478.5(L), P479(GT), 479.5(D), G480(Y), P481(AV), 481.5(GHY), C482(GQWY), Y483(AT), 483.5(QV), R484(EFGHIKLMNQSTVY), 484.5(N), Q485(AGSY), 485.5(EIKM), Q486(ACDEFGILMPVWY), 486.5(FV), R487(-ACDEFGKLMNPQSTVWY), 487.5(FW), V488(AEFGHLMNQY), 488.5(ACDEFGILMPQSVWY), S489(-EFGHIKLMNPQTVWY), 489.5(ACDEGLMPQRSTVY), K490(-ACDFGPQWY), 490.5(CDFGHILMPQTVWY), T491(-GP), 491.5(AEFGHILMPQSTVWY), S492(-CGM), 492.5(AEGHILMQSTVY), A493(-HQ), 493.5(ADEHIKMNPQSTV), D494(FR), 494.5(ADFGHILMNPQSTVY), N495(-ADEFGHILMPQSTVWY), 495.5(ACDEFGILMNPQSTVWY), N496(-CDEFGILMPQTVW), 496.5(ADEFGHILMNPQSTVWY), N497(-CEFGHLMWY), 497.5(ADEFGILMNPQSTVY), S498(-CDEINPRTVW), 498.5(ADEFGHILMNPQSTVWY), E499(CIPS), 499.5(ACDEGILMNPQRSTVWY), Y500(-ACDEGHIKLNPQSTVW), 500.5(ADEFGHILMNPQSTVWY), S501(-CDFILPRVW), 501.5(ACDEFGHILMNPQRSTVWY), W502(-ACDEFGILMPQSVY), 502.5(ADEFGHILMNPQSTVWY), T503(-ADEFGHLMNQSWY), 503.5(ADEFGILMNPQSTVW), G504(-CDEFHILMNPQSTVWY), 504.5(ACDEFGHILMNPQSTVWY), A505(-CDEFGHILMNPQSTVWY), 505.5(ACDEFGILMPQSTVWY), T506(FGILMPQ), 506.5(ACIPSTVW), K507(-EFNWY), Y508(IMV), H509(EFKNQR), 509.5(K), 510.5(K), N511(ACDEGLMQSWY), 512.5(S), R513(H), D514(ACFGILMV), S515(CINV), L516(ACS), V517(L), N518(V), P521(MS), M523(CV), 523.5(A), A524(G), 524.5(ACGHSTW), S525(CMNPT), 525.5(ACDEFGHILMNPQSTVWY), H526(DEFGIKLMPRVWY), 526.5(ACDEFGHILMNPQSTVWY), K527(-DEFGHILPSTVWY), 527.5(ACDEFGHILMPQSTVWY), D528(AEFMPQSVW), 528.5(DEPT), D529(ES), 529.5(ADEGLMNPQV), E530(DNPVW), 530.5(ACDEFGHIKLMNQRSTVWY), E531(ACFGILMNPQSTVY), 531.5(ADEFGIKLMNPQRSTVY), K532(-CEP), 532.5(ACDEFGHIKLMNPQSTVWY), F533(ACDEGHIQSTVW), 533.5(ACDEFGHILNPQSTVWY), F534(ILVWY), 534.5(F), P535(-F), Q536(-ADFGHNPSTVWY), 536.5(ACILTV), S537(-DFGQY), 537.5(T), G538(-), V539(HL), L540(M), 541.5(D), 542.5(Q), 543.5(DIKPRT), K544(-F), 544.5(FKMRVWY), Q545(-), 545.5(CFIMNSTW), G546(CFHQ), 546.5(ACEGHMNQSW), S547(-DWY), 547.5(GHLNPSTWY), E548(AFGLP), 548.5(ACGHILNPT), K549(DQ), 549.5(ADLNQSTV), T550(-CY), 550.5(EKMPQRSTV), N551(-CPV), 551.5(ACEILMPQ), 552.5(V), D553(AGST), I554(H), E555(GHNS), 556.5(Q), M558(IV), T560(V), D561(I), 565.5(Y), R566(DFHLQ), 567.5(E), P570(Q), 570.5(M), V571(ADEFHILMQSTY), 572.5(WY), T573(ACDGHIVWY), 573.5(T), E574(ACDFLMSW), Q575(CT), 575.5(WY), Y576(ACGHIMSV), 576.5(EFWY), G577(DW), 577.5(ACDEHIMNQSTV), S578(FHLY), 578.5(ACDEFGHILNSTVY), V579(DFQWY), 579.5(ACDEFGILMNPQTVWY), S580(-DEFHILMNQVY), 580.5(ACDEFGKLMNPSTVY), T581(-GHPQW), 581.5(ACDEGILMNPQTVY), N582(-ACDEFGHIKLMPQRSTWY), 582.5(DFGHNPSTVW), L583(-DEGPWY), 583.5(DEGIMNPQSTVY), Q584(-ADEFGHILMNPSTVWY), 584.5(ACDEFGHILMPQTVWY), R585(-ACDILMNPSTVWY), 585.5(DEFGHILMNPQSTVWY), G586(-HVY), 586.5(ADEFGHILMNPQSTVY), N587(-EFHILVY), 587.5(ADEFGHILMNPQSTVWY), R588(-ACDEFGHILMNPQSTVWY), 588.5(DEFGHLMNPSY), Q589(-DEFGINPRSTVY), 589.5(ACDEFGHIKLMNPSTVWY), A590(DEFHKLMNQTWY), 590.5(ACDEFGIKLMPQSTVWY), A591(-FPWY), 591.5(ACEFGHILMNPQSTVY), T592(-CEGHLMP), 592.5(ACDEFGILMNPQSTVWY), A593(-FPY), 593.5(ACDEFGHILMNPQSTVWY), D594(LT), 594.5(ACDEFGHILMNPQSTVWY), V595(DEFHNPQWY), 595.5(ACDEFGHILMNQSTVW), N596(EFIPQW), 596.5(DEY), T597(P), 597.5(F), Q598(EGN), G599(W), 600.5(F), L601(W), P602(CQ), M604(C), 606.5(P), D608(W), D610(Y), 610.5(F), 613.5(Y), Q614(T), I617(K), | |

TABLE 7-continued

| Amino acid alterations that reduce delivery to liver. | |
|---|---|
| Amino acid alteration | Fold increase of efficiency |
| 617.5(I), K620(CMN), H627(M), H629(WY), P630(G), L633(M), M634(C), F637(I), K640(VW), 640.5(N), Q645(M), I646(M), L647(I), N650(C), V653(C), N656(Q), 657.5(C), 658.5(ACHN), 659.5(CDI), T660(HM), 660.5(E), F661(AEILQST), 661.5(CGKPRY), 662.5(CKMQW), 663.5(CGPW), A664(KW), 664.5(CMPR), K665(H), 665.5(HINRTWY), F666(C), 666.5(I), A667(CM), 667.5(QY), T671(R), S674(G), S679(FGHIKRY), V680(C), E681(D), Q687(I), K688(P), E697(D), 697.5(G), I698(D), 699.5(E), 702.5(Q), N703(G), 703.5(AEHLTY), 704.5(AILNS), 705.5(QY), K706(DEST), S707(CEHILMNY), 707.5(MY), V708(ACGHN), 708.5(I), N709(P), 709.5(GPQ), V710(AMNPQ), 710.5(D), D711(GN), T713(C), T716(CKRW), N717(R), V719(KY), S721(CHKLMNR), E722(Q), P723(CDEN), R724(FSY), P725(I), I726(L) | |
| 1.5(MV), A2(CS), 2.5(GIMP), A3(CDEFI), 3.5(ILTVY), D4(CS), 4.5(AFHNVY), G5(-CN), 5.5(CFKM), 6.5(N), W10(ACEGIKPQRSTY), 10.5(HI), L11(ACV), 11.5(K), E12(FHIW), D13(CEGIKVWY), T14(CDFHIPQR), L15(HTW), E17(CFINQRTVY), G18(ADS), I19(AEGHNQST), R20(FILQV), Q21(GHKTV), 21.5(FWY), W22(FIV), 22.5(FILMWY), W23(CDEHKMNQ), 23.5(ACDEFGHLNQSTWY), 24.5(CDEHILNY), L25(AEFGHNQRS), 25.5(CEIKLNQRSTVWY), K26(DHNY), 26.5(HNQ), P27(T), 27.5(G), 28.5(AEFGILNPQSTVWY), P29(DEFGLQRSTW), P30(ADFHQRSY), 30.5(ADEFGIKLNPQRSTY), P31(DHK), 31.5(AFILPV), P32(AEGHILNQRSTY), 32.5(ADEKLNPRSTW), K33(-DGNPQRSY), 33.5(CEFKNPQTVWY), P34(-GLQRTVY), 34.5(CEFGHKQRVY), A35(EGHKNQVY), 35.5(CGHT), E36(FHK), 36.5(FINW), R37(-DN), 37.5(MPQ), H38(CENW), 38.5(CDEGIKNP), K39(AFLVY), 39.5(CDGIY), D40(-ACNY), 40.5(CDGY), D41(EHQRS), 41.5(DFNRTVW), S42(-DKLQRTVW), 42.5(CDGT), R43(ASTV), 43.5(DPRV), 45.5(M), V46(I), L47(F), P48(Y), G49(CFLMQY), Y50(HW), 50.5(N), K51(ACFLMNVY), Y52(D), 53.5(R), P55(Y), 55.5(EKY), 56.5(K), G58(CES), 58.5(F), L59(ACFGKQRW), 59.5(H), D60(CHNTY), K61(-CILQS), 61.5(GK), G62(Q), E67(DLQ), A68(LT), L73(EHKV), E74(QTW), K77(D), 77.5(K), A78(FY), 78.5(ADFHIQR), Y79(-C), 79.5(CK), 80.5(F), R81(CDQ), 81.5(FHW), Q82(EHMN), 82.5(DIK), L83(CGN), 83.5(FGHIKLQWY), 84.5(ENQ), S85(-E), 85.5(GHKS), G86(-ACDEVW), 86.5(FQSVW), D87(ACHK), 87.5(ADEFGQ), N88(A), P89(CDH), 89.5(GL), 90.5(EMY), L91(Q), K92(G), 92.5(RY), Y93(GHNW), 93.5(Y), 94.5(AY), H95(AEGRY), A96(QVW), D97(-G), A98(CDW), 98.5(CE), E99(CG), 99.5(N), F100(K), Q101(DVY), 101.5(E), E102(FQ), R103(IN), 103.5(SV), L104(NT), 104.5(ADEGKNV), K105(FMQW), 105.5(CQRWY), E106(CFIK), 106.5(EFHNRY), D107(-CFKVY), 107.5(NP), T108(-CI), 108.5(IQY), S109(CILN), 109.5(AHY), F110(CEHNY), G111(CE), 111.5(AW), G112(P), 112.5(CQ), N113(CDHIKLQRVW), 113.5(FHN), L114(FN), G115 (-DEFMPV), 115.5(ADEHLNVW), R116(EGMP), 116.5(ADEGHIKLPQTWY), A117(CEHKQRWY), 117.5(DEFKLPQW), V118(-DKPRW), 118.5(ACEGMP), F119(ACHQS), 119.5(AHIKLNQRSTVY), Q120(-FKW), 120.5(GKLPR), A121(EFKNQ), 121.5(FGHQ), K122(-DFGNRW), 122.5(DFHIKPQSW), K123(CDFHT), 123.5(AFKNPQT), R124(-CHIP), 124.5(CEFHKPRS), V125 (-CDEHPQSW), 125.5(ACEFGQRSW), L126(-KQR), 126.5(CER), E127(-P), 127.5(AGILNSTY), P128(CDFILQRSTV), 128.5(AGHKLRSTW), L129(DKR), 129.5(CFQ), G130(EFQ), 130.5(CEHKLSTY), L131(DI), 131.5(ADEFHLP), V132(CR), 132.5(HIKLNVWY), E133(GLS), 133.5(PW), 134.5(HW), P135(H), 135.5(LW), V136(-HY), 136.5(AEHMNQ), K137(-CDPTY), 137.5(CDGHIKLNPQRSVWY), T138(AEGPQ), 138.5(CDEGKNQSW), A139(-CDEFKQTW), 139.5(CDGHRY), P140(DEGHTW), 140.5(CDEKNQ), G141(DEFHIKLMNQRTWY), 141.5(DEHKQRTVY), K142(-CDEGNPY), 142.5(CDEFGIKNPQSWY), K143(EGRVY), 143.5(AEFKLPQSTY), R144(HNPSTVW), 144.5(ACEFHILNPQRSTVWY), P145 (-ADEFGILNSVWY), 145.5(DEGKMPQTV), V146(DEKQRTW), 146.5(CEFKLNPRY), E147(FGHKLNQVY), 147.5(EFHK), H148(CGW), 148.5(HKMNR), S149(-ACEHIMNPQR), 149.5(CHIKMNRTW), P150(DFHMR), 150.5(DEMPRW), V151(-CDGY), 151.5(DY), E152(CFP), 152.5(DGHKNY), D154(S), 155.5(D), S156(AT), S157(EFKRTV), 157.5(DNQTW), G158(D), 158.5(P), T159(EFGHPQ), 159.5(Y), G160(Y), 160.5(DNWY), K161(GHNTVY), 161.5(FGILQRSV), A162(IQ), 162.5(EPRT), G163(CFKN), 163.5(DEKNRSTWY), Q164(CMR), 164.5(DEFGIKNPRY), Q165(CHILNVW), 165.5(FIPTV), P166 (-ACFHIKLNQRSTY), 166.5(FGHINPSTY), A167(QSV), R168(K), R170(K), N172(-ACDFHLQSVW), 172.5(F), 173.5(ADFHINQWY), G174(ACDEFHQSTWY), 174.5(IKNS), Q175(-ADNRST), 175.5(AFGIKNY), T176(ACGY), 176.5(ENP), G177(-Q), 177.5(EGI), D178(-EIWY), 178.5(INPS), A179(-IKW), 179.5(CDHNPQRSTVWY), D180(-ACFIMNY), 180.5(CFHIMQ), S181(FKL), 181.5(CGHNTVY), | 0.7-fold |

TABLE 7-continued

Amino acid alterations that reduce delivery to liver.

| Amino acid alteration | Fold increase of efficiency |
| --- | --- |
| 182.5(CHLPS), P183(CS), 183.5(EGKMNY), D184(FGHINPQR), 184.5(MPRY), P185(DEFILNTVWY), 185.5(CFIPQTVW), Q186(FNPTY), 186.5(CDEKSY), P187(FGIL), 187.5(CGKPQWY), L188(EFIMSTW), 188.5(DN), G189(CIMN), 189.5(MQW), Q190(MW), 190.5(CFGH), P191(N), 191.5(CIQW), P192(CKMWY), 192.5(EHMY), A193(DNY), 193.5(DHMRVW), A194(CFGIQV), 194.5(CFMP), P195(DKQRSTY), 195.5(DHMQST), S196(-FK), L198(DVWY), G199(D), 199.5(FHW), T200(AFINQR), N201(CH), T202(KPSV), M203(ACDEFGHIPRTVWY), T205(FKRVY), G206(ACDEHKRY), S207(ADRY), G208(EFHKLQWY), A209(DEMY), P210(CHR), D213(ACFHIKLNTW), N214(ACEFLVY), N215(CHILY), E216(AH), G217(ACDEFHILMNSTVY), A218(Q), G220(ACMNT), N223(ACDHIY), S225(CQR), H229(ADSTV), T233(DHIQVY), M235(L), D237(C), 237.5(EHKNQ), R238(HS), 238.5(TY), I240(H), T242(CHRY), T246(I), P250(S), T251(SV), N254(CQS), L256(ACGKMQRSV), K258(Q), Q259(AGHKPRS), 260.5(MQ), S261(ACGNT), 262.5(D), Q263(-DEFGHLTWY), S264(-DEILQVWY), 265.5(ADEMNQS), A266(S), 266.5(AE), S267(AENP), 267.5(E), N268(ADEQ), 268.5(E), 269.5(D), N270(ACDGHQSY), H271(EFINV), F273(HWY), S276(K), G280(A), F282(LWY), F284(CY), F287(Y), H288(N), S292(C), D295(AE), R307(-CDKMSY), 307.5(FK), P308(-NV), K309(AQ), R310(GILV), L311(CFY), N312(HMT), K314(CFGLQSTVWY), L315(V), I318(F), T324(LM), 324.5(KR), Q325(HKRV), 325.5(FHIKR), N326(DMRWY), D327(QT), G328(AN), T329(CIY), T330(KQ), T331(FHY), I332(ACS), 332.5(K), A333(DFHNTY), N334(S), L336(I), T339(C), V342(ACIM), T344(DFILN), S346(CFHLMPQW), Y348(FRS), Q349(AGMS), V353(CI), S356(A), H358(ACGN), Q359(M), F365(W), A367(CP), V369(PT), M371(CIKQS), G376(CS), L378(ACV), T379(ACGSV), 379.5(DE), L380(CEMNQTVY), 380.5(E), N381(ACDGMQS), N382(CDEST), 382.5(D), 383.5(E), S384(AG), 384.5(D), Q385(EKLMSTV), 385.5(DEK), A386(-EHLNPRTVW), 386.5(CDEY), V387(CDEQTWY), 387.5(EGKP), G388(EIM), R389(IL), S390(ADGNT), C394(V), 394.5(N), 395.5(W), Y397(AGN), P399(EIMQR), Q401(CDFIKLNRVWY), L403(C), R404(K), 404.5(N), T405(SY), G406(DENQ), 406.5(Q), 407.5(H), N408(ADFGHLMQTY), 408.5(N), F409(CH), T410(CFHLMY), F411(CTW), S412(IKVWY), 412.5(Q), Y413(FM), T414(FK), 414.5(D), 415.5(APQ), E416(DG), 416.5(CEMR), D417(AIKMNTV), 417.5(DKLMRS), V418(GQ), P419(EINTVW), F420(LM), S422(A), S423(LT), Y424(FH), A425(-CFQV), H426(N), S427(AN), Q428(EHN), S429(CGHPY), L430(MV), D431(M), 431.5(Y), R432(-I), L433(V), 433.5(F), L437(NS), I438(M), D439(KNPSY), 441.5(M), 444.5(CLM), L445(FMY), 445.5(ACDEGHILMNQSTVY), S446(-DEGHILMNQTV), 446.5(ACDEFGHILMNPQSTVWY), R447(-ADEFGILMNPQTVWY), 447.5(ACDEFGHILMNPQSVWY), T448(-ACDEFGHILMNPQSVWY), 448.5(ACDEFGHILMNPQSY), N449(-CDEHILMPVWY), 449.5(AEGHLMNPST), T450(-CFGNPY), 450.5(ADEFGHLTV), P451(-I), 451.5(NP), S452(-DEFGNPQTY), 452.5(ALV), G453(-AEFIKLMNPQST), 453.5(FILNY), T454(-DEFGHILMNP), 454.5(DEFPY), T455(-ADEILMNPQVY), 455.5(HNP), T456(DEFGHIKMNS), 456.5(DEGHIL), Q457(EGHILMPS), 457.5(ADEGHNTWY), S458(DEFHMNW), 458.5(CDEGHILMNT), R459(-EGINPY), 459.5(DEP), L460(AHIMTWY), 460.5(W), Q461(DFHIKV), F462(Y), 462.5(N), S463(ACDGKMNQRV), 463.5(F), Q464(IKLMV), 464.5(SY), A465(G), G466(A), 466.5(E), A467(EM), S468(CDELPQVY), D469(V), 469.5(E), R471(DEGQSTV), D472(GHLMSTVWY), Q473(FHY), S474(CIY), R475(H), 475.5(SW), N476(ST), 476.5(L), W477(F), 477.5(L), L478(FI), 478.5(L), P479(GIT), 479.5(D), G480(Y), P481(ACV), 481.5(GHY), C482(AFGQSWY), Y483(AITW), 483.5(FHQV), R484(EFGHIKLMNQSTVY), 484.5(N), Q485(ACGNSTY), 485.5(EIKMY), Q486(ACDEFGILMPSVWY), 486.5(FV), R487(-ACDEFGIKLMNPQSTVWY), 487.5(FW), V488(AEFGHILMNQTWY), 488.5(ACDEFGILMPQSVWY), S489(-EFGHIKLMNPQTVWY), 489.5(ACDEGLMPQRSTVWY), K490(-ACDEFGMNPQRSTVWY), 490.5(CDEFGHILMPQRSTVWY), T491(-AGPY), 491.5(ADEFGHILMNPQSTVWY), S492(-CFGLMPQT), 492.5(AEGHILMPQSTVY), A493(-HQ), 493.5(ADEGHIKLMNPQSTVY), D494(EFR), 494.5(ADFGHILMNPQSTVWY), N495(-ADEFGHILMPQSTVWY), 495.5(ACDEFGILMNPQSTVWY), N496(-ACDEFGILMPQTVWY), 496.5(ADEFGHILMNPQSTVWY), N497(-CEFGHLMVWY), 497.5(ADEFGILMNPQSTVY), S498(-CDEINPRTVW), 498.5(ADEFGHILMNPQSTVWY), E499(CIPS), 499.5(ACDEGILMNPQRSTVWY), Y500(-ACDEGHIKLNPQSTVW), 500.5(ADEFGHILMNPQSTVWY), S501(-CDEFILMPRTVW), 501.5(ACDEFGHILMNPQRSTVWY), W502(-ACDEFGILMPQSTVY), 502.5(ADEFGHILMNPQSTVWY), T503(-ADEFGHLMNQSWY), 503.5(ADEFGILMNPQSTVW), G504(-ACDEFHILMNPQSTVWY), | |

TABLE 7-continued

Amino acid alterations that reduce delivery to liver.

| Amino acid alteration | Fold increase of efficiency |
|---|---|
| 504.5(ACDEFGHILMNPQSTVWY), A505(-CDEFGHILMNPQSTVWY), 505.5(ACDEFGILMPQSTVWY), T506(-FGILMPQS), 506.5(ACIPSTVW), K507(-ACEFHLNVWY), Y508(-DIMSTV), H509(EFKNQR), 509.5(K), L510(I), 510.5(K), N511(ACDEGLMQSWY), 512.5(S), R513(HI), D514(ACFGILMSV), S515(ACINTV), L516(ACMRS), V517(L), N518(TVY), P521(FMS), 521.5(M), A522(CV), M523(CLV), 523.5(A), A524(GP), 524.5(ACGHSTW), S525(CMNPT), 525.5(ACDEFGHILMNPQSTVWY), H526(DEFGIKLMPRVWY), 526.5(ACDEFGHILMNPQSTVWY), K527(-DEFGHILPSTVWY), 527.5(ACDEFGHILMPQSTVWY), D528(AEFMPQSVW), 528.5(DEPT), D529(ES), 529.5(ADEGLMNPQTV), E530(DNPVW), 530.5(ACDEFGHIKLMNQRSTVWY), E531(ACFGHILMNPQSTVY), 531.5(ADEFGIKLMNPQRSTVY), K532(-CDEP), 532.5(ACDEFGHIKLMNPQSTVWY), F533(ACDEGHILNQSTVW), 533.5(ACDEFGHILNPQSTVWY), F534(ILVWY), 534.5(F), P535(-AF), Q536(-ACDEFGHMNPSTVWY), 536.5(ACILTV), S537(-DFGNQTY), 537.5(T), G538(-), V539(HLMQST), L540(M), 540.5(N), I541(DERT), 541.5(ACDQV), 542.5(Q), G543(APS), 543.5(DHIKLMPRTV), K544(-FS), 544.5(AFGHIKLMNRVWY), Q545(-AKLRW), 545.5(ACFHILMNPQSTVWY), G546(ACEFHLPQSVWY), 546.5(ACDEGHILMNQSTVWY), S547(-DGLNQWY), 547.5(ADGHILMNPSTVWY), E548(AFGLMNPS), 548.5(ACDGHILNPSTWY), K549(-DEFGHLPQSY), 549.5(ADFGLMNQSTVY), T550(-CQY), 550.5(AEGIKMPQRSTV), N551(-CEGIPQRSV), 551.5(ACDEFILMPQST), V552(CQS), 552.5(VW), D553(AGST), I554(AHTW), E555(AGHNSTVY), K556(CDM), 556.5(Q), V557(IL), M558(IV), I559(FQV), T560(V), D561(INRVY), I565(T), 565.5(Y), R566(DFHLQY), 567.5(E), T568(P), 569.5(M), P570(QS), 570.5(M), V571(ADEFHILMQSTY), A572(CY), 572.5(WY), T573(ACDGHINSVWY), 573.5(T), E574(ACDFLMSW), 574.5(V), Q575(-CFHILTV), 575.5(AWY), Y576(ACFGHIMSV), 576.5(EFWY), G577(DW), 577.5(ACDEHIMNQSTV), S578(ACFHLY), 578.5(ACDEFGHILNSTVY), V579(DFGLMNQSWY), 579.5(ACDEFGILMNPQSTVWY), S580(-DEFHILMNPQTVY), 580.5(ACDEFGKLMNPQSTVWY), T581(-FGHLNPQWY), 581.5(ACDEFGILMNPQTVY), N582(-ACDEFGHIKLMPQRSTVWY), 582.5(DFGHNPSTVW), L583(-ADEFGMPSWY), 583.5(DEGIMNPQSTVY), Q584(-ADEFGHILMNPSTVWY), 584.5(ACDEFGHILMPQSTVWY), R585(-ACDFGILMNPSTVWY), 585.5(ADEFGHILMNPQSTVWY), G586(-DEHMVY), 586.5(ADEFGHILMNPQSTVY), N587(-EFHILMPTVY), 587.5(ADEFGHILMNPQSTVWY), R588(-ACDEFGHIKLMNPQSTVWY), 588.5(ADEFGHLMNPSTVY), Q589(-ADEFGINPRSTVWY), 589.5(ACDEFGHIKLMNPQSTVWY), A590(DEFHKLMNQTWY), 590.5(ACDEFGIKLMPQSTVWY), A591(-FILNPVWY), 591.5(ACDEFGHILMNPQSTVY), T592(-CDEGHLMNPQVY), 592.5(ACDEFGILMNPQSTVWY), A593(-FLMNPWY), 593.5(ACDEFGHILMNPQSTVWY), D594(ELT), 594.5(ACDEFGHILMNPQSTVWY), V595(ACDEFGHMNPQSTWY), 595.5(ACDEFGHILMNQSTVW), N596(ADEFGHIMPQTWY), 596.5(DENY), T597(FKP), 597.5(F), Q598(AEGHN), G599(SW), V600(M), 600.5(F), L601(VW), P602(CMQ), M604(CS), V605(AFN), 605.5(N), 606.5(P), D608(W), R609(D), D610(Y), 610.5(F), 613.5(Y), Q614(T), G615(S), P616(AC), I617(KM), 617.5(I), K620(ACGHMN), I621(K), H623(CDFLW), H627(MNQ), F628(L), H629(WY), P630(AGQ), 630.5(C), L633(HM), M634(C), F637(I), L639(FV), K640(ANTVW), 640.5(N), H641(CIK), Q645(LMT), I646(MT), L647(IY), N650(CILV), V653(CT), 655.5(M), N656(QW), 657.5(CHSVW), 658.5(ACEHIKNQR), T659(-CQ), 659.5(CDFGIMY), T660(-DHKMQ), 660.5(EFHIKPQWY), F661(AEILMQSTV), 661.5(ACEFGIKLMPRSVY), S662(CPW), 662.5(ACDFKMPQRVW), A663(KLNY), 663.5(CGIMNPRSVWY), A664(KWY), 664.5(ACMPRTWY), K665(CFGHM), 665.5(HILNPQRSTWY), F666(CGWY), 666.5(IV), A667(CIMY), 667.5(QY), I670(V), T671(NRS), Q672(CEGLS), S674(G), V678(C), S679(CFGHIKLRY), V680(CL), E681(DLN), E683(H), E685(L), Q687(IV), K688(HP), N690(R), E697(DI), 697.5(GHNPW), I698(DL), 699.5(E), T701(S), 701.5(A), S702(QV), 702.5(Q), N703(DG), 703.5(AEHLTY), Y704(H), 704.5(ADEILNST), N705(CDPV), 705.5(ENQY), K706(DEGRST), S707(CDEGHILMNQTVY), 707.5(MY), V708(ACEGHNRS), 708.5(I), N709(KP), 709.5(GPQ), V710(AELMNPQ), 710.5(D), D711(GN), 711.5(Q), T713(CS), T716(CIKNQRWY), N717(ERS), V719(KNQY), 720.5(N), S721(CFHIKLMNRVW), E722(DQ), P723(ACDENQSV), R724(FHKSWY), P725(ACIQ), I726(LV) | |
| 1.5(MV), A2(CS), 2.5(AGIMP), A3(CDEFILQ), 3.5(ADFILTVY), D4(ACSTV), 4.5(AFGHNVY), G5(-CN), 5.5(CFKM), 6.5(N), D9(A), W10(ACEGIKLPQRSTY), 10.5(HI), L11(ACV), 11.5(K), | 0.8-fold |

TABLE 7-continued

Amino acid alterations that reduce delivery to liver.

| Amino acid alteration | Fold increase of efficiency |
| --- | --- |
| E12(DFGHILSW), D13(CEGIKLRVWY), T14(CDFGHINPQR), L15(AHTW), E17(CFINQRSTVY), G18(ADS), I19(AEGHNQSTV), R20(FILQSV), Q21(FGHIKNRTVY), 21.5(FWY), W22(FIVY), 22.5(FILMWY), W23(CDEHKLMNQRSTV), 23.5(ACDEFGHLNQSTWY), K24(ALNPQ), 24.5(CDEHILNY), L25(AEFGHNQRST), 25.5(CEGHIKLNQRSTVWY), K26(DHNY), 26.5(HNQ), P27(T), 27.5(G), 28.5(AEFGILNPQSTVWY), P29(DEFGHILQRSTW), P30(ADFHQRSY), 30.5(ADEFGIKLNPQRSTY), P31(DHKLNY), 31.5(AFILPV), P32(AEGHIKLNQRSTY), 32.5(ADEIKLNPRSTWY), K33(-DFGNPQRSTWY), 33.5(CDEFHIKNPQTVWY), P34(-AGKLNQRTVY), 34.5(CEFGHKQRSVY), A35(EGHKLNQVY), 35.5(CEFGHINPTV), E36(CFGHKW), 36.5(DFHIKNW), R37(-DNSW), 37.5(DFMPQW), H38(-CDENVWY), 38.5(ACDEGIKNPR), K39(AFILRVWY), 39.5(CDGIY), D40(-ACGNY), 40.5(CDGSTY), D41(ACEHQRS), 41.5(CDFNRTVW), S42(-DKLQRTVWY), 42.5(ACDGKTY), R43(ASTV), 43.5(DPRV), 45.5(M), V46(I), L47(F), P48(LY), G49(CFLMQY), Y50(HW), 50.5(N), K51(ACFLMNVY), Y52(D), 53.5(R), P55(Y), 55.5(EKY), 56.5(K), G58(CES), 58.5(F), L59(ACFGKQRW), 59.5(H), D60(ACEHNQTY), K61(-ACILQRS), 61.5(GK), G62(Q), E63(HMN), V65(H), E67(CDLQW), A68(LT), A70(Y), A71(GKWY), L73(CEHKVY), E74(LQTVW), K77(CDTY), 77.5(K), A78(FNRY), 78.5(ADFHIQR), Y79(-C), 79.5(CK), D80(AMY), 80.5(F), R81(CDGQ), 81.5(FHW), Q82(-CEGHIMN), 82.5(DIK), L83(ACFGKN), 83.5(EFGHIKLQTVWY), D84(LQS), 84.5(ENQ), S85(-EPW), 85.5(AGHKSY), G86(-ACDESVW), 86.5(FGQSVW), D87(ACFGHKRY), 87.5(ADEFGQY), N88(AHLR), P89(CDH), 89.5(GL), 90.5(EMY), L91(QR), K92(GIRSV), 92.5(RY), Y93(FGHNW), 93.5(Y), N94(W), 94.5(AY), H95(ACDEGLRSY), A96(QVW), D97(-G), A98(CDWY), 98.5(CE), E99(CG), 99.5(KN), F100(KY), Q101(ADPVY), 101.5(E), E102(FLQY), R103(DINY), 103.5(SV), L104(INT), 104.5(ADEGKNV), K105(FMQRW), 105.5(CGLQRVWY), E106(CFIKY), 106.5(EFHNRVY), D107(-CFKNQTVWY), 107.5(NP), T108(-CINPY), 108.5(IQTY), S109(ACFIKLN), 109.5(AHY), F110(ACEHINY), G111(CE), 111.5(AW), G112(AP), 112.5(CQ), N113(CDGHIKLQRTVW), 113.5(FHN), L114(CFGN), G115(-DEFMPSV), 115.5(ADEHLNVW), R116(EGMP), 116.5(ADEGHIKLPQRSTVWY), A117(CEHKQRWY), 117.5(DEFKLPQW), V118(-DKLPRWY), 118.5(ACEGMP), F119(ACHLQSVWY), 119.5(AHIKLNQRSTVY), Q120(-CFIKRW), 120.5(GKLPR), A121(-EFGHKNQW), 121.5(FGHQR), K122(-DFGNRW), 122.5(ADFHIKPQSW), K123(CDEFHQSTY), 123.5(AFKNPQT), R124(-CGHIPY), 124.5(CEFHKPRS), V125(-ACDEHNPQSW), 125.5(ACEFGQRSW), L126(-CEKQRWY), 126.5(CERS), E127(-HIMPWY), 127.5(ADGILNSTY), P128(ACDFILQRSTV), 128.5(AGHKLRSTW), L129(CDGKRWY), 129.5(CDFGQRY), G130(CEFQ), 130.5(CDEHKLQRSTY), L131(DIQVY), 131.5(ACDEFHLPW), V132(-CDRS), 132.5(EHIKLNPRVWY), E133(-GHLS), 133.5(GIPW), E134(-W), 134.5(EHIQW), P135(CDHY), 135.5(DELNPRWY), V136(-DHQY), 136.5(ACEHILMNPQRTVY), K137(-CDHLPRSTWY), 137.5(ACDEGHIKLNPQRSTVWY), T138(AEGHKNPQR), 138.5(CDEFGKNQSTW), A139(-CDEFIKLPQSTWY), 139.5(ACDGHNRVY), P140(ADEFGHKTW), 140.5(CDEKNQRV), G141(-CDEFHIKLMNQRSTVWY), 141.5(DEFHIKLQRTVY), K142(-ACDEFGINPSY), 142.5(ACDEFGHIKNPQSTVWY), K143(EGIRSVY), 143.5(AEFKLPQRSTWY), R144(AHNPSTVW), 144.5(ACEFGHIKLNPQRSTVWY), P145(-ADEFGIKLNRSTVWY), 145.5(DEGKMNPQRSTVW), V146(-ACDEKLNQRTWY), 146.5(ACEFHIKLNPQRVY), E147(AFGHKLNQTVY), 147.5(EFHIKRS), H148(CGRTW), 148.5(AHKMNPQR), S149(-ACEGHIMNPQRW), 149.5(ACGHIKLMNRSTW), P150(DFHMQR), 150.5(CDEKLMNPQRTVWY), V151(-CDGKWY), 151.5(DWY), E152(CFNPV), 152.5(DGHKNRY), D154(S), 155.5(D), S156(AT), S157(EFKRTV), 157.5(DNQTW), G158(D), 158.5(P), T159(DEFGHPQR), 159.5(Y), G160(CY), 160.5(DFHNWY), K161(-GHLNQSTVY), 161.5(ADFGILQRSTVW), A162(DIKQ), 162.5(ACENPQRST), G163(-CFHKNRV), 163.5(DEKLNPRSTVWY), Q164(CHIMRVW), 164.5(DEFGIKNPQRSY), Q165(CHILNPVW), 165.5(FIPQTV), P166(-ACFGHIKLNQRSTY), 166.5(FGHINPSTY), A167(QSV), R168(K), R170(K), L171(I), N172(-ACDFHLQSVW), 172.5(F), 173.5(ADEFGHINQWY), G174(ACDEFHQSTWY), 174.5(AEFHIKNRSY), Q175(-ACDGNRST), 175.5(AFGIKLNQY), T176(ACDFGY), 176.5(ADENP), G177(-EQ), 177.5(EGIT), D178(-EISWY), 178.5(FINPRS), A179(-IKPSW), 179.5(CDHKNPQRSTVWY), D180(-ACFIMNQVY), 180.5(ACFHILMQR), S181(FKLTY), 181.5(ACGHNSTVY), V182(ACIS), 182.5(CHLPRS), P183(CHRS), | |

TABLE 7-continued

| Amino acid alterations that reduce delivery to liver. | |
|---|---|
| Amino acid alteration | Fold increase of efficiency |
| 183.5(EGKMNQY), D184(CFGHINPQRTY), 184.5(CLMPRY), P185(CDEFGILNTVWY), 185.5(CFILPQTVW), Q186(FIKNPTY), 186.5(CDEIKNSY), P187(-FGILNQS), 187.5(CEGKNPQWY), L188(CEFIMQSTW), 188.5(ADNQ), G189(-CIMN), 189.5(FLMQW), Q190(CMNRW), 190.5(ACFGHQR), P191(KN), 191.5(CIQVW), P192 (-CDFKMSWY), 192.5(EGHLMVY), A193(CDGHILNY), 193.5(DHIMRTVW), A194(CFGIQVW), 194.5(CFKMPT), P195(DEGHKQRSTVY), 195.5(CDHMQST), S196(-FKNPRT), G197(A), L198(ACDFVWY), G199(D), 199.5(FHRW), T200(ACFGINQR), N201(CDH), T202(KPQRSV), M203(ACDEFGHILPQRTVWY), A204(DV), T205(FKMRVWY), G206(ACDEFHKQRY), S207(ACDRY), G208(AEFHKLNQRWY), A209(DEKMRSY), P210(CGHR), D213(ACFGHIKLNTW), N214(ACDEFKLPSVY), N215(CHILY), E216(ADH), G217(ACDEFHILMNSTVY), A218(QST), G220(ACMNT), V221(I), N223(ACDHIMQSTY), S225(CQR), H229(ADSTV), D231(C), T233(DHIMQSVY), M235(LV), 236.5(D), D237(C), 237.5(DEHKNQ), R238(CHS), 238.5(CFTY), I240(H), T242(CFHRY), S243(A), T246(I), L249(C), P250(AQS), T251(CLSV), N253(D), N254(CQS), H255(A), L256(ACGKMQRSV), K258(LQ), Q259(AGHKPRS), 260.5(MQ), S261(ACGNT), 262.5(D), Q263(-DEFGHLTWY), S264(-ADEILQTVWY), 264.5(D), 265.5(ADEMNQST), A266(S), 266.5(AE), S267(AENP), 267.5(E), N268(ADEQ), 268.5(E), 269.5(D), N270(ACDGHQSY), H271(EFINV), F273(HWY), S276(K), G280(A), Y281(H), F282(LWY), F284(CY), F287(Y), H288(N), S292(C), D295(AE), N303(TV), F306(W), R307(-CDKMSTY), 307.5(FKN), P308(-NV), K309(AQS), R310(AGILVW), L311(CFY), N312(DHLMQTWY), K314(CFGHLMQSTVWY), L315(V), I318(F), T324(LMN), 324.5(CKR), Q325(CHKRV), 325.5(FGHIKRST), N326(CDMRWY), 326.5(N), D327(QT), 327.5(GHT), G328(AN), 328.5(G), T329(ACIY), T330(KQS), T331(FHY), I332(ACS), 332.5(K), A333(DFHNTY), N334(S), L336(I), T339(C), V342(ACIM), T344(DFIKLMNV), S346(CFHLMPQW), Y348(FNRS), Q349(AGMS), V353(CI), L354(QT), G355(S), S356(A), H358(ACGNST), Q359(DEHM), C361(A), F365(W), A367(CP), V369(PT), M371(CIKLNQS), V372(CI), Y375(W), G376(CS), Y377(F), L378(ACV), T379(ACGSV), 379.5(DE), L380(CEMNQTVY), 380.5(E), N381(ACDGMQS), N382(CDEST), 382.5(D), 383.5(E), S384(AG), 384.5(D), Q385(ACEIKLMRSTVY), 385.5(DEKLPT), A386 (-EHLNPRSTVW), 386.5(CDEY), V387(CDEQTWY), 387.5(EGKP), G388(EIM), R389(GIL), S390(ADGNT), 390.5(C), S391(A), C394(V), 394.5(N), 395.5(W), Y397(AGN), P399(EIMQRS), Q401(ACDEFIKLNRVWY), L403(C), R404(K), 404.5(N), T405(SY), G406(DENQ), 406.5(Q), 407.5(H), N408(ADFGHLMQSTWY), 408.5(CN), F409(CHW), T410(CEFHLMQVY), F411(CLTVW), S412(FGIKMVWY), 412.5(Q), Y413(FM), T414(EFIKLNQ), 414.5(D), 415.5(AGNPQS), E416(ADG), 416.5(CEKMNR), D417(AIKMNTV), 417.5(DEKLMQRS), V418(GMQS), P419(EIKNSTVW), F420(LM), S422(A), S423(CLT), Y424(FHT), A425(-CFQV), H426(N), S427(AN), Q428(EHN), S429(CGHPY), L430(MV), D431(M), 431.5(Y), R432(-I), L433(IV), 433.5(F), M434(A), L437(ANSV), I438(GHM), D439(KNPSTY), 441.5(M), L442(ITV), 444.5(CLM), L445(CFIMY), 445.5(ACDEGHILMNQSTVY), S446(-DEGHILMNQTV), 446.5(ACDEFGHILMNPQSTVWY), R447 (-ACDEFGHILMNPQSTVWY), 447.5(ACDEFGHILMNPQSVWY), T448 (-ACDEFGHILMNPQSVWY), 448.5(ACDEFGHILMNPQSY), N449 (-CDEFHILMPTVWY), 449.5(AEGHLMNPST), T450(-CFGNPSY), 450.5(ADEFGHLQTV), P451(-IL), 451.5(NP), S452(-DEFGLNPQTY), 452.5(ALV), G453(-AEFHIKLMNPQST), 453.5(FILNY), T454 (-DEFGHILMNPSV), 454.5(ADEFGMPY), T455(-ADEILMNPQSVY), 455.5(FHNPQ), T456(DEFGHIKLMNQSY), 456.5(DEGHILPS), Q457(EGHILMPS), 457.5(ADEFGHLMNPTWY), S458(-DEFHMNVW), 458.5(CDEGHILMNTVW), R459(-DEGINPY), 459.5(DEP), L460(AHIMPTWY), 460.5(W), Q461(DFHIKMV), F462(Y), 462.5(N), S463(ACDGKMNQRTV), 463.5(F), Q464(IKLMRTV), 464.5(SY), A465(G), G466(AD), 466.5(E), A467(EMS), S468(ACDEHLNPQVWY), D469(V), 469.5(E), R471(DEGQSTV), D472(GHLMQSTVWY), Q473(FHSY), S474(ACIY), R475(HK), 475.5(SW), N476(CSTW), 476.5(L), W477(F), 477.5(L), L478(FI), 478.5(L), P479(GIT), 479.5(D), G480(Y), P481(ACV), 481.5(GHY), C482(AFGQSWY), 482.5(F), Y483(AHITVW), 483.5(FHQV), R484(EFGHIKLMNQSTVY), 484.5(N), Q485(ACFGILNSTY), 485.5(EIKMY), Q486(ACDEFGILMPSVWY), 486.5(FV), R487(-ACDEFGHIKLMNPQSTVWY), 487.5(FW), V488(ACEFGHILMNQTWY), 488.5(ACDEFGILMPQSVWY), S489 (-ACEFGHIKLMNPQTVWY), 489.5(ACDEGLMPQRSTVWY), K490 (-ACDEFGHILMNPQRSTVWY), 490.5(ACDEFGHILMPQRSTVWY), T491(-AGPSY), 491.5(ADEFGHILMNPQSTVWY), S492 (-CFGHLMPQTV), 492.5(ADEGHILMPQSTVY), A493(-HQTV), | |

TABLE 7-continued

Amino acid alterations that reduce delivery to liver.

| Amino acid alteration | Fold increase of efficiency |
| --- | --- |
| 493.5(ADEFGHIKLMNPQSTVY), D494(EFR), 494.5(ADEFGHILMNPQSTVWY), N495(-ADEFGHILMPQSTVWY), 495.5(ACDEFGILMNPQSTVWY), N496(-ACDEFGILMPQTVWY), 496.5(ADEFGHILMNPQSTVWY), N497(-CEFGHLMVWY), 497.5(ADEFGILMNPQSTVY), S498(-CDEINPQRTVW), 498.5(ADEFGHILMNPQSTVWY), E499(CIPS), 499.5(ACDEGILMNPQRSTVWY), Y500(-ACDEGHIKLNPQSTVW), 500.5(ADEFGHILMNPQSTVWY), S501(-CDEFGILMNPRTVWY), 501.5(ACDEFGHILMNPQRSTVWY), W502(-ACDEFGILMPQSTVY), 502.5(ADEFGHILMNPQSTVWY), T503(-ADEFGHLMNPQSWY), 503.5(ADEFGILMNPQSTVW), G504(-ACDEFHILMNPQSTVWY), 504.5(ACDEFGHILMNPQSTVWY), A505(-CDEFGHILMNPQSTVWY), 505.5(ACDEFGILMPQSTVWY), T506(-FGILMNPQS), 506.5(ACIPSTVW), K507(-ACEFHLMNVWY), Y508(-DIMSTV), H509(EFKNQR), 509.5(K), L510(I), 510.5(K), N511(ACDEGLMQSWY), 512.5(S), R513(HI), D514(ACFGILMQSTV), S515(ACINTV), L516(ACIMRS), V517(CL), 517.5(C), N518(AILQTVY), P521(CFMS), 521.5(M), A522(CSV), M523(CLV), 523.5(A), A524(GP), 524.5(ACGHSTW), S525(CMNPT), 525.5(ACDEFGHILMNPQSTVWY), H526(-DEFGIKLMPRVWY), 526.5(ACDEFGHILMNPQSTVWY), K527 (-DEFGHILPSTVWY), 527.5(ACDEFGHILMPQSTVWY), D528(AEFMPQSVW), 528.5(DEPT), D529(ES), 529.5(ADEGLMNPQTV), E530(DNPVW), 530.5(ACDEFGHIKLMNQRSTVWY), E531(ACFGHILMNPQSTVY), 531.5(ADEFGIKLMNPQRSTVY), K532 (-ACDEPR), 532.5(ACDEFGHIKLMNPQSTVWY), F533(ACDEGHILNQSTVW), 533.5(ACDEFGHILNPQSTVWY), F534(ILMVWY), 534.5(F), P535(-AF), Q536(-ACDEFGHIMNPSTVWY), 536.5(ACILTV), S537(-ADFGNQTY), 537.5(T), G538(-), V539(AHLMNQST), L540(IM), 540.5(KN), I541(-DEPQRT), 541.5(ACDEMQRV), F542(P), 542.5(QY), G543(APS), 543.5(DHIKLMPQRSTV), K544(-AFST), 544.5(AEFGHIKLMNRVWY), Q545(-ADGHKLNRWY), 545.5(ACEFHILMNPQSTVWY), G546(ACEFHLNPQSTVWY), 546.5(ACDEFGHILMNQSTVWY), S547 (-CDFGHLNQVWY), 547.5(ACDGHILMNPQSTVWY), E548(ADFGLMNPS), 548.5(ACDFGHILNPSTWY), K549 (-DEFGHLPQSY), 549.5(ADFGLMNQSTVY), T550(-CQWY), 550.5(AEGIKMNPQRSTV), N551(-ACEFGIKPQRSTV), 551.5(ACDEFILMPQST), V552(CQST), 552.5(VW), D553(AEGST), I554(ACHQSTW), E555(AGHNSTVY), K556(CDMQ), 556.5(Q), V557(IL), M558(HIV), I559(FQV), T560(V), D561(INRVY), E562(D), E563(R), I565(T), 565.5(Y), R566(DFHLQY), T567(P), 567.5(E), T568(P), 569.5(M), P570(QS), 570.5(M), V571(ADEFHILMQSTY), A572(CGY), 572.5(WY), T573(ACDGHINSVWY), 573.5(T), E574(ACDFLMSW), 574.5(V), Q575(-CFHILMSTV), 575.5(AWY), Y576(ACFGHIMSV), 576.5(EFWY), G577(DW), 577.5(ACDEHIMNQSTV), S578(ACFHLNVY), 578.5(ACDEFGHILNSTVY), V579(DFGILMNQSWY), 579.5(ACDEFGILMNPQSTVWY), S580(-CDEFGHILMNPQTVY), 580.5(ACDEFGIKLMNPQSTVWY), T581(-AFGHLNPQWY), 581.5(ACDEFGILMNPQTVWY), N582(-ACDEFGHIKLMPQRSTVWY), 582.5(DFGHNPSTVW), L583(-ADEFGMPSTWY), 583.5(DEGIMNPQSTVY), Q584(-ADEFGHILMNPSTVWY), 584.5(ACDEFGHILMPQSTVWY), R585(-ACDFGHIKLMNPSTVWY), 585.5(ADEFGHILMNPQSTVWY), G586(-DEHMVY), 586.5(ADEFGHILMNPQSTVY), N587(-DEFHILMPQTVY), 587.5(ADEFGHILMNPQSTVWY), R588(-ACDEFGHIKLMNPQSTVWY), 588.5(ADEFGHILMNPQSTVY), Q589(-ADEFGINPRSTVWY), 589.5(ACDEFGHIKLMNPQSTVWY), A590(DEFHKLMNQTWY), 590.5(ACDEFGIKLMPQSTVWY), A591(-FGILNPVWY), 591.5(ACDEFGHILMNPQSTVY), T592(-CDEGHLMNPQVY), 592.5(ACDEFGILMNPQSTVWY), A593(-CFLMNPWY), 593.5(ACDEFGHILMNPQSTVWY), D594(ELT), 594.5(ACDEFGHILMNPQSTVWY), V595(ACDEFGHIMNPQSTWY), 595.5(ACDEFGHILMNQSTVW), N596(ADEFGHIMPQSTWY), 596.5(DENY), T597(EFKPR), 597.5(F), Q598(AEGHNSY), G599(SW), V600(LM), 600.5(F), L601(VWY), P602(CMQ), G603(A), M604(CS), V605(ACFMNT), 605.5(N), 606.5(P), D608(ENW), R609(D), D610(Y), 610.5(F), Y612(R), 613.5(Y), Q614(NT), G615(S), P616(AC), I617(KM), 617.5(I), K620(ACGHMN), I621(K), H623(CDFKLSVW), G626(A), H627(AFILMNQW), F628(L), H629(WY), P630(ACGQT), 630.5(C), S631(N), L633(HMY), M634(C), F637(I), L639(FVY), K640(ANRTVWY), 640.5(N), H641(CIK), Q645(LMT), I646(CMT), L647(IY), I648(C), N650(CILTV), P652(A), V653(CT), A655(S), 655.5(MV), N656(QW), 657.5(CDHLSVW), S658(FIMN), 658.5(ACEHIKLNQRWY), T659 (-CEQR), 659.5(ACDEFGIMNSVY), T660(-CDEHKMPQR), 660.5(ADEFHIKLPQWY), F661(AEILMQSTV), | |

TABLE 7-continued

| Amino acid alterations that reduce delivery to liver. | |
|---|---|
| Amino acid alteration | Fold increase of efficiency |
| 661.5(ACDEFGIKLMPRSVY), S662(CPRW), 662.5(ACDFHIKLMPQRSTVW), A663(IKLMNPY), 663.5(CDGILMNPRSTVWY), A664(DHKNRWY), 664.5(ACHLMPRTVWY), K665(ACFGHIMNQRW), 665.5(AHILNPQRSTWY), F666(CGSWY), 666.5(IPV), A667(CILMRY), 667.5(QY), S668(A), F669(Y), I670(V), T671(NRS), Q672(CEGLS), S674(G), T675(S), V678(C), S679(CEFGHIKLRY), V680(CL), E681(DLNST), I682(M), E683(H), E685(ALQT), L686(T), Q687(IMVW), K688(HP), N690(R), E697(-DHIM), 697.5(GHNPQW), I698(-DL), 699.5(E), T701(S), 701.5(A), S702(IQV), 702.5(Q), N703(DG), 703.5(AEHLTY), Y704(H), 704.5(ADEILNST), N705(CDEHILPTV), 705.5(ENQY), K706(DEGRST), S707(CDEGHILMNQTVY), 707.5(MY), V708(ACEGHNRS), 708.5(I), N709(CDKLPQR), 709.5(CGPQ), V710(AELMNPQ), 710.5(D), D711(GNP), 711.5(QY), T713(CS), T716(CFIKNQRVWY), N717(AEFHRSY), V719(KNQRY), 720.5(N), S721(CFHIKLMNQRTVWY), E722(DQ), P723(ACDEHNQSTV), R724(FHKSWY), P725(ACIQV), I726(LV), R733(K), N734(V), L735(C) | |
| 1.5(AGMV), A2(CS), 2.5(AGIMP), A3(-CDEFILQSY), 3.5(ACDFILMTVY), D4(ACHNSTVWY), 4.5(AFGHNVY), G5(-ACN), 5.5(CFKM), Y6(FI), 6.5(N), L7(F), D9(AV), W10(ACEGIKLPQRSTY), 10.5(HI), L11(ACFIV), 11.5(K), E12(DFGHILNQSWY), D13(CEGIKLNRVWY), T14(CDFGHINPQRSV), L15(AFHTW), S16(G), E17(ACFINQRSTVY), G18(ADS), I19(AEFGHNQSTV), R20(EFHILQSV), Q21(FGHIKNRSTVY), 21.5(FWY), W22(FIVY), 22.5(FILMWY), W23(CDEFGHKLMNQRSTVY), 23.5(ACDEFGHLNQSTWY), K24(ALNPQV), 24.5(CDEHILNY), L25(AEFGHNQRSTV), 25.5(CEGHIKLNQRSTVWY), K26(DHNY), 26.5(HKNQ), P27(T), 27.5(G), 28.5(AEFGILNPQSTVWY), P29(ACDEFGHILQRSTVW), P30(ADFHQRSTY), 30.5(ADEFGIKLNPQRSTY), P31(DFGHIKLNRSY), 31.5(AFILPVY), P32(AEGHIKLNQRSTY), 32.5(ADEFHIKLNPRSTVWY), K33(-ADFGNPQRSTWY), 33.5(CDEFHIKNPQTVWY), P34(-AEFGHKLNQRTVWY), 34.5(CEFGHKPQRSTVWY), A35(EGHKLNQVY), 35.5(CEFGHINPQTVY), E36(-CFGHKNTVW), 36.5(DFHIKLNRSW), R37(-DEGNSVW), 37.5(CDEFIMPQRSW), H38(-ACDELNRVWY), 38.5(ACDEGIKNPRSV), K39(AEFILMRTVWY), 39.5(CDGHINSWY), D40(-ACGLNY), 40.5(CDGQSTY), D41(ACEHQRS), 41.5(CDFNRSTVW), S42(-DKLQRTVWY), 42.5(ACDGKTWY), R43(ASTVY), 43.5(DPRSV), 45.5(M), V46(I), L47(F), P48(LY), G49(CFLMQWY), Y50(HW), 50.5(N), K51(ACFLMNQVY), Y52(D), 53.5(R), P55(Y), 55.5(EKY), 56.5(K), G58(CES), 58.5(F), L59(ACFGKQRW), 59.5(H), D60(ACEHNQSTY), K61(-ACILQRSV), 61.5(GK), G62(QS), E63(ADFHMNV), V65(CFH), N66(AG), E67(ACDLPQRVW), A68(CILPST), A70(CFLY), A71(FGKLNTVWY), L73(CEHKNVY), E74(ACLQTVW), K77(CDSTWY), 77.5(K), A78(FKNRSY), 78.5(ADFHIQR), Y79(-C), 79.5(CK), D80(AHMQTY), 80.5(F), R81(ACDGLQW), 81.5(FHILW), Q82(-CEFGHIMNRTW), 82.5(DFIKLW), L83(ACFGKNQW), 83.5(EFGHIKLQRSTVWY), D84(HILQSV), 84.5(AENQ), S85(-CEKLPWY), 85.5(AFGHKSY), G86 (-ACDEHLSVWY), 86.5(FGQSVW), D87(ACFGHKNRSY), 87.5(ADEFGQSWY), N88(ADHLR), P89(ACDH), 89.5(GL), 90.5(EMY), L91(GQRS), K92(AFGINQRSTV), 92.5(RY), Y93(FGHNW), 93.5(Y), N94(-STW), 94.5(AY), H95(ACDEGLRSY), 95.5(W), A96(GQVW), D97 (-G), A98(CDIKNWY), 98.5(CE), E99(CFGNSTY), 99.5(FKN), F100(KY), Q101(ADEPVY), 101.5(E), E102(FILQSY), R103(CDGINY), 103.5(ASV), L104(CINT), 104.5(ADEFGIKNSTVW), K105(EFMQRW), 105.5(CFGLQRSVWY), E106(CFGIKNQSTWY), 106.5(EFHINRTVY), D107(-CFKNQTVWY), 107.5(KNPQSW), T108(-CFINPQY), 108.5(AEFGHIQSTY), S109(ACDEFIKLNY), 109.5(AGHNY), F110(ACEHINPY), G111(CE), 111.5(AW), G112(APT), 112.5(CQ), N113(CDFGHIKLQRTVW), 113.5(FHN), L114(ACEFGHN), G115 (-ACDEFMPRSV), 115.5(ADEHLMNVW), R116(EGHLMP), 116.5(ADEGHIKLPQRSTVWY), A117(-CEHKQRWY), 117.5(CDEFKLPQW), V118(-DHIKLPRWY), 118.5(ACEGMP), F119(ACHLQSVWY), 119.5(AHIKLNQRSTVY), Q120(-CFIKLRSTW), 120.5(GIKLPR), A121(-EFGHIKNQTVW), 121.5(FGHQR), K122 (-ADEFGNRW), 122.5(ADFHIKLPQSTW), K123(CDEFHQSTVWY), 123.5(AFKNPQT), R124(-CFGHIPTWY), 124.5(CEFHKPRSV), V125 (-ACDEFHNPQSWY), 125.5(ACEFGQRSW), L126(-CDEFKQRWY), 126.5(CEGRS), E127(-CDHIMPWY), 127.5(ADGILNSTVY), P128(ACDFILQRSTV), 128.5(AGHKLMRSTW), L129(-CDFGKNRSWY), 129.5(ACDFGQRY), G130(CEFQ), 130.5(CDEHKLQRSTY), L131(DEGHIPQTVY), 131.5(ACDEFHLPRW), V132(-CDRSWY), 132.5(EFHIKLNPRVWY), E133(-ADGHLNST), 133.5(EGIPSW), E134 (-ADILPW), 134.5(EHINQRW), P135(CDFHKSTWY), | 0.9-fold |

TABLE 7-continued

| Amino acid alterations that reduce delivery to liver. | |
|---|---|
| Amino acid alteration | Fold increase of efficiency |
| 135.5(CDELNPRSTWY), V136(-DEFGHIKQSTWY), 136.5(ACEGHIKLMNPQRSTVWY), K137(-ACDEHLPRSTWY), 137.5(ACDEFGHIKLNPQRSTVWY), T138(-ADEFGHKNPQRW), 138.5(CDEFGHIKNPQRSTVWY), A139(-CDEFGIKLPQRSTWY), 139.5(ACDEGHLNRVY), P140(-ACDEFGHKRSTVWY), 140.5(ACDEHIKNQRVWY), G141(-CDEFHIKLMNQRSTVWY), 141.5(DEFHIKLQRTVY), K142(-ACDEFGILNPQSY), 142.5(ACDEFGHIKLNPQRSTVWY), K143(-EGIRSVY), 143.5(AEFKLPQRSTWY), R144(AHNPSTVW), 144.5(ACEFGHIKLNPQRSTVWY), P145(-ACDEFGHIKLNQRSTVWY), 145.5(DEGIKMNPQRSTVWY), V146(-ACDEFGKLNQRTWY), 146.5(ACEFHIKLNPQRSVY), E147(-ADFGHKLNQTVY), 147.5(ACDEFGHIKRSVW), H148(-ACEGKRTVW), 148.5(AGHKMNPQRTVW), S149(-ACEGHIMNPQRVW), 149.5(ACGHIKLMNPRSTW), P150(CDFHMNQRSVY), 150.5(CDEKLMNPQRSTVWY), V151(-CDGKRSWY), 151.5(DIRWY), E152(ACFHIKLNPQVW), 152.5(DGHKMNQRY), P153(ISV), 153.5(AP), D154(S), 155.5(D), S156(AGT), S157(AEFGKQRTVW), 157.5(DNQTW), G158(D), 158.5(GP), T159(DEFGHIPQR), 159.5(PY), G160(CY), 160.5(CDFHNSWY), K161(-GHLNQSTVWY), 161.5(ADFGILQRSTVW), A162(DIKLPQW), 162.5(ACELNPQRST), G163(-CDFHKNPRTV), 163.5(DEGHIKLNPRSTVWY), Q164(CDHIMRTVW), 164.5(ADEFGIKNPQRSY), Q165(ACHILNPSVW), 165.5(FIPQTV), P166(-ACFGHIKLNQRSTVY), 166.5(FGHINPSTY), A167(QSV), R168(K), R170(K), L171(I), N172(-ACDFHKLQSVWY), 172.5(F), 173.5(ADEFGHINQWY), G174(ACDEFHQSTWY), 174.5(ACEFHIKNQRSY), Q175(-ACDGHKNRST), 175.5(ACDFGIKLNQRSY), T176(ACDFGRY), 176.5(ADENP), G177 (-EQ), 177.5(CEGILPTY), D178(-AEIRSWY), 178.5(DFINPRSW), A179 (-CEFIKPSW), 179.5(ACDEFGHKNPQRSTVWY), D180(-ACFHIMNQVY), 180.5(ACDFGHILMQRSV), S181(FKLNRTY), 181.5(ACGHNSTVY), V182(ACINPRS), 182.5(CHLPRS), P183(CHLRS), 183.5(CDEGKLMNQY), D184(ACFGHILNPQRTWY), 184.5(CLMPRVY), P185(CDEFGILNSTVWY), 185.5(CEFILPQTVW), Q186(-FGIKNPSTY), 186.5(CDEIKNQSY), P187(-ADFGILNQRST), 187.5(CEGKNPQRWY), L188(CDEFIMPQSTW), 188.5(ADIKLNQSV), G189(-CEIKMNRV), 189.5(EFGLMQRW), Q190(-ACGLMNRSVW), 190.5(ACDFGHPQRSY), P191(AHIKLMNVWY), 191.5(CFIPQRTVW), P192 (-ACDFKLMQRSTWY), 192.5(EGHKLMNSVY), A193(CDGHIKLMNPQY), 193.5(DHIMPRSTVW), A194(CFGHIKMQVW), 194.5(CFKMNPT), P195(DEGHKQRSTVY), 195.5(CDHMPQRST), S196(-DFGKNPQRTW), G197(AS), L198(ACDFGNRVWY), G199(D), 199.5(CFHRW), T200(ACFGINQRS), N201(CDH), T202(KPQRSVWY), M203(ACDEFGHIKLPQRSTVWY), A204(DV), T205(EFIKMRVWY), G206(ACDEFHKQRSY), S207(ACDGHRY), G208(ADEFHKLNQRVWY), A209(DEGHKMNQRSVY), P210(CGHQR), M211(LV), A212(G), D213(ACEFGHIKLNPSTW), N214(ACDEFIKLPSVY), N215(CDHILY), E216(ADH), G217(ACDEFHILMNQSTVY), A218(QST), G220(ACMNST), V221(I), N223(ACDHIMQSTY), S225(CQR), H229(ACDSTV), D231(C), T233(DHIMQSVY), M235(LV), 236.5(D), D237(CGH), 237.5(DEGHKNQ), R238(CHS), 238.5(CFTY), I240(FHV), T242(CFHRSY), S243(A), T244(C), T246(IV), A248(S), L249(CV), P250(AQS), T251(CLPSV), Y252(F), N253(D), N254(CGQS), H255(A), L256(ACGHKMNQRSV), K258(LQ), Q259(AGHKPRS), 260.5(MNQ), S261(ACGNT), S262(T), 262.5(D), Q263(-DEFGHLTWY), S264(-ADEHILMQTVWY), 264.5(D), 265.5(ADEMNQST), A266(S), 266.5(AE), S267(AENPT), 267.5(E), N268(ADEQ), 268.5(E), 269.5(D), N270(ACDGHQSY), H271(EFINV), F273(HWY), S276(AK), G280(A), Y281(FH), F282(LMVWY), F284(CY), F287(Y), H288(N), C289(S), S292(C), D295(AE), N303(TV), F306(W), R307(-CDIKMSTY), 307.5(FKN), P308(-NV), K309(ACQS), R310(ACFGIKLNSTVW), L311(CFIY), N312(CDHLMQTWY), F313(V), K314(CFGHLMNQRSTVWY), L315(V), I318(FL), 323.5(CT), T324(AHLMN), 324.5(CFKMRT), Q325(CHKRV), 325.5(ACFGHIKRST), N326(CDGLMRTWY), 326.5(N), D327(AGQT), 327.5(AGHT), G328(AN), 328.5(G), T329(ACFIY), T330(KNQS), T331(FHNY), I332(ACSV), 332.5(K), A333(CDFHNSTY), N334(QS), L336(I), T339(C), V342(ACIM), F343(M), T344(CDEFIKLMNRSV), S346(ACEFHIKLMPQVWY), Y348(AEFGHNRSW), Q349(AGMS), V353(CIT), L354(AIMQTVY), G355(S), S356(A), H358(ACGLNQST), Q359(DEHKMTV), C361(A), L362(I), F365(W), A367(CP), V369(CIPT), F370(Y), M371(ACIKLNQSTV), V372(CI), Y375(FW), G376(CS), Y377(F), L378(ACV), T379(ACGSV), 379.5(DE), L380(CEMNQTVY), 380.5(E), N381(ACDGMQS), N382(CDEST), 382.5(D), 383.5(E), S384(AG), 384.5(D), Q385(ACDEIKLMRSTVY), 385.5(ADEHKLPT), A386 | |

TABLE 7-continued

| Amino acid alteration | Fold increase of efficiency |
| --- | --- |
| Amino acid alterations that reduce delivery to liver. | |
| (-EGHLNPRSTVWY), 386.5(CDEPY), V387(CDEIQTWY), 387.5(EGKP), G388(EIM), R389(GIL), S390(ADGNT), 390.5(C), S391(AG), Y393(F), C394(V), 394.5(N), 395.5(W), Y397(AGN), P399(EIMQRS), Q401(ACDEFIKLMNRSVWY), L403(C), R404(K), 404.5(N), T405(SY), G406(DENQ), 406.5(Q), 407.5(H), N408(ADFGHLMQSTWY), 408.5(CMN), F409(CHW), T410(CEFGHLMQVY), F411(ACLTVW), S412(EFGIKMNQTVWY), 412.5(Q), Y413(FM), T414(EFGIKLMNQ), 414.5(D), 415.5(ADGNPQS), E416(ADG), 416.5(CEGKMNRS), D417(AEGIKMNSTV), 417.5(DEKLMQRS), V418(CGHLMQS), P419(DEGIKLNRSTVW), F420(LM), S422(A), S423(CLT), Y424(FHT), A425(-CFQSV), H426(N), S427(ANT), Q428(EHNS), S429(CGHPY), L430(MV), D431(M), 431.5(Y), R432(-I), L433(IMSV), 433.5(F), M434(A), L437(ANSV), I438(GHMT), D439(KNPSTY), 441.5(M), L442(ITV), 444.5(CLM), L445(CFIMVY), 445.5(ACDEGHILMNQSTVY), S446 (-CDEGHILMNQTV), 446.5(ACDEFGHILMNPQSTVWY), R447 (-ACDEFGHILMNPQSTVWY), 447.5(ACDEFGHILMNPQSVWY), T448 (-ACDEFGHILMNPQSVWY), 448.5(ACDEFGHILMNPQSY), N449 (-ACDEFGHILMPTVWY), 449.5(AEGHLMNPST), T450 (-ACDFGLMNPSY), 450.5(ADEFGHLPQSTV), P451(-IL), 451.5(GNP), S452(-DEFGILNPQTY), 452.5(ALV), G453(-AEFHIKLMNPQST), 453.5(FILMNY), T454(-ADEFGHILMNPQSV), 454.5(ADEFGLMPY), T455(-ADEILMNPQSVY), 455.5(FHNPQ), T456(ADEFGHIKLMNPQSY), 456.5(DEGHILPS), Q457(EFGHILMPS), 457.5(ADEFGHILMNPTWY), S458(-DEFHMNVW), 458.5(CDEGHILMNQSTVW), R459(-DEGINPY), 459.5(DEP), L460(AHIMPTWY), 460.5(W), Q461(DEFHIKMSTV), F462(Y), 462.5(N), S463(ACDGKMNQRTV), 463.5(F), Q464(CIKLMRTV), 464.5(SY), A465(G), G466(AD), 466.5(E), A467(EKMS), S468(ACDEFHLNPQVWY), D469(V), 469.5(E), R471(DEGQSTV), D472(GHLMQSTVWY), Q473(FHSY), S474(ACIY), R475(HK), 475.5(SW), N476(CSTW), 476.5(L), W477(FY), 477.5(L), L478(FI), 478.5(L), P479(GIT), 479.5(D), G480(Y), P481(ACV), 481.5(GHY), C482(AFGHNQSWY), 482.5(F), Y483(ACHITVW), 483.5(FHQV), R484(EFGHIKLMNQSTVY), 484.5(N), Q485(ACFGILMNSTY), 485.5(EIKMQY), Q486(ACDEFGILMPSVWY), 486.5(FV), R487(-ACDEFGHIKLMNPQSTVWY), 487.5(FW), V488(ACEFGHILMNQTWY), 488.5(ACDEFGILMPQSVWY), S489 (-ACEFGHIKLMNPQTVWY), 489.5(ACDEGLMPQRSTVWY), K490 (-ACDEFGHILMNPQRSTVWY), 490.5(ACDEFGHILMPQRSTVWY), T491(-AGMPQSY), 491.5(ADEFGHIKLMNPQSTVWY), S492 (-CDFGHLMPQTV), 492.5(ADEGHILMPQSTVY), A493(-HLQRSTV), 493.5(ADEFGHIKLMNPQSTVWY), D494(EFR), 494.5(ADEFGHILMNPQSTVWY), N495(-ADEFGHILMPQSTVWY), 495.5(ACDEFGILMNPQSTVWY), N496(-ACDEFGILMPQTVWY), 496.5(ADEFGHILMNPQSTVWY), N497(-CEFGHLMSTVWY), 497.5(ADEFGILMNPQSTVY), S498(-CDEGINPQRTVW), 498.5(ADEFGHILMNPQSTVWY), E499(CIPS), 499.5(ACDEGHILMNPQRSTVWY), Y500(-ACDEGHIKLMNPQSTVW), 500.5(ADEFGHILMNPQSTVWY), S501(-ACDEFGHILMNPRTVWY), 501.5(ACDEFGHILMNPQRSTVWY), W502(-ACDEFGILMPQSTVY), 502.5(ADEFGHILMNPQSTVWY), T503(-ADEFGHILMNPQSWY), 503.5(ADEFGILMNPQSTVW), G504(-ACDEFHILMNPQSTVWY), 504.5(ACDEFGHILMNPQSTVWY), A505(-CDEFGHILMNPQSTVWY), 505.5(ACDEFGILMPQSTVWY), T506(-FGILMNPQS), 506.5(ACIPSTVW), K507(-ACEFHILMNVWY), Y508(-DFIMSTV), H509(EFKNQR), 509.5(K), L510(I), 510.5(K), N511(ACDEGLMQSWY), 512.5(S), R513(HIV), D514(ACEFGILMQSTV), S515(ACINTV), L516(ACIMRS), V517(CL), 517.5(C), N518(AILQRTVY), P521(CFMNS), 521.5(M), A522(CSV), M523(CLV), 523.5(A), A524(GPS), 524.5(ACGHSTW), S525(CMNPT), 525.5(ACDEFGHILMNPQSTVWY), H526(-DEFGIKLMPRVWY), 526.5(ACDEFGHILMNPQSTVWY), K527 (-DEFGHILPRSTVWY), 527.5(ACDEFGHILMPQSTVWY), D528(AEFMPQSVW), 528.5(DEPT), D529(ES), 529.5(ADEGLMNPQTV), E530(DNPVW), 530.5(ACDEFGHIKLMNQRSTVWY), E531(ACFGHILMNPQSTVY), 531.5(ADEFGIKLMNPQRSTVY), K532 (-ACDEGPR), 532.5(ACDEFGHIKLMNPQSTVWY), F533(ACDEGHILNQSTVW), 533.5(ACDEFGHILNPQSTVWY), F534(ILMVWY), 534.5(F), P535(-AF), Q536(-ACDEFGHILMNPSTVWY), 536.5(ACILTV), S537(-ACDFGHNQTY), 537.5(T), G538(-), V539(ACHILMNQST), L540(IM), 540.5(KN), I541(-ADEFGKPQRTV), 541.5(ACDEGMQRSTV), F542(GP), 542.5(QY), G543(APS), 543.5(ADHIKLMPQRSTV), K544(-AFGINQSTVY), 544.5(ADEFGHIKLMNRSTVWY), Q545(-ADFGHKLNPRSTWY), 545.5(ACEFGHILMNPQSTVWY), G546(ACEFHLNPQSTVWY), 546.5(ACDEFGHILMNQSTVWY), S547(-CDFGHILNQVWY), 547.5(ACDGHILMNPQSTVWY), E548(ADFGILMNPSWY), | |

TABLE 7-continued

Amino acid alterations that reduce delivery to liver.

| Amino acid alteration | Fold increase of efficiency |
| --- | --- |
| 548.5(ACDFGHILNPSTWY), K549(-DEFGHILNPQSTY), 549.5(ADEFGLMNQSTVY), T550(-CQSWY), 550.5(ADEGIKMNPQRSTV), N551(-ACDEFGHIKMPQRSTVY), 551.5(ACDEFILMPQST), V552(CEILQST), 552.5(VW), D553(AEGST), I554(ACEHQSTVW), E555(AGHNSTVY), 555.5(N), K556(CDMQW), 556.5(Q), V557(IL), M558(AHILNSTV), I559(FQV), T560(AV), D561(EHILNRSVY), E562(AD), E563(CR), I565(LT), 565.5(Y), R566(DFHLMQY), T567(P), 567.5(E), T568(P), 569.5(M), P570(QS), 570.5(M), V571(ACDEFHILMQSTY), A572(CGY), 572.5(WY), T573(ACDGHINSVWY), 573.5(T), E574(ACDFLMQSW), 574.5(V), Q575(-CFGHIKLMNSTVW), 575.5(AWY), Y576(ACFGHIMSV), 576.5(EFWY), G577(DW), 577.5(ACDEHIMNQSTV), S578(ACFHLNQVY), 578.5(ACDEFGHILNSTVY), V579(CDEFGHILMNQSTWY), 579.5(ACDEFGILMNPQSTVWY), S580 (-CDEFGHILMNPQTVWY), 580.5(ACDEFGIKLMNPQRSTVWY), T581 (-AFGHLNPQSWY), 581.5(ACDEFGILMNPQTVWY), N582 (-ACDEFGHIKLMPQRSTVWY), 582.5(DFGHNPSTVW), L583 (-ADEFGMPSTVWY), 583.5(DEGIMNPQSTVY), Q584 (-ADEFGHILMNPSTVWY), 584.5(ACDEFGHILMNPQSTVWY), R585 (-ACDFGHIKLMNPSTVWY), 585.5(ADEFGHILMNPQSTVWY), G586 (-DEFHLMTVY), 586.5(ACDEFGHILMNPQSTVY), N587 (-DEFHILMPQSTVY), 587.5(ADEFGHILMNPQSTVWY), R588 (-ACDEFGHIKLMNPQSTVWY), 588.5(ADEFGHILMNPQSTVY), Q589 (-ADEFGIMNPRSTVWY), 589.5(ACDEFGHIKLMNPQSTVWY), A590(DEFHKLMNQTWY), 590.5(ACDEFGIKLMNPQSTVWY), A591 (-FGILNPVWY), 591.5(ACDEFGHILMNPQSTVY), T592 (-CDEFGHLMNPQVY), 592.5(ACDEFGILMNPQSTVWY), A593 (-CFLMNPWY), 593.5(ACDEFGHILMNPQSTVWY), D594(ELT), 594.5(ACDEFGHILMNPQSTVWY), V595(ACDEFGHILMNPQSTWY), 595.5(ACDEFGHILMNQSTVW), N596(ADEFGHIMPQSTWY), 596.5(DENY), T597(EFGKPRV), 597.5(F), Q598(AEFGHNSY), G599(SW), V600(LM), 600.5(F), L601(MVWY), P602(CMQ), G603(A), M604(ACQS), V605(ACFMNT), 605.5(N), 606.5(P), D608(ENQW), R609(D), D610(Y), 610.5(F), Y612(R), 613.5(Y), Q614(NT), G615(S), P616(ACH), I617(KM), 617.5(I), K620(ACGHMNQS), I621(HKLQRTV), H623(CDFKLSVW), G626(A), H627(AFGILMNQVW), F628(ILM), H629(WY), P630(ACGQTV), 630.5(CV), S631(AHNT), L633(FHMY), M634(CI), F637(IW), L639(FVY), K640(AFNRTVWY), 640.5(N), H641(CIKL), P644(W), Q645(LMT), I646(CLMTV), L647(FIY), I648(CV), N650(CILTV), P652(A), V653(CT), A655(S), 655.5(LMV), N656(FQTW), 657.5(CDFGHLMNQSTVW), S658(AFGIMNQT), 658.5(ACEFGHIKLNQRWY), T659(-CEGIQRY), 659.5(ACDEFGIMNPSVY), T660(-CDEGHKMPQRV), 660.5(ADEFGHIKLPQRWY), F661(AEILMQSTVY), 661.5(ACDEFGIKLMNPRSVY), S662(CPQRW), 662.5(ACDEFGHIKLMNPQRSTVW), A663(FHIKLMNPRY), 663.5(CDGHILMNPRSTVWY), A664(CDHKNRWY), 664.5(ACDEHLMNPRTVWY), K665(ACFGHIMNPQRSTW), 665.5(AHILNPQRSTVWY), F666(CGLNSWY), 666.5(IPV), A667(CEGILMNPRY), 667.5(HNQY), S668(AG), F669(Y), I670(V), T671(NRS), Q672(CEGLS), S674(G), T675(S), V678(ACT), S679(CEFGHIKLRY), V680(CL), E681(DLMNSTV), I682(M), E683(HIQ), E685(ADLQT), L686(T), Q687(IMVW), K688(HP), N690(R), E697 (-DHIMPR), 697.5(GHNPQW), I698(-DL), 699.5(E), T701(S), 701.5(A), S702(IQV), 702.5(Q), N703(DG), 703.5(AEHLTY), Y704(FH), 704.5(ADEILNST), N705(CDEFHIKLMPQTV), 705.5(ENQY), K706(DEGRST), S707(CDEFGHILMNQTVY), 707.5(MY), V708(ACEGHNRST), 708.5(I), N709(CDKLPQRV), 709.5(CGPQ), V710(AELMNPQ), 710.5(D), D711(GNP), 711.5(QY), T713(ACS), T716(ACFIKLNQRVWY), N717(ADEFHRSY), V719(FKLNQRY), 720.5(N), S721(CFHIKLMNQRTVWY), E722(DQ), P723(ACDEHNQSTV), R724(FHKNSWY), P725(ACILQV), I726(LV), R733(K), N734(AEISV), L735(C) | |

TABLE 8

Amino acid alterations that reduce delivery to spleen.

| Amino acid alteration | Fold increase of efficiency |
| --- | --- |
| D439(K), 444.5(CLM), 445.5(ACELMNST), 446.5(CN), 447.5(INP), 460.5(W), G466(Q), 476.5(L), 478.5(L), R484(EFGLMNSTVY), 485.5(IKM), Q486(IVW), R487(CDFGILNSTVW), 487.5(F), 488.5(WY), K490(EP), 493.5(K), 497.5(D), S498(D), 498.5(DE), E499(C), 499.5(CDE), 503.5(IMQW), 504.5(FLNSTY), A505(E), 505.5(ACLQTVW), 506.5(ACISV), 523.5(A), 524.5(GHS), 525.5(ACDFGHILNQSTVWY), H526(EL), 526.5(CDEFHILMNPQSTWY), K527(-W), 527.5(ACDEHILMPSVWY), 528.5(D), 529.5(D), 530.5(IW), 531.5(IV), K532(P), 532.5(CGHIPQSTVWY), 533.5(CFNPQW), 534.5(F), P535(-F), Q536(-), 536.5(CITV), V571(H), 575.5(W), 576.5(W), G577(D), 577.5(DI), 578.5(CEITY), 579.5(Q), S580(-), T581(DE), 581.5(CY), N582(F), Q584(W), 586.5(F), R588(N), 590.5(K), A591(E), 591.5(DEP), T592(DE), 592.5(CMP), A593(-P), 593.5(FGPW), 595.5(CD), 596.5(DEY), 605.5(N) | 0.1-fold |
| D180(M), 266.5(E), 268.5(E), 379.5(E), 380.5(E), 382.5(D), 433.5(F), D439(K), 444.5(CLM), L445(F), 445.5(ACEGHILMNQSTV), S446(-), 446.5(ACEFHILMNPQSTVWY), R447(EFIWY), 447.5(DEGHILMNPQVW), T448(-DEHINPQV), 448.5(DEP), N449(P), G453(K), 453.5(Y), 454.5(F), S458(E), R459(D), L460(Y), 460.5(W), 462.5(N), 463.5(F), G466(Q), 469.5(E), R471(EG), S474(I), 476.5(L), 478.5(L), P479(T), 479.5(D), C482(W), 483.5(V), R484(EFGHILMNQSTVY), 485.5(EIKM), Q486(EFIMVWY), 486.5(FV), R487(ACDEFGHILMNPQSTVWY), 487.5(FW), V488(H), 488.5(DEILPWY), S489(DLMPQWY), 489.5(DPTW), K490(-CDEPW), 490.5(DE), T491(DP), 491.5(DEFKW), 492.5(DE), A493(D), 493.5(DEK), D494(F), 494.5(DE), N495(FLP), 495.5(CI), N496(D), N497(-), 497.5(DE), S498(DE), 498.5(DE), E499(C), 499.5(ACDEGPQ), Y500(ACDEIPV), 500.5(DELQ), 501.5(CEGNW), W502(-EP), 502.5(ADEFGMNPTWY), T503(DE), 503.5(DEFGILMNQSTVW), G504(-DILNPTVY), 504.5(ACDEFGILMNPQSTVWY), A505(DEHILMNQY), 505.5(ACDEGILMPQSTVW), T506(-F), 506.5(ACIPSTV), K507(-ACEINSWY), Y508(-), H509(FN), 509.5(K), 510.5(K), 517.5(C), 523.5(A), 524.5(ACGHST), 525.5(ACDEFGHILMNPQSTVWY), H526(DEILPV), 526.5(ACDEFGHILMNPQSTVWY), K527(-FHLPWY), 527.5(ACDEFGHILMPQSTVWY), 528.5(DET), 529.5(ADELMPV), E530(PW), 530.5(CDEFILMNQTVWY), 531.5(ADEFGILNPQTV), K532(-ACFGHILMNPQSTVW), 532.5(ACGHILMPQSTVWY), F533(ADEGSTV), 533.5(ACEFGHILNPQSTVWY), 534.5(F), P535(-F), Q536(-DP), 536.5(ACILTV), S537(-), 537.5(T), 559.5(A), V571(EHS), 571.5(G), 573.5(T), Q575(K), 575.5(WY), Y576(V), 576.5(W), G577(D), 577.5(ACDEHIMQS), S578(DE), 578.5(ACEFILSTY), V579(DEW), 579.5(DEFILNQTY), S580(-DEQ), T581(DEP), 581.5(CDIQY), N582(-CFILY), 582.5(FGT), 583.5(PTVY), Q584(GVW), 584.5(DEIMPV), R585(AEFGHILMNQSTVWY), 585.5(AFILMPSTVY), G586(-DE), 586.5(ACFGILMNPQSTV), N587(-DE), 587.5(ADILMNTV), R588(ACFHILMNQSVWY), 588.5(GIV), 589.5(CFHKPV), A590(M), 590.5(CGKPQST), A591(DEW), 591.5(CDEFGILMPTV), T592(-DE), 592.5(ACEFGILMNPQSTVWY), A593(-DEP), 593.5(ACDFGILMNPSTVWY), D594(LT), 594.5(ACFGHILMPQTVWY), 595.5(CDEFGIQTVW), N596(DE), 596.5(DEY), 605.5(N), 606.5(P), R609(D), D610(Y), 617.5(I) | 0.2-fold |
| D180(M), 180.5(M), S261(D), 264.5(D), 266.5(E), S267(E), 267.5(E), N268(E), 268.5(E), H271(E), 379.5(DE), L380(E), 380.5(E), 382.5(D), 383.5(E), 386.5(D), 431.5(Y), 433.5(F), D439(K), 444.5(CLM), L445(FY), 445.5(ACDEGHILMNQSTV), S446(-EL), 446.5(ACDEFGHILMNPQSTVWY), R447(-DEFIPVWY), 447.5(CDEGHILMNPQVW), T448(-DEGHILNPQVW), 448.5(DEP), N449(DEP), 449.5(E), G453(IK), 453.5(Y), 454.5(EF), T455(E), 457.5(D), S458(DE), 458.5(DE), R459(DE), L460(WY), 460.5(W), Q461(D), 462.5(N), 463.5(F), 464.5(Y), G466(Q), 469.5(E), R471(EGSTV), S474(I), 475.5(W), 476.5(L), 478.5(L), P479(GT), 479.5(D), G480(Y), C482(W), 482.5(F), 483.5(QV), R484(EFGHILMNQSTVY), 485.5(EIKMQY), Q486(DEFIMPVWY), 486.5(FV), R487(-ACDEFGHIKLMNPQSTVWY), 487.5(FW), V488(EFGHY), 488.5(DEILPSWY), S489(-DEFGKLMPQTVWY), 489.5(ADEGPQRSTW), K490(-CDEFGLNPWY), 490.5(CDEFIPVY), T491(DEP), 491.5(DEFHIKLMWY), 492.5(DEY), A493(DE), 493.5(DEHKP), D494(FR), 494.5(DEGP), N495(-AEFGILMPQSTVWY), 495.5(CDEGILPTV), N496(-CDEGILM), 496.5(DE), N497(-CEH), 497.5(DE), S498(-CDEFPR), 498.5(DE), E499(CIP), 499.5(ACDEGLMNPQSTVW), Y500(ACDEGIKLPV), 500.5(ADEFGILNPQST), S501(D), 501.5(ACDEFGHILMNQSTVWY), W502(-ACDEMP), 502.5(ADEFGILMNPSTVWY), T503(-DE), 503.5(ADEFGILMNPQSTVW), G504(-CDEFILNPSTVWY), 504.5(ACDEFGHILMNPQSTVWY), A505(-DEFHILMNPQWY), 505.5(ACDEFGILMPQSTVWY), T506(-FLM), 506.5(ACIPSTVW), K507(-ACEFHILMNQSTVWY), Y508(-), H509(CEFN), 509.5(K), 510.5(K), | 0.3-fold |

TABLE 8-continued

| Amino acid alterations that reduce delivery to spleen. | |
|---|---|
| Amino acid alteration | Fold increase of efficiency |
| R513(C), D514(FILV), 517.5(C), 521.5(MS), 523.5(A), 524.5(ACGHST), S525(HM), 525.5(ACDEFGHILMNPQSTVWY), H526(DEILMPV), 526.5(ACDEFGHILMNPQSTVWY), K527(-DEFHILPQVWY), 527.5(ACDEFGHILMPQSTVWY), 528.5(DET), 529.5(ADEGLMNPQV), E530(PW), 530.5(ACDEFGILMNQSTVWY), 531.5(ADEFGILMNPQRSTVY), K532(-ACFGHILMNPQSTVWY), 532.5(ACDEFGHIKLMNPQSTVWY), F533(ACDEGIQSTV), 533.5(ACDEFGHILNPQSTVWY), 534.5(F), P535(-F), Q536(-DPW), 536.5(ACILTV), S537(-), 537.5(T), G538(-), 559.5(A), R566(D), T568(P), P570(Q), 570.5(M), V571(ADEFHS), 571.5(G), 572.5(Y), T573(D), 573.5(MT), Q575(DK), 575.5(FWY), Y576(HMV), 576.5(EFWY), G577(D), 577.5(ACDEHIMQSTV), S578(DE), 578.5(ACDEFILSTVY), V579(DEW), 579.5(DEFGILMNQTVY), S580(-DEILMQY), 580.5(DEN), T581(-DEP), 581.5(ACDEILMPQY), N582(-ACEFHILMPTVWY), 582.5(DFGHPTVW), L583(-P), 583.5(GNPQSTVY), Q584(DFGILNPTVWY), 584.5(ACDEFGHILMNPQSTV), R585(-ACEFGHILMNQSTVWY), 585.5(ADFGILMNPQSTVWY), G586(-DE), 586.5(ACDFGHILMNPQSTV), N587(-DEILQVY), 587.5(ADEFGILMNPQSTV), R588(-ACEFHILMNPQSTVWY), 588.5(DEGILMPV), Q589(-DR), 589.5(ACDEFHKNPTVW), A590(DELMNQ), 590.5(ACEGIKMPQSTW), A591(-DEWY), 591.5(ACDEFGHILMNPQSTV), T592(-DEP), 592.5(ACDEFGILMNPQSTVWY), A593(-DEP), 593.5(ACDEFGILMNPQSTVWY), D594(LT), 594.5(ACDFGHILMPQSTVWY), V595(DEGHW), 595.5(ACDEFGILQTVW), N596(DEI), 596.5(DEY), T597(E), Q598(FY), 605.5(N), 606.5(P), 607.5(P), D608(W), R609(D), D610(Y), 617.5(I), 640.5(N), 667.5(Y) | |
| 4.5(H), 45.5(M), 50.5(N), G58(C), S156(T), D180(M), 180.5(M), 183.5(M), L256(A), S261(D), S262(T), 262.5(E), Q263(G), S264(W), 264.5(D), 265.5(D), 266.5(E), S267(E), 267.5(E), N268(DE), 268.5(E), 269.5(D), H271(E), Q325(K), 379.5(DE), L380(E), 380.5(E), N381(D), N382(DE), 382.5(D), 383.5(E), 384.5(D), 386.5(D), V387(E), G406(E), A425(-), Q428(E), 431.5(Y), R432(I), 433.5(F), D439(K), 441.5(M), 444.5(CLM), L445(FY), 445.5(ACDEGHILMNQSTVY), S446(-DEILQV), 446.5(ACDEFGHILMNPQSTVWY), R447(-DEFILMPTVWY), 447.5(ACDEFGHILMNPQVWY), T448(-ACDEFGHILMNPQVWY), 448.5(CDEFNPWY), N449(DEFMPW), 449.5(E), T450(E), 450.5(F), 451.5(N), 452.5(AL), G453(DEFIKLNS), 453.5(FILMNVY), T454(-FI), 454.5(DEFLM), T455(-DEMY), 455.5(P), T456(-DEK), 456.5(DE), Q457(DEP), 457.5(DEPW), S458(DEFMWY), 458.5(DEFILMNTWY), R459(-ACDEGIPTV), 459.5(DE), L460(FHWY), 460.5(W), Q461(DE), 462.5(N), S463(G), 463.5(F), 464.5(SY), G466(Q), 469.5(DE), R471(ACDEGMQSTV), D472(Y), S474(I), R475(H), 475.5(SW), N476(TW), 476.5(L), 477.5(L), 478.5(L), P479(GT), 479.5(D), G480(Y), 481.5(H), C482(W), 482.5(FM), Y483(TVW), 483.5(FQV), R484(EFGHIKLMNQSTVY), 484.5(N), Q485(ACGLST), 485.5(EIKMQY), Q486(ADEFGILMNPVWY), 486.5(FV), R487 (-ACDEFGHIKLMNPQSTVWY), 487.5(FW), V488(EFGHWY), 488.5(ACDEGILMPQSWY), S489(-CDEFGHIKLMNPQTVWY), 489.5(ACDEGLMPQRSTVWY), K490(-ACDEFGHILMNPQSTVWY), 490.5(ACDEFHIMPQRTVWY), T491(-DEP), 491.5(ACDEFHIKLMNPQSTVWY), S492(-E), 492.5(ADEGHILSVY), A493(-DEHR), 493.5(ADEFHIKLMPQSVWY), D494(FR), 494.5(DEGILMPTVY), N495(-ADEFGHILMPQSTVWY), 495.5(ACDEFGILMPQSTVW), N496(-ACDEGILMPQVW), 496.5(DEFQW), N497(-CEHW), 497.5(DE), S498(-CDEFILPRVW), 498.5(DEFLPQY), E499(CIPQS), 499.5(ACDEGHILMNPQRSTVWY), Y500(-ACDEGIKLNPQV), 500.5(ADEFGHILMNPQSTVY), S501 (-DILNVW), 501.5(ACDEFGHILMNQRSTVWY), W502 (-ACDEGILMPQSTVY), 502.5(ADEFGHILMNPQSTVWY), T503 (-DEGLMPW), 503.5(ADEFGILMNPQSTVW), G504 (-CDEFHILMNPQSTVWY), 504.5(ACDEFGHILMNPQSTVWY), A505 (-DEFHILMNPQTVWY), 505.5(ACDEFGILMPQSTVWY), T506 (-FGILMV), 506.5(ACIPSTVW), K507(-ACEFHILMNQSTVWY), Y508(-), H509(CEFNQ), 509.5(K), 510.5(K), N511(EWY), 512.5(S), R513(CIV), D514(ACEFILMQV), 517.5(C), 521.5(MS), M523(V), 523.5(A), 524.5(ACGHSTW), S525(HM), 525.5(ACDEFGHILMNPQSTVWY), H526(-ADEGILMPQTVW), 526.5(ACDEFGHILMNPQSTVWY), K527 (-DEFHILMPQSTVWY), 527.5(ACDEFGHILMPQSTVWY), D528(AFQ), 528.5(DEPT), D529(S), 529.5(ADEGLMNPQTV), E530(NPVW), 530.5(ACDEFGHIKLMNQRSTVWY), E531(ACGHILMNV), 531.5(ADEFGIKLMNPQRSTVY), K532(-ACDEFGHILMNPQSTVWY), 532.5(ACDEFGHIKLMNPQSTVWY), F533(ACDEGILMNQSTV), 533.5(ACDEFGHILNPQSTVWY), F534(LVY), 534.5(F), P535(-AF), | 0.5-fold |

TABLE 8-continued

Amino acid alterations that reduce delivery to spleen.

| Amino acid alteration | Fold increase of efficiency |
| --- | --- |
| Q536(-ADEGPWY), 536.5(ACILTV), S537(-DY), 537.5(T), G538(-), V539(H), 542.5(Y), D553(T), I554(E), 559.5(A), E562(A), R566(DEFY), 567.5(E), T568(P), P570(Q), 570.5(M), V571(ADEFHMQSY), 571.5(G), A572(Y), 572.5(WY), T573(DGV), 573.5(MT), E574(D), 574.5(V), Q575(DGKL), 575.5(AFWY), Y576(ACGHIMSV), 576.5(EFWY), G577(DW), 577.5(ACDEHIMNQSTV), S578(DEFILNWY), 578.5(ACDEFGHILNSTVY), V579(ADEFGSWY), 579.5(ACDEFGILMNPQTVWY), S580(-DEFHILMNPQY), 580.5(ACDEFGKLMNPRVW), T581(-DEKP), 581.5(ACDEGILMNPQVWY), N582(-ACDEFHILMPQRSTVWY), 582.5(DFGHPSTVW), L583(-DGP), 583.5(DEGIMNPQSTVY), Q584 (-ADEFGHILNPSTVWY), 584.5(ACDEFGHILMNPQSTVWY), R585 (-ACDEFGHIKLMNPQSTVWY), 585.5(ADEFGHILMNPQSTVWY), G586(-DEFMW), 586.5(ACDEFGHILMNPQSTV), N587 (-DEGHILMPQVY), 587.5(ADEFGILMNPQSTVWY), R588 (-ACDEFGHIKLMNPQSTVWY), 588.5(DEFGHILMPTVY), Q589(-DEPR), 589.5(ACDEFGHIKNPSTVWY), A590(DEHKLMNQY), 590.5(ACDEFGIKLMNPQSTVWY), A591(-DEFPWY), 591.5(ACDEFGHILMNPQSTVWY), T592(-DEGPV), 592.5(ACDEFGILMNPQSTVWY), A593(-DEP), 593.5(ACDEFGHILMNPQSTVWY), D594(ELT), 594.5(ACDEFGHILMNPQSTVWY), V595(DEGHLMNPQWY), 595.5(ACDEFGHILMNQSTVW), N596(DEIP), 596.5(DENY), T597(DE), 597.5(F), Q598(FHY), G599(W), 600.5(F), L601(Y), 605.5(N), 606.5(P), 607.5(P), D608(W), R609(D), D610(Y), 610.5(F), 613.5(Y), I617(K), 617.5(I), 640.5(N), T660(H), 662.5(F), 667.5(Y), K706(DEG) | |
| 4.5(H), 38.5(G), K39(E), 45.5(M), G49(H), Y50(H), 50.5(N), G58(C), E74(I), S156(T), 157.5(P), D180(M), 180.5(M), 183.5(M), 184.5(M), 189.5(M), P192(M), A194(C), R238(H), H255(N), L256(ACGHS), 260.5(DST), S261(D), 261.5(S), S262(T), 262.5(EGINS), Q263(AGW), S264(DEW), 264.5(D), 265.5(DE), 266.5(E), S267(E), 267.5(E), N268(DEQ), 268.5(E), 269.5(D), N270(CDGY), H271(E), D295(E), L311(I), 324.5(K), Q325(KR), N326(L), T330(K), Y348(D), T379(A), 379.5(DE), L380(EY), 380.5(E), N381(DGQ), N382(DE), 382.5(D), 383.5(E), 384.5(D), Q385(T), A386(E), 386.5(DE), V387(DE), 387.5(EGP), R389(I), S390(DN), P399(M), 404.5(N), G406(DE), 408.5(N), F409(CH), S412(W), 416.5(N), 417.5(M), A425(-Q), H426(N), Q428(EH), S429(Y), D431(M), 431.5(Y), R432(-I), L433(D), 433.5(F), I438(K), D439(HKT), 441.5(M), L442(FI), 444.5(CLM), L445(CFMY), 445.5(ACDEGHILMNQSTVY), S446 (-DEHILMNQTV), 446.5(ACDEFGHILMNPQSTVWY), R447 (-ACDEFGHILMNPQSTVWY), 447.5(ACDEFGHILMNPQSVWY), T448 (-ACDEFGHILMNPQVWY), 448.5(ACDEFGILMNPWY), N449 (-DEFILMPVW), 449.5(AEGHLNPS), T450(-CDEPW), 450.5(DEFHV), 451.5(N), S452(-DEFPVW), 452.5(AILPV), G453 (-ADEFHIKLMNPQSTV), 453.5(FILMNTVY), T454(-DEFILMP), 454.5(DEFLMP), T455(-DEILMQY), 455.5(FLPQY), T456(-DEGHIKP), 456.5(ADEGHILNP), Q457(DEGLP), 457.5(ADEGHILPWY), S458(DEFHMNVWY), 458.5(DEFGHILMNTWY), R459 (-ACDEGILMNPQSTVWY), 459.5(DEP), L460(AFHMPWY), 460.5(W), Q461(DEIKV), F462(Y), 462.5(N), S463(CDGKNQ), 463.5(F), Q464(V), 464.5(SY), G466(Q), A467(HMY), S468(CDF), 469.5(DE), R471(ACDEGMQSTV), D472(Y), Q473(FHY), S474(I), R475(H), 475.5(SW), N476(TW), 476.5(L), W477(Y), 477.5(L), L478(FI), 478.5(L), P479(GT), 479.5(D), G480(Y), 481.5(HY), C482(FGWY), 482.5(FM), Y483(ACFHITVW), 483.5(FQV), R484(EFGHIKLMNQSTVY), 484.5(N), Q485(ACFGILNSTVY), 485.5(EIKMQY), Q486(ACDEFGILMNPSVWY), 486.5(FV), R487(-ACDEFGHIKLMNPQSTVWY), 487.5(FW), V488(AEFGHNQTWY), 488.5(ACDEFGILMPQSVWY), S489 (-ACDEFGHIKLMNPQTVWY), 489.5(ACDEGLMPQRSTVWY), K490 (-ACDEFGHILMNPQRSTVWY), 490.5(ACDEFGHILMNPQRSTVWY), T491(-DEP), 491.5(ACDEFGHIKLMNPQSTVWY), S492(-CEF), 492.5(ADEGHILMPQSTVY), A493(-DEFHILRWY), 493.5(ADEFGHIKLMNPQSTVWY), D494(FR), 494.5(ADEGHILMPSTVWY), N495(-ADEFGHILMPQSTVWY), 495.5(ACDEFGILMPQSTVWY), N496(-ACDEFGILMPQTVW), 496.5(ADEFGHILPQWY), N497(-CEFHIMSVWY), 497.5(ADEGMPY), S498(-CDEFILMPRVWY), 498.5(DEFGILMPQSY), E499(CIPQS), 499.5(ACDEGHILMNPQRSTVWY), Y500(-ACDEGIKLMNPQSTV), 500.5(ADEFGHILMNPQSTVWY), S501(-CDEFILNTVW), 501.5(ACDEFGHILMNQRSTVWY), W502(-ACDEFGILMPQSTVY), 502.5(ADEFGHILMNPQSTVWY), T503(-ADEFGILMPQVWY), 503.5(ADEFGILMNPQSTVW), G504(-ACDEFHILMNPQSTVWY), 504.5(ACDEFGHILMNPQSTVWY), A505(-CDEFHILMNPQSTVWY), 505.5(ACDEFGILMPQSTVWY), T506(-FGILMNPQV), 506.5(ACIPSTVW), K507(-ACEFHILMNQSTVWY), Y508(-DS), | 0.7-fold |

TABLE 8-continued

| Amino acid alterations that reduce delivery to spleen. | |
|---|---|
| Amino acid alteration | Fold increase of efficiency |
| H509(CEFNQ), 509.5(K), L510(I), 510.5(K), N511(DELMQWY), 512.5(S), R513(CHIV), D514(ACEFGILMQTV), L516(ACST), V517(L), 517.5(C), N518(R), P521(MS), 521.5(MS), M523(CV), 523.5(A), A524(GP), 524.5(ACGHSTW), S525(AGHMNP), 525.5(ACDEFGHILMNPQSTVWY), H526(-ACDEFGIKLMNPQSTVWY), 526.5(ACDEFGHILMNPQSTVWY), K527(-DEFGHILMPQSTVWY), 527.5(ACDEFGHILMPQSTVWY), D528(AFMPQSVW), 528.5(DEPT), D529(S), 529.5(ADEGLMNPQTV), E530(NPVW), 530.5(ACDEFGHIKLMNQRSTVWY), E531(ACFGHILMNPQSTVY), 531.5(ADEFGIKLMNPQRSTVY), K532 (-ACDEFGHILMNPQRSTVWY), 532.5(ACDEFGHIKLMNPQSTVWY), F533(ACDEGHILMNQSTVW), 533.5(ACDEFGHILNPQSTVWY), F534(ILMVWY), 534.5(F), P535(-AF), Q536(-ACDEFGNPTWY), 536.5(ACILTV), S537(-ADFGQY), 537.5(T), G538(-), V539(HLM), 540.5(K), 541.5(Q), F542(P), 542.5(Y), 543.5(CQRY), K544(Q), 544.5(AIKRVY), 545.5(CFNPQVWY), G546(Y), 546.5(EGSTWY), S547 (-Q), 547.5(ADNVY), E548(FN), 548.5(CDHMPY), K549(-DILW), 549.5(DH), T550(C), 550.5(KR), N551(CDEIRTV), 551.5(CDEM), D553(AT), I554(EHQ), E555(GHTV), K556(EMW), M558(A), 558.5(E), 559.5(A), T560(A), 560.5(A), E562(A), I565(T), R566(ACDEFGHILMNTVWY), 567.5(E), T568(P), 569.5(M), P570(QS), 570.5(M), V571(ADEFHLMQSTY), 571.5(G), A572(CY), 572.5(VWY), T573(ACDGINSVW), 573.5(MT), E574(DQ), 574.5(V), Q575 (-CDGIKLMSTVY), 575.5(AFWY), Y576(ACGHIMSV), 576.5(EFWY), G577(DW), 577.5(ACDEHIMNQSTV), S578(DEFGILNWY), 578.5(ACDEFGHILNSTVY), V579(ACDEFGHLMNQSTWY), 579.5(ACDEFGILMNPQSTVWY), S580(-DEFHILMNPQVY), 580.5(ACDEFGKLMNPQRSTVWY), T581(-CDEFGKPWY), 581.5(ACDEFGILMNPQTVWY), N582(-ACDEFGHIKLMPQRSTVWY), 582.5(DFGHNPSTVW), L583(-ADEGPST), 583.5(DEGIMNPQSTVY), Q584(-ADEFGHILMNPSTVWY), 584.5(ACDEFGHILMNPQSTVWY), R585(-ACDEFGHIKLMNPQSTVWY), 585.5(ADEFGHILMNPQSTVWY), G586(-DEFHMNWY), 586.5(ACDEFGHILMNPQSTVY), N587 (-DEFGHILMPQSTVY), 587.5(ADEFGILMNPQSTVWY), R588 (-ACDEFGHIKLMNPQSTVWY), 588.5(ADEFGHILMPQSTVY), Q589 (-DEIPRW), 589.5(ACDEFGHIKLNPQSTVWY), A590(DEFHKLMNQWY), 590.5(ACDEFGIKLMNPQSTVWY), A591(-CDEFIMNPTVWY), 591.5(ACDEFGHILMNPQSTVWY), T592(-ADEFGHMNPQVY), 592.5(ACDEFGILMNPQSTVWY), A593(-DEP), 593.5(ACDEFGHILMNPQSTVWY), D594(ELT), 594.5(ACDEFGHILMNPQSTVWY), V595(ADEFGHLMNPQSTWY), 595.5(ACDEFGHILMNQSTVW), N596(DEIPQT), 596.5(DENY), T597(DEHINQ), 597.5(F), Q598(ACEFHIMNVY), G599(CW), 600.5(F), L601(WY), P602(Q), 605.5(N), 606.5(P), 607.5(P), D608(W), R609(D), D610(Y), 610.5(F), 613.5(Y), Q614(T), I617(K), 617.5(I), P630(H), L633(FHY), 640.5(N), I646(M), L647(I), 657.5(C), S658(E), 658.5(C), T659(K), 659.5(CN), T660(H), F661(EQ), 661.5(C), S662(W), 662.5(FHLMW), 663.5(M), 664.5(C), 665.5(N), 667.5(Y), S674(G), 703.5(E), Y704(H), 704.5(DI), N705(EK), K706(DEGRST), S707(D), 707.5(MY), V708(CR), 708.5(I), V710(EN), 710.5(D), D711(N), 711.5(Y) | |
| 4.5(H), 10.5(I), E12(H), R20(Q), W23(M), 23.5(F), 24.5(N), P32(C), A35(Y), 35.5(HY), 36.5(K), 38.5(ADGKV), K39(-AEV), 39.5(D), 40.5(DE), R43(GW), 45.5(M), G49(HM), Y50(H), 50.5(N), G58(C), 58.5(F), G62(Q), E63(CM), E74(I), A78(C), 78.5(Q), 83.5(DH), G86(D), D87(K), A98(N), E106(H), D107(Q), S109(F), 109.5(D), 117.5(K), F119(Q), 119.5(H), 122.5(E), 125.5(C), P128(F), 135.5(M), 143.5(K), R144(N), P150(M), 150.5(M), S156(T), 156.5(T), 157.5(P), T159(C), K161(DN), A162(-), G163(CN), Q164(M), 166.5(N), G174(C), G177(Q), 177.5(I), 179.5(CD), D180(CM), 180.5(CM), 181.5(NW), P183(C), 183.5(M), D184(Y), 184.5(MY), P185(EV), Q186(P), 186.5(C), P187(CK), 189.5(M), Q190(M), 191.5(W), P192(CMW), A193(C), 193.5(W), A194(C), P195(A), 195.5(Y), G197(A), L198(C), 199.5(CF), N201(D), M203(C), G206(F), P210(K), N215(DFM), G217(CEV), A218(Q), N223(CM), S225(C), H229(D), T233(D), 237.5(HQ), R238(H), 238.5(F), I240(CW), T244(C), P250(Q), N254(C), H255(N), L256(ACGHS), Q259(G), 260.5(ACDEMQST), S261(D), 261.5(S), S262(T), 262.5(EGINST), Q263(AGW), 263.5(DG), S264(-DEFLW), 264.5(D), 265.5(DE), 266.5(E), S267(ET), 267.5(E), N268(DEQ), 268.5(E), 269.5(D), N270(ACDGHSY), H271(EFI), F273(HMW), G280(A), F282(WY), H288(N), D295(E), R307(C), 307.5(K), P308(-), K309(CQ), L311(I), F313(C), K314(MV), T324(C), 324.5(CK), Q325(CHKR), N326(CLM), T330(KQ), 332.5(K), A333(C), V342(AI), T344(FI), S346(PW), Y348(DS), Q349(AGS), V353(T), G355(S), F365(W), A367(P), M371(F), T379(AG), 379.5(DE), L380(ENQTY), 380.5(E), N381(ACDGMQ), N382(DE), 382.5(D), 383.5(E), 384.5(D), Q385(PRT), 385.5(AP), A386(ELNRV), 386.5(CDEP), V387(CDE), 387.5(EGKP), R389(GIQY), S390(DGNT), P399(M), Q401(VW), L403(M), R404(K), | 0.8-fold |

TABLE 8-continued

Amino acid alterations that reduce delivery to spleen.

| Amino acid alteration | Fold increase of efficiency |
| --- | --- |
| 404.5(N), G406(DEN), N408(DGM), 408.5(CN), F409(CH), F411(Q), S412(EW), Y413(M), T414(G), 415.5(GMQ), E416(G), 416.5(EGNR), D417(I), 417.5(AKMQR), V418(GIM), P419(HILWY), Y424(C), 424.5(F), A425(-GQ), H426(N), S427(AC), Q428(EH), S429(CY), L430(M), D431(M), 431.5(Y), R432(-I), L433(DQ), 433.5(F), L437(AY), I438(GKT), D439(HKNPSTY), 441.5(M), L442(FI), 444.5(CLM), L445(CFMVY), 445.5(ACDEGHILMNQSTVY), S446(-CDEGHIKLMNQTV), 446.5(ACDEFGHILMNPQSTVWY), R447(-ACDEFGHILMNPQSTVWY), 447.5(ACDEFGHILMNPQSVWY), T448(-ACDEFGHILMNPQSVWY), 448.5(ACDEFGHILMNPQSWY), N449(-ACDEFGILMPVW), 449.5(AEGHLMNPSTVY), T450(-CDEGPW), 450.5(ADEFGHLMPQSV), 451.5(GNP), S452(-DEFHNPVW), 452.5(AILPV), G453 (-ADEFHIKLMNPQSTV), 453.5(FILMNTVY), T454(-DEFHILMNPV), 454.5(ADEFLMPSTY), T455(-DEILMQY), 455.5(AFHLPQTY), T456 (-DEGHIKLMP), 456.5(ADEGHILMNPV), Q457(-DEFGLP), 457.5(ADEFGHILMNPVWY), S458(DEFHMNVWY), 458.5(DEFGHILMNPSTWY), R459(-ACDEFGHILMNPQSTVWY), 459.5(DEP), L460(AFHIMNPSTVWY), 460.5(W), Q461(DEIKV), F462(Y), 462.5(N), S463(ACDGKNQR), 463.5(F), Q464(ILV), 464.5(SY), A465(C), G466(CQ), 466.5(E), A467(HIMY), S468(CDFM), D469(V), 469.5(DE), I470(FL), R471(ACDEGKMQSTV), D472(MY), Q473(FHMSY), S474(I), R475(H), 475.5(SW), N476(TW), 476.5(L), W477(Y), 477.5(L), L478(FI), 478.5(L), P479(GIT), 479.5(D), G480(Y), P481(ACV), 481.5(GHY), C482(FGWY), 482.5(FM), Y483(ACFHIMTVW), 483.5(FQV), R484(EFGHIKLMNQSTVY), 484.5(N), Q485(ACFGHILMNSTVY), 485.5(EIKMQY), Q486(ACDEFGILMNPSTVWY), 486.5(CFV), R487 (-ACDEFGHIKLMNPQSTVWY), 487.5(FW), V488(AEFGHLMNQTWY), 488.5(ACDEFGILMPQSVWY), S489(-ACDEFGHIKLMNPQTVWY), 489.5(ACDEGLMPQRSTVWY), K490(-ACDEFGHILMNPQRSTVWY), 490.5(ACDEFGHILMNPQRSTVWY), T491(-DEPY), 491.5(ACDEFGHIKLMNPQSTVWY), S492(-CDEFLM), 492.5(ADEGHILMPQSTVY), A493(-DEFHILNPQRVWY), 493.5(ADEFGHIKLMNPQSTVWY), D494(EFR), 494.5(ADEGHILMNPSTVWY), N495(-ADEFGHILMPQSTVWY), 495.5(ACDEFGILMPQSTVWY), N496(-ACDEFGHILMPQTVWY), 496.5(ADEFGHILMPQSTVWY), N497(-ACEFGHILMSVWY), 497.5(ADEFGILMPQVY), S498(-CDEFGILMNPQRTVWY), 498.5(ADEFGILMPQSVWY), E499(CDIPQS), 499.5(ACDEGHILMNPQRSTVWY), Y500(-ACDEGHIKLMNPQSTV), 500.5(ADEFGHILMNPQSTVWY), S501(-CDEFGILMNPTVWY), 501.5(ACDEFGHILMNQRSTVWY), W502(-ACDEFGILMPQSTVY), 502.5(ADEFGHILMNPQSTVWY), T503(-ADEFGILMNPQVWY), 503.5(ADEFGILMNPQSTVW), G504(-ACDEFHILMNPQSTVWY), 504.5(ACDEFGHILMNPQSTVWY), A505(-CDEFGHILMNPQSTVWY), 505.5(ACDEFGILMPQSTVWY), T506(-AFGILMNPQV), 506.5(ACIPSTVW), K507(-ACEFHILMNQRSTVWY), Y508(-DS), H509(CEFNQ), 509.5(K), L510(I), 510.5(K), N511(ACDEGLMQSWY), 512.5(S), R513(CHIV), D514(ACEFGILMQSTV), S515(V), L516(ACIMSTV), V517(CIL), 517.5(C), N518(IQR), P521(FMNS), 521.5(MS), A522(CV), M523(CLV), 523.5(A), A524(GPS), 524.5(ACGHSTW), S525(ACGHMNP), 525.5(ACDEFGHILMNPQSTVWY), H526(-ACDEFGIKLMNPQSTVWY), 526.5(ACDEFGHILMNPQSTVWY), K527(-DEFGHILMPQRSTVWY), 527.5(ACDEFGHILMPQSTVWY), D528(AEFMPQSVW), 528.5(DEPT), D529(S), 529.5(ADEGLMNPQTV), E530(NPVW), 530.5(ACDEFGHIKLMNQRSTVWY), E531(ACFGHILMNPQSTVY), 531.5(ADEFGIKLMNPQRSTVY), K532(-ACDEFGHILMNPQRSTVWY), 532.5(ACDEFGHIKLMNPQSTVWY), F533(ACDEGHILMNQSTVW), 533.5(ACDEFGHILNPQSTVWY), F534(ILMVWY), 534.5(F), P535(-AF), Q536(-ACDEFGHNPTVWY), 536.5(ACILTV), S537(-ADFGNQY), 537.5(T), G538(-), V539(AHLMQST), 540.5(KMN), I541(-DGPT), 541.5(Q), F542(GP), 542.5(QY), G543(P), 543.5(ACDIKPQRTVY), K544 (-FGMNPQ), 544.5(ADEFGHIKLMRVWY), Q545(-FK), 545.5(ACFILMNPQSVWY), G546(DEHLPTVWY), 546.5(ACEGHILMNPQSTVWY), S547(-DHIMQY), 547.5(ADGHNTVWY), E548(FNY), 548.5(ACDEFGHLMNPTWY), K549(-DFHILTWY), 549.5(ADFHLMQSTV), T550(CW), 550.5(AIKMNPRSTV), N551(ACDEHIKLPQRTV), 551.5(ACDEHILMNS), V552(N), D553(AGST), I554(EHMPQS), E555(AGHNSTVY), 555.5(N), K556(ACDEFGHMQTW), V557(L), M558(ADNSTV), 558.5(E), I559(C), 559.5(A), T560(AV), 560.5(A), D561(EFLY), E562(AD), E563(FITVY), I565(T), R566(ACDEFGHILMNQSTVWY), T567(Q), 567.5(E), T568(PV), 569.5(M), P570(CQS), 570.5(M), V571(ACDEFHLMQSTY), 571.5(G), A572(CGSY), 572.5(VWY), T573(ACDGINSVW), 573.5(MT), | |

TABLE 8-continued

Amino acid alterations that reduce delivery to spleen.

| Amino acid alteration | Fold increase of efficiency |
| --- | --- |
| E574(ADLMQS), 574.5(DV), Q575(-CDGIKLMNSTVWY), 575.5(AFWY), Y576(ACFGHIMSV), 576.5(EFWY), G577(DW), 577.5(ACDEHIMNQSTV), S578(DEFGHILNVWY), 578.5(ACDEFGHILNSTVY), V579(ACDEFGHLMNQSTWY), 579.5(ACDEFGILMNPQSTVWY), S580(-DEFHILMNPQTVWY), 580.5(ACDEFGKLMNPQRSTVWY), T581(-CDEFGHKLNPWY), 581.5(ACDEFGILMNPQTVWY), N582(-ACDEFGHIKLMPQRSTVWY), 582.5(DFGHNPSTVW), L583(-ADEGIPQST), 583.5(DEGIMNPQSTVY), Q584(-ADEFGHILMNPSTVWY), 584.5(ACDEFGHILMNPQSTVWY), R585(-ACDEFGHIKLMNPQSTVWY), 585.5(ADEFGHILMNPQSTVWY), G586(-DEFHLMNSVWY), 586.5(ACDEFGHILMNPQSTVY), N587 (-DEFGHILMPQSTVY), 587.5(ADEFGILMNPQSTVWY), R588 (-ACDEFGHIKLMNPQSTVWY), 588.5(ADEFGHILMNPQSTVY), Q589 (-DEIPRW), 589.5(ACDEFGHIKLMNPQSTVWY), A590(DEFHIKLMNQTWY), 590.5(ACDEFGIKLMNPQSTVWY), A591 (-CDEFGILMNPTVWY), 591.5(ACDEFGHILMNPQSTVWY), T592 (-ACDEFGHLMNPQSVY), 592.5(ACDEFGILMNPQSTVWY), A593(-DEP), 593.5(ACDEFGHILMNPQSTVWY), D594(ELT), 594.5(ACDEFGHILMNPQSTVWY), V595(ACDEFGHLMNPQSTWY), 595.5(ACDEFGHILMNQSTVW), N596(ACDEGIMPQTW), 596.5(DENY), T597(DEHINPQV), 597.5(F), Q598(ACEFGHILMNSTVY), G599(CSW), 600.5(F), L601(WY), P602(MQ), M604(AS), 605.5(N), 606.5(P), 607.5(P), D608(W), R609(D), D610(Y), 610.5(F), Y612(R), 613.5(Y), Q614(T), I617(K), 617.5(I), K620(HMN), H623(L), F628(HIM), P630(GHI), L633(FHY), F637(Y), K640(W), 640.5(N), P644(W), I646(M), L647(I), N650(L), P652(S), 657.5(C), S658(CE), 658.5(CKR), T659(K), 659.5(CNQY), T660(CHP), 660.5(CFIW), F661(EQT), 661.5(CP), S662(W), 662.5(FHLMPQW), 663.5(CIMW), 664.5(C), K665(I), 665.5(NW), 666.5(V), A667(C), 667.5(HY), S668(N), T671(R), Q672(E), S674(G), V678(T), S679(EGIKY), E681(M), E683(H), E685(ALS), L686(T), Q687(I), 697.5(N), 701.5(A), N703(D), 703.5(EHLTY), Y704(H), 704.5(ADILNS), N705(DEK), 705.5(EQY), K706(DEGRST), S707(DEH), 707.5(MY), V708(CER), 708.5(I), N709(DER), 709.5(CGP), V710(EMNP), 710.5(D), D711(GN), 711.5(Y), T716(C), 720.5(N), E722(D), P723(CEQ), R724(W), P725(M) | |
| A2(C), 3.5(DNTV), 4.5(DGHY), G5(Y), D9(G), W10(Y), 10.5(HI), E12(HIK), L15(H), S16(Q), I19(T), R20(GINQ), Q21(GK), 21.5(F), 22.5(Y), W23(DFKM), 23.5(F), K24(C), 24.5(DIN), L25(GR), 25.5(CVW), P27(T), 28.5(AEGINV), P29(ACEF), P30(Y), 30.5(GIKN), P31(H), 31.5(AY), P32(CIKS), P34(Q), 34.5(CV), A35(PY), 35.5(CGHNY), E36(CQ), 36.5(K), R37(F), 37.5(EMP), H38(ADE), 38.5(ADEFGKVY), K39(-AEPV), 39.5(DEHN), D40(-PY), 40.5(DEST), D41(A), 41.5(NQ), S42(-EHLQV), 42.5(KY), R43(GW), 43.5(DVY), 45.5(M), G49(HMQY), Y50(H), 50.5(N), Y52(D), 53.5(R), P55(Y), 55.5(E), F56(AV), G58(CT), 58.5(F), L59(CIR), 59.5(H), D60(NY), K61(C), 61.5(K), G62(Q), E63(CMV), E67(PV), A70(I), A71(NTY), L73(KNVY), E74(DFI), A78(CKQ), 78.5(AQ), Y79(-), R81(K), Q82(-HKM), 82.5(DK), L83(N), 83.5(DHNY), D84(IT), 84.5(N), S85(D), 85.5(HK), G86(-DH), 86.5(Q), D87(EKQ), 87.5(AHQ), N88(AI), 90.5(Y), L91(QY), K92(N), 92.5(D), Y93(G), N94(Q), D97(-), A98(N), 98.5(E), E99(DK), 99.5(K), Q101(DY), L104(C), 104.5(E), K105(MV), 105.5(HRW), E106(HN), 106.5(WY), D107(-QW), 107.5(EP), 108.5(W), S109(FKY), 109.5(D), F110(VY), 112.5(C), N113(CDW), 113.5(FN), L114(HNQ), G115(M), 115.5(A), 116.5(DEP), A117(NQY), 117.5(CKW), V118(K), F119(QY), 119.5(H), Q120(N), 120.5(K), 121.5(K), K122(-DFR), 122.5(EIKP), K123(CENW), 123.5(N), R124(-), 124.5(EK), 125.5(C), 126.5(A), E127(-F), 127.5(DIY), P128(F), 128.5(T), L129(CKW), G130(C), 130.5(D), L131(NV), 131.5(EHR), E133(FW), E134(K), 134.5(A), P135(Q), 135.5(DM), V136(Y), 136.5(CM), 137.5(Q), 139.5(R), P140(H), 140.5(N), G141(CK), 141.5(Q), K142(CH), 142.5(CEGW), 143.5(K), R144(NW), 144.5(RY), P145(AR), 145.5(KMY), 146.5(N), 147.5(EH), H148(CNW), 148.5(EMN), S149(W), 149.5(HM), P150(-M), 150.5(CDM), V151(D), E152(-DH), 152.5(CHK), P153(W), S156(T), 156.5(T), S157(EKNY), 157.5(CNPQ), G158(D), T159(C), 159.5(V), G160(C), 160.5(CDN), K161(CDHNTWY), 161.5(EHN), A162(-H), 162.5(ACSVY), G163(CFNPT), 163.5(CN), Q164(DM), 164.5(CEY), Q165(HW), 165.5(ITV), P166(AILS), 166.5(GN), N172(Y), 173.5(FI), G174(CFHS), Q175(DKT), 175.5(CILPRTW), T176(CGNRS), 176.5(GN), G177(-EQ), 177.5(IP), D178(NQW), 178.5(DGINW), 179.5(CDN), D180(CM), 180.5(ACM), S181(QRWY), 181.5(EIKLNPWY), V182(CGNW), 182.5(CFLPRW), P183(CS), 183.5(EIMY), D184(HNVY), 184.5(MY), P185(-DEIV), 185.5(D), Q186(NP), 186.5(CIK), P187(-CHK), 187.5(V), 188.5(Y), G189(-), 189.5(MQ), Q190(MTW), 190.5(DFMN), P191(CQ), 191.5(W), P192(CKMQW), 192.5(CMN), A193(CDFLM), 193.5(DGHLMNPW), A194(CKMRW), 194.5(CDM), P195(AKMNQR), 195.5(EMQY), S196(-HW), G197(AT), L198(-CDGINRV), G199(V), | 0.9-fold |

TABLE 8-continued

Amino acid alterations that reduce delivery to spleen.

| Amino acid alteration | Fold increase of efficiency |
| --- | --- |
| 199.5(CFHW), T200(IQV), N201(DHV), T202(NS), M203(ACDPR), A204(D), T205(IKR), G206(DEF), S207(D), G208(E), A209(ENP), P210(KQS), D213(LTW), N214(CEILY), N215(DFIM), E216(A), G217(CEFHLMVY), A218(PQ), G220(CNT), V221(I), N223(CHMY), S225(CQR), N227(D), H229(DSTV), D231(C), T233(DHL), M235(V), G236(V), 236.5(D), D237(C), 237.5(DGHKNQS), R238(CH), 238.5(FT), I240(CRW), T242(R), T244(C), A248(V), L249(V), P250(Q), T251(LV), N254(CGQ), H255(ANT), L256(ACGHMNQRSV), K258(LQ), Q259(CGHKPRS), I260(M), 260.5(ACDEMQST), S261(CDG), 261.5(S), S262(T), 262.5(DEGINST), Q263(-ADFGHWY), 263.5(DG), S264 (-DEFGHLWY), 264.5(D), G265(-), 265.5(ADET), 266.5(AE), S267(ENT), 267.5(E), N268(ADEQ), 268.5(E), 269.5(D), N270(ACDGHQSY), H271(EFIN), F273(HMWY), S276(ACT), G280(A), Y281(F), F282(WY), F287(Y), H288(N), C289(A), D295(AE), R307(CNST), 307.5(K), P308(-W), K309(ACQS), R310(FILW), L311(AFIY), N312(LM), F313(CI), K314(CGHLMQSVWY), I318(F), T324(CL), 324.5(CKR), Q325(CHIKRV), 325.5(I), N326(CDLM), 326.5(M), D327(T), G328(AHNS), T329(ACI), T330(KQ), T331(ALY), I332(ACS), 332.5(K), A333(CD), N334(Q), T339(C), V342(AIL), T344(DFILM), S346(FIPW), Y348(ADMNRS), Q349(AGS), V353(CT), L354(AHT), G355(AS), S356(A), Q359(EGHM), F365(W), A367(P), V369(P), F370(Y), M371(AFS), V372(C), Q374(N), Y375(W), Y377(F), L378(A), T379(ACGV), 379.5(DE), L380(ENQTY), 380.5(E), N381(ACDGMQS), N382(CDE), 382.5(D), 383.5(E), 384.5(D), Q385(ENPRSTW), 385.5(AEHPT), A386(EHLNPRTVW), 386.5(CDEP), V387(CDELM), 387.5(EGKP), G388(IM), R389(AGILMPQSTVY), 389.5(N), S390(DGNT), S391(A), 394.5(N), Y397(AN), P399(EIMQ), Q401(CDIMRVW), L403(M), R404(K), 404.5(N), T405(S), G406(DEN), N408(DGHLM), 408.5(CN), F409(CHY), T410(H), F411(LQSTV), S412(CEFGILW), Y413(MW), T414(FGQ), 414.5(D), 415.5(ADGHMNQS), E416(AGP), 416.5(CEGMNR), D417(EFHILMNS), 417.5(ACEHKLMQRT), V418(GIMQST), P419(DEGHIKLNQVWY), F420(L), Y424(CT), 424.5(F), A425(-GQV), H426(N), S427(ACD), Q428(EHNS), S429(CPY), L430(IM), D431(FM), 431.5(Y), R432(-I), L433(DIQV), 433.5(F), M434(A), L437(ACHMNSTY), I438(GKNT), D439(HKNPSTY), 441.5(M), L442(CFIT), Y444(FH), 444.5(CLM), L445(CFMVY), 445.5(ACDEGHILMNQSTVY), S446 (-CDEGHIKLMNQTV), 446.5(ACDEFGHILMNPQSTVWY), R447 (-ACDEFGHILMNPQSTVWY), 447.5(ACDEFGHILMNPQSVWY), T448 (-ACDEFGHILMNPQSVWY), 448.5(ACDEFGHILMNPQSWY), N449 (-ACDEFGILMPQSTVWY), 449.5(AEGHLMNPSTVY), T450 (-CDEGHPQW), 450.5(ADEFGHLMPQSTV), P451(-I), 451.5(GNP), S452 (-DEFHILNPQVW), 452.5(AILPV), G453(-ADEFHIKLMNPQSTV), 453.5(FILMNTVY), T454(-DEFHILMNPV), 454.5(ADEFGLMPSTY), T455(-ADEILMNPQVY), 455.5(AFHLNPQSTY), T456 (-DEFGHIKLMNPQ), 456.5(ADEGHILMNPQSV), Q457(-ADEFGHILP), 457.5(ADEFGHILMNPSVWY), S458(-CDEFHMNTVWY), 458.5(CDEFGHILMNPSTVWY), R459(-ACDEFGHILMNPQSTVWY), 459.5(DEP), L460(ACFHIMNPSTVWY), 460.5(W), Q461(CDEIKTVW), F462(Y), 462.5(N), S463(ACDGKNQRTV), 463.5(F), Q464(AFILRSTV), 464.5(SY), A465(CGP), G466(CQ), 466.5(E), A467(DFGHIKLMRVY), S468(CDEFLMQRV), D469(V), 469.5(DE), I470(FLM), R471(ACDEGKMQSTV), D472(LMY), Q473(FHMSY), S474(IY), R475(H), 475.5(SW), N476(CSTW), 476.5(L), W477(Y), 477.5(L), L478(FI), 478.5(L), P479(GIT), 479.5(D), G480(Y), P481(ACV), 481.5(GHY), C482(FGIMNQTWY), 482.5(FM), Y483(ACFHIMTVW), 483.5(FQV), R484(EFGHIKLMNQSTVY), 484.5(N), Q485(ACFGHILMNSTVY), 485.5(EIKMQY), Q486(ACDEFGILMNPSTVWY), 486.5(CFV), R487 (-ACDEFGHIKLMNPQSTVWY), 487.5(FW), V488(ACEFGHLMNQTWY), 488.5(ACDEFGILMPQSVWY), S489(-ACDEFGHIKLMNPQTVWY), 489.5(ACDEGLMPQRSTVWY), K490(-ACDEFGHILMNPQRSTVWY), 490.5(ACDEFGHILMNPQRSTVWY), T491(-ADEGPSWY), 491.5(ACDEFGHIKLMNPQSTVWY), S492(-CDEFGILMNQ), 492.5(ADEGHILMPQSTVY), A493(-DEFHILNPQRVWY), 493.5(ADEFGHIKLMNPQSTVWY), D494(EFR), 494.5(ADEGHILMNPSTVWY), N495(-ADEFGHILMPQSTVWY), 495.5(ACDEFGILMPQSTVWY), N496(-ACDEFGHILMPQSTVWY), 496.5(ADEFGHILMPQSTVWY), N497(-ACEFGHILMPSTVWY), 497.5(ADEFGILMPQTVY), S498(-CDEFGILMNPQRTVWY), 498.5(ADEFGILMNPQSTVWY), E499(CDIPQS), 499.5(ACDEGHILMNPQRSTVWY), Y500(-ACDEGHIKLMNPQSTV), 500.5(ADEFGHILMNPQSTVWY), S501(-ACDEFGILMNPQRTVWY), 501.5(ACDEFGHILMNQRSTVWY), W502(-ACDEFGILMPQSTVY), 502.5(ADEFGHILMNPQSTVWY), T503(-ADEFGHILMNPQVWY), 503.5(ADEFGILMNPQSTVW), G504(-ACDEFHILMNPQSTVWY), | |

TABLE 8-continued

| Amino acid alterations that reduce delivery to spleen. | |
|---|---|
| Amino acid alteration | Fold increase of efficiency |
| 504.5(ACDEFGHILMNPQSTVWY), A505(-CDEFGHILMNPQSTVWY), 505.5(ACDEFGILMPQSTVWY), T506(-ACFGILMNPQV), 506.5(ACIPSTVW), K507(-ACEFHILMNQRSTVWY), Y508(-DMST), H509(CEFNQ), 509.5(K), L510(I), 510.5(K), N511(ACDEGLMQSWY), 512.5(S), R513(CHIV), D514(ACEFGILMQSTV), S515(CV), L516(ACIMSTV), V517(CIL), 517.5(C), N518(CILQRTV), P521(CFLMNST), 521.5(MS), A522(CV), M523(CLQV), 523.5(A), A524(CGPST), 524.5(ACGHSTW), S525(ACGHMNPT), 525.5(ACDEFGHILMNPQSTVWY), H526(-ACDEFGIKLMNPQSTVWY), 526.5(ACDEFGHILMNPQSTVWY), K527(-DEFGHILMPQRSTVWY), 527.5(ACDEFGHILMPQSTVWY), D528(AEFMPQSVW), 528.5(DEPT), D529(ES), 529.5(ADEGLMNPQTV), E530(DNPVW), 530.5(ACDEFGHIKLMNQRSTVWY), E531(ACFGHILMNPQSTVY), 531.5(ADEFGIKLMNPQRSTVY), K532(-ACDEFGHILMNPQRSTVWY), 532.5(ACDEFGHIKLMNPQSTVWY), F533(ACDEGHILMNQSTVW), 533.5(ACDEFGHILNPQSTVWY), F534(ILMVWY), 534.5(F), P535(-AF), Q536(-ACDEFGHIMNPSTVWY), 536.5(ACILTV), S537(-ACDFGNQTY), 537.5(T), G538(-), V539(AHILMNQST), L540(IM), 540.5(EKMN), I541 (-ADEFGPQRTVY), 541.5(DEGPQST), F542(GKP), 542.5(QY), G543(FPS), 543.5(ACDHIKLMPQRSTVY), K544(-ACFGHILMNPQSTVY), 544.5(ACDEFGHIKLMRSTVWY), Q545(-ADFKLPVW), 545.5(ACDFGHILMNPQSTVWY), G546(ACDEFHILMNPQSTVWY), 546.5(ACDEFGHILMNPQSTVWY), S547(-DEFGHILMPQWY), 547.5(ACDEFGHILMNPQSTVWY), E548(FILNPQY), 548.5(ACDEFGHILMNPSTWY), K549(-DFGHILPQSTVWY), 549.5(ADEFGHLMNQSTV), T550(-ACDRW), 550.5(ADIKMNPRSTV), N551(ACDEGHIKLMPQRSTVY), 551.5(ACDEHILMNPSTV), V552(ACELNST), 552.5(VW), D553(AGST), I554(ACEFHLMPQSTW), E555(AGHNSTVY), 555.5(N), K556(ACDEFGHLMQSTVW), 556.5(Q), V557(L), M558(ACDINQSTVWY), 558.5(E), I559(CQV), 559.5(A), T560(ACSV), 560.5(A), D561(AEFLQRY), E562(AD), E563(AFHIMRTVY), I565(T), R566(ACDEFGHILMNQSTVWY), T567(PQ), 567.5(E), T568(PV), 569.5(M), P570(CQS), 570.5(M), V571(ACDEFHILMQSTY), 571.5(G), A572(CGSY), 572.5(VWY), T573(ACDGHINSVW), 573.5(MT), E574(ACDFLMQSW), 574.5(DV), Q575(-ACDFGHIKLMNSTVWY), 575.5(AFWY), Y576(ACFGHIMSVW), 576.5(EFWY), G577(DW), 577.5(ACDEHIMNQSTV), S578(DEFGHILNQVWY), 578.5(ACDEFGHILNSTVY), V579(ACDEFGHLMNQSTWY), 579.5(ACDEFGILMNPQSTVWY), S580(-DEFHILMNPQTVWY), 580.5(ACDEFGHIKLMNPQRSTVWY), T581(-CDEFGHKLNPWY), 581.5(ACDEFGILMNPQTVWY), N582 (-ACDEFGHIKLMPQRSTVWY), 582.5(DFGHNPSTVW), L583 (-ADEGIPQSTVW), 583.5(DEGIMNPQSTVY), Q584 (-ADEFGHILMNPSTVWY), 584.5(ACDEFGHILMNPQSTVWY), R585 (-ACDEFGHIKLMNPQSTVWY), 585.5(ADEFGHILMNPQSTVWY), G586(-DEFHLMNQSTVWY), 586.5(ACDEFGHILMNPQSTVY), N587 (-DEFGHILMPQSTVY), 587.5(ADEFGILMNPQSTVWY), R588 (-ACDEFGHIKLMNPQSTVWY), 588.5(ADEFGHILMNPQSTVY), Q589 (-ADEFIPRSTVW), 589.5(ACDEFGHIKLMNPQSTVWY), A590(DEFGHIKLMNQTWY), 590.5(ACDEFGIKLMNPQSTVWY), A591(-CDEFGILMNPQTVWY), 591.5(ACDEFGHILMNPQSTVWY), T592(-ACDEFGHLMNPQSVY), 592.5(ACDEFGILMNPQSTVWY), A593(-DELPY), 593.5(ACDEFGHILMNPQSTVWY), D594(ELT), 594.5(ACDEFGHILMNPQSTVWY), V595(ACDEFGHLMNPQSTWY), 595.5(ACDEFGHILMNQSTVW), N596(ACDEFGIMPQSTWY), 596.5(DENY), T597(DEGHINPQRVW), 597.5(F), Q598(ACEFGHILMNSTVY), G599(CSW), 600.5(F), L601(VWY), P602(CMQ), M604(AQS), V605(N), 605.5(N), 606.5(P), 607.5(P), D608(W), R609(D), D610(Y), 610.5(F), Y612(R), 613.5(Y), Q614(CT), I617(K), 617.5(I), A619(CG), K620(ACHMNQS), I621(AHLR), H623(EKL), D625(S), G626(A), H627(VY), F628(HILM), P630(AGHIQSTV), 630.5(C), S631(N), L633(FHMY), M634(C), F637(IWY), L639(V), K640(FPVW), 640.5(N), H641(C), P644(WY), Q645(ILMTV), I646(MT), L647(I), I648(AC), N650(LTV), P652(AS), V653(T), 655.5(IW), N656(FT), 657.5(CDHIS), S658(CEFKMQ), 658.5(CFGHKLMQRW), T659(DKRS), 659.5(CELMNQRY), T660 (-CFHKLP), 660.5(CEFHIPRW), F661(AEILQT), 661.5(CDELPQRSW), S662(NPW), 662.5(ACDFHKLMPQTVW), A663(HY), 663.5(CDEGIMNW), A664(CEHK), 664.5(CDGPRTV), K665(CGILSVWY), 665.5(HIMNPRVW), F666(C), 666.5(IVY), A667(CP), 667.5(HQY), S668(N), F669(Y), I670(V), T671(R), Q672(EL), S674(G), T675(AL), Q677(C), V678(AIT), S679(EFGHIKMRY), V680(L), E681(LMNT), I682(MV), E683(HILM), E685(ADLST), L686(CT), Q687(FIKMW), E697(-DLPR), 697.5(CGHNPSW), I698(V), 699.5(E), Y700(F), T701(S), 701.5(A), S702(CNV), 702.5(Q), N703(D), | |

TABLE 8-continued

| Amino acid alterations that reduce delivery to spleen. | |
|---|---|
| Amino acid alteration | Fold increase of efficiency |
| 703.5(AEHLTY), Y704(H), 704.5(ADEILNST), N705(CDEKMPW), 705.5(ENQY), K706(DEGRST), S707(CDEFH), 707.5(MY), V708(CEFGHMNRW), 708.5(I), N709(CDEGPR), 709.5(CGPQ), V710(EMNPQ), 710.5(D), D711(AGNP), 711.5(QY), T713(C), T716(CEFMPRVWY), N717(ER), V719(CFIKNR), 720.5(N), S721(FKLMQRTVW), E722(DQ), P723(CDEQSV), R724(FHSW), P725(ALMQ), I726(V), L735(CI), 735.5(LMV) | |

TABLE 9

| Amino acid alterations that reduce delivery to blood. | |
|---|---|
| Amino acid alteration | Fold increase of efficiency |
| S264(W), 444.5(M), S446(D), R471(G), P479(G), 479.5(D), C482(Y), Y483(ACHV), Q485(AGS), 485.5(K), 487.5(F), 488.5(W), 502.5(Y), 504.5(NW), A505(Y), 505.5(AQTVW), T506(FL), 506.5(AV), N518(R), 524.5(S), 525.5(ANQTY), 526.5(FHMY), 527.5(HW), Q536(-), S537(-), G538(-), V539(H), A572(Y), T573(G), Y576(ACGH), V579(G), V595(DGHNQY), 595.5(H), Q598(GNY), L601(W) | 0.1-fold |
| S264(W), 266.5(E), 268.5(E), 379.5(E), 444.5(M), S446(D), N449(C), 454.5(E), R459(C), F462(Y), 469.5(E), R471(AEGQSTV), 475.5(W), P479(GT), 479.5(D), G480(Y), C482(GY), Y483(ACHIQTV), R484(K), 484.5(N), Q485(AGNST), 485.5(K), 487.5(F), V488(G), 488.5(PW), 491.5(W), S492(C), 498.5(DE), 499.5(ADLMNPQ), 500.5(LNQST), 501.5(ACHNS), W502(-AE), 502.5(AGMNPTY), 503.5(AGILMNQT), G504(W), 504.5(AGHMNQVWY), A505(HLY), 505.5(AGLMQTVW), T506(FGILMP), 506.5(ACISV), K507(HIW), H509(E), D514(GIV), N518(R), P521(M), 523.5(A), 524.5(AS), S525(H), 525.5(AFHILNQSTY), H526(IPV), 526.5(AFHMNQSTY), 527.5(CFHIMQVWY), 530.5(C), 531.5(I), 532.5(P), F534(VY), P535(-F), Q536(-P), S537(-DFQ), G538(-), V539(H), P570(Q), A572(Y), T573(AG), E574(F), Q575(L), Y576(ACGHS), S578(D), V579(EGMNQ), S580(Q), N582(F), Q589(P), V595(DEGHLMNPQTWY), 595.5(ADHIQSTW), 596.5(N), T597(GLP), Q598(CEFGNSY), G599(C), L601(W), 640.5(N) | 0.2-fold |
| S264(W), 266.5(E), 267.5(E), 268.5(E), N270(AGHSY), 379.5(E), 380.5(E), 431.5(Y), 433.5(F), 444.5(CLM), L445(Y), 445.5(ACLMSTY), S446(DEIL), 446.5(ALPQ), R447(I), 447.5(PW), T448(ILPQW), 448.5(CP), N449(CP), S452(D), 454.5(DE), T455(E), Q457(E), S458(D), 458.5(CW), R459(CDV), 460.5(W), Q461(D), F462(Y), D469(M), 469.5(E), R471(ACEGMQSTV), Q473(Y), S474(I), 475.5(SW), 477.5(L), P479(GT), 479.5(D), G480(Y), C482(FGY), 482.5(M), Y483(ACHIQTV), 483.5(Q), R484(K), 484.5(N), Q485(ACGNSTV), 485.5(KQY), 487.5(F), V488(FGY), 488.5(MPQW), S489(FQY), K490(DEFGHNQWY), 490.5(CPQ), 491.5(W), S492(C), 495.5(W), N496(M), S498(DE), 498.5(DE), 499.5(ADEGLMNPQST), Y500(-NP), 500.5(AGLMNPQST), S501(-CIL), 501.5(ACGHILNQSTVY), W502(-ACEV), 502.5(AFGILMNPSTVY), T503(EP), 503.5(AGILMNPQSTVW), G504(-IPW), 504.5(AFGHILMNPQSVWY), A505(FHILMPWY), 505.5(AGILMPQSTVWY), T506(FGILMNP), 506.5(ACISTV), K507(ACHINQSW), H509(EFN), N511(E), R513(C), D514(AGIV), L516(AST), 517.5(C), N518(R), P521(M), 523.5(A), 524.5(AS), S525(HM), 525.5(ACFHILMNQSTVWY), H526(-EGIKMPQV), 526.5(ACFGHLMNQSTVY), 527.5(ACDEFGHILMPQSTVWY), 528.5(DE), 529.5(DP), E530(P), 530.5(CILM), 531.5(IV), 532.5(P), F533(T), F534(VY), P535(-F), Q536(-DPW), S537(-DFGNQY), G538(-), V539(H), 559.5(A), T568(P), P570(Q), 570.5(M), V571(AHQS), A572(Y), T573(ACDG), E574(FLW), Q575(DGL), 575.5(W), Y576(ACGHS), 576.5(W), 577.5(HS), S578(DEFGL), 578.5(L), V579(EGHMNQ), S580(Q), N582(FWY), 585.5(A), 586.5(P), Q589(P), 593.5(P), V595(ACDEGHLMNPQTWY), 595.5(ADFHILMQSTW), 596.5(DN), T597(EGILMPV), Q598(CEFGNSTY), G599(C), L601(WY), L633(FY), 640.5(N) | 0.3-fold |
| D180(M), 183.5(M), L256(S), S261(D), Q263(V), S264(W), 265.5(DE), 266.5(E), S267(E), 267.5(E), 268.5(E), 269.5(D), N270(ACDGHSY), H271(E), 379.5(DE), L380(E), 380.5(E), N382(D), 382.5(D), 383.5(E), 386.5(D), Q428(E), D431(M), 431.5(Y), R432(I), L433(D), 433.5(F), L437(Y), Y444(FH), 444.5(CLM), L445(FY), 445.5(ACGHLMQSTVY), S446(DEILV), 446.5(AFILPQSTVWY), R447(CEGILMQTV), 447.5(CFGIMPWY), T448(FGILNPQVWY), 448.5(CFLPW), N449(CDEFP), T450(CE), S452(D), 454.5(DE), T455(E), 456.5(D), Q457(DE), 457.5(D), S458(CDEW), 458.5(CDEMWY), | 0.5-fold |

TABLE 9-continued

Amino acid alterations that reduce delivery to blood.

| Amino acid alteration | Fold increase of efficiency |
|---|---|
| R459(ACDEILMPQSTV), L460(NSTWY), 460.5(W), Q461(DE), F462(Y), S463(G), 463.5(F), Q464(KSV), 464.5(S), A465(CGP), A467(GY), S468(C), D469(CEMQRSV), 469.5(E), I470(FL), R471(ACDEGMQSTV), Q473(FMY), S474(I), 475.5(SW), N476(TW), 477.5(L), L478(F), P479(GT), 479.5(D), G480(Y), 481.5(Y), C482(FGY), 482.5(FM), Y483(ACHILMQTV), 483.5(FQ), R484(K), 484.5(N), Q485(ACGHILNSTVY), 485.5(EKQY), Q486(FIV), 487.5(FW), V488(EFGHLNWY), 488.5(FILMPQW), S489(FGILQVY), 489.5(DP), K490(ACDEFGHILMNQSTVWY), 490.5(CIPQV), T491(E), 491.5(FIMW), S492(CE), 492.5(DL), A493(DE), 493.5(KP), N495(AFLQTVY), 495.5(FILPVW), N496(AFGHILMW), N497(-I), 497.5(DE), S498(-DELMR), 498.5(DEGLQ), E499(I), 499.5(ADEGHILMNPQSTV), Y500(-ACEGKLNPQS), 500.5(AFGHILMNPQST), S501(-CILNV), 501.5(ACFGHILMNQRSTVWY), W502(-ACEGILMQSVY), 502.5(AFGHILMNPQSTVWY), T503(-ADEP), 503.5(AFGILMNPQSTVW), G504(-CILNPSVWY), 504.5(AFGHILMNPQSVWY), A505(EFHILMNPQVWY), 505.5(ACFGILMPQSTVWY), T506(FGILMNPV), 506.5(ACISTV), K507(ACHILMNQSVW), Y508(-), H509(EFN), L510(I), N511(DELMW), 512.5(S), R513(CIV), D514(ACGILMQTV), L516(ACSTV), V517(L), 517.5(C), N518(LR), P521(CFLMNS), 521.5(S), 523.5(A), 524.5(ACST), S525(HMP), 525.5(ACFGHILMNQSTVWY), H526(-ACDEFGIKMNPQSTVWY), 526.5(ACDEFGHLMNPQSTVY), K527(-), 527.5(ACDEFGHILMPQSTVWY), 528.5(DEPT), 529.5(ADEMNPTV), E530(P), 530.5(CDEFGHILMNQSTVWY), 531.5(ADFGINPQTVY), 532.5(HPSTW), F533(ACILQSTV), 533.5(Y), F534(ILVY), 534.5(F), P535(-AF), Q536(-DPWY), S537(-CDFGNQTY), G538(-), V539(H), 542.5(Y), G543(S), 543.5(Y), K544(FNQY), S547(-), K549(IW), 549.5(E), T550(CD), N551(DE), 551.5(DE), V552(NS), I554(E), V557(L), 558.5(E), 559.5(A), R566(ADEFGILMNTVWY), 567.5(E), T568(P), 569.5(M), P570(Q), 570.5(M), V571(ACHMQS), 571.5(G), A572(CY), T573(ACDGNSV), 573.5(M), E574(DFLMW), 574.5(V), Q575(DGKLMNV), 575.5(AWY), Y576(ACGHIS), 576.5(FWY), 577.5(AHMNS), S578(DEFGILWY), 578.5(AGHLNST), V579(ACEFGHMNQST), 579.5(L), S580(-MNQ), T581(ENP), N582(FILWY), 585.5(AGIMPQSTVY), 586.5(AGPQ), 587.5(MNQV), 588.5(LMV), Q589(APV), 589.5(PV), 590.5(CP), A591(DT), 591.5(FILP), T592(-DGN), 592.5(CGMS), A593(-D), 593.5(APSW), D594(E), 594.5(AGQST), V595(ACDEFGHLMNPQSTWY), 595.5(ADEFHILMQSTW), N596(CETW), 596.5(DEN), T597(DEGIKLMPQRV), Q598(ACEFGHNSTY), G599(C), L601(WY), P602(M), M604(A), 605.5(N), 607.5(P), 610.5(F), L633(FHY), 640.5(N), 662.5(W) | |
| D41(H), 41.5(D), S42(E), R43(T), 43.5(DT), 45.5(M), K51(Y), G58(ET), K61(-), E63(M), 107.5(E), D180(M), 180.5(M), 183.5(M), L256(ACS), 260.5(AEM), S261(D), S262(T), 262.5(DE), Q263(VW), S264(DEW), 264.5(D), 265.5(DE), 266.5(E), S267(E), 267.5(E), N268(ADEQ), 268.5(E), 269.5(D), N270(ACDGHQSY), H271(E), R307(MN), P308(M), 324.5(C), 326.5(M), Q359(DET), 379.5(DE), L380(E), 380.5(E), N381(D), N382(DE), 382.5(D), 383.5(E), 384.5(D), A386(E), 386.5(CDE), V387(E), 387.5(P), G388(E), 394.5(N), 408.5(C), 424.5(F), Q428(EH), S429(Y), D431(M), 431.5(Y), R432(I), L433(D), 433.5(F), L437(HY), L442(FI), Y444(FH), 444.5(CLM), L445(CFMY), 445.5(ACGHLMNQSTVY), S446(CDEGHILMTV), 446.5(AFHILNPQSTVWY), R447(ACEFGILMNQSTV), 447.5(CFGIMPVWY), T448(CFGILMNPQVWY), 448.5(CEFILPWY), N449(ACDEFGIMPSVW), T450(CE), S452(DE), T454(DEFI), 454.5(DE), T455(DE), T456(D), 456.5(D), Q457(DEIL), 457.5(DE), S458(CDEFMPVW), 458.5(CDEFIMWY), R459(-ACDEFGHILMNPQSTVWY), L460(ANSTVWY), 460.5(W), Q461(DEGK), F462(Y), S463(CDGNQ), 463.5(F), Q464(ACIKLSTV), 464.5(S), A465(CGP), G466(AQ), A467(DFGPQY), S468(CP), D469(ACEMQRSTV), 469.5(DE), I470(FLM), R471(ACDEGKMQSTV), D472(Y), Q473(FHMY), S474(I), R475(K), 475.5(SW), N476(TW), W477(Y), 477.5(L), L478(FI), P479(GIT), 479.5(D), G480(Y), P481(A), 481.5(HY), C482(FGY), 482.5(FM), Y483(ACHILMQTV), 483.5(FQ), R484(K), 484.5(N), Q485(ACFGHILNSTVY), 485.5(EKQY), Q486(FGINSVWY), 486.5(F), R487(H), 487.5(FW), V488(AEFGHLMNQTWY), 488.5(CFGILMPQVWY), S489(-ACFGHIKLPQTVY), 489.5(DEP), K490(-ACDEFGHILMNQRSTVWY), 490.5(ACFHINPQTV), T491(DE), 491.5(ACFILMPQTVWY), S492(CDELM), 492.5(ADEGILV), A493(DELV), 493.5(IKLMPV), D494(R), 494.5(GIPV), N495(-AFLMPQSTVY), 495.5(AFGILPSVWY), N496(-ACFGHILMQSVW), N497(-EITV), 497.5(DEGLM), S498(-ADEFGILMPQRVWY), 498.5(DEFGLMQY), E499(I), 499.5(ADEGHILMNPQRSTVWY), Y500 | 0.7-fold |

TABLE 9-continued

Amino acid alterations that reduce delivery to blood.

| Amino acid alteration | Fold increase of efficiency |
| --- | --- |
| (-ACDEGIKLNPQST), 500.5(AEFGHILMNPQSTW), S501 (-ACILMNPTVW), 501.5(ACFGHILMNQRSTVWY), W502 (-ACEGILMPQSVY), 502.5(AFGHILMNPQSTVWY), T503(-ADEFGIPV), 503.5(AFGILMNPQSTVW), G504(-ACFILMNPSTVWY), 504.5(ACFGHILMNPQSVWY), A505(-EFHILMNPQTVWY), 505.5(ACFGILMPQSTVWY), T506(ACFGILMNPQV), 506.5(ACIPSTVW), K507(ACHILMNQSTVW), Y508(-D), H509(CEFN), 509.5(K), L510(I), N511(DELMQWY), 512.5(S), R513(CIV), D514(ACEGILMQSTV), L516(ACIMSTV), V517(L), 517.5(C), N518(ILQRTV), P521(CFLMNS), 521.5(S), A522(CV), 523.5(A), A524(CGP), 524.5(ACST), S525(ACHMP), 525.5(ACFGHILMNQSTVWY), H526(-ACDEFGIKLMNPQRSTVWY), 526.5(ACDEFGHILMNPQSTVY), K527(-HR), 527.5(ACDEFGHILMPQSTVWY), 528.5(DEPT), 529.5(ADEGLMNPTV), E530(P), 530.5(ACDEFGHILMNQRSTVWY), 531.5(ADEFGILMNPQSTVY), K532(R), 532.5(FHPSTVWY), F533(ACGHILMNQSTV), 533.5(FY), F534(ILMVWY), 534.5(F), P535 (-AF), Q536(-CDNPWY), S537(-CDFGNQTY), G538(-), V539(AHLMNQS), 540.5(M), 541.5(D), F542(P), 542.5(Y), G543(APS), 543.5(ACDILPSY), K544(-ACFGHILMNPQSTVY), Q545(D), 546.5(E), S547(-DEIMQ), 547.5(CDV), 548.5(CDE), K549(CDFGILMPQTVWY), 549.5(DE), T550(CDE), 550.5(DE), N551(CDE), 551.5(CDEN), V552(AELMNST), I554(CEHPQSTW), 555.5(N), K556(ADEGMNQTV), V557(LM), M558(ADTV), 558.5(E), I559(C), 559.5(A), T560(AV), 560.5(A), D561(AFMQVY), E562(AD), R566(ACDEFGHILMNTVWY), T567(Q), 567.5(E), T568(P), 569.5(M), P570(QS), 570.5(M), V571(ACHLMQS), 571.5(G), A572(CGSY), T573(ACDGINSV), 573.5(MT), E574(DFLMQW), 574.5(V), Q575(DGIKLMNTV), 575.5(AFWY), Y576(ACGHIS), 576.5(EFWY), 577.5(ACHIMNQSTV), S578(DEFGHILNVWY), 578.5(AFGHLNST), V579(ACEFGHLMNQST), 579.5(FL), S580(-MNPQ), T581(CENP), N582(FILMTVWY), 584.5(NT), R585(K), 585.5(AFGILMPQSTVY), 586.5(AGPQS), N587(GILMQTV), 587.5(AIMNQV), 588.5(ILMV), Q589(APSTV), 589.5(AFPV), A590(MQV), 590.5(ACPQT), A591(CDHIT), 591.5(AFGILMNPTV), T592(-CDGMNP), 592.5(ACFGILMPSTY), A593(-DE), 593.5(AFGNPSTW), D594(E), 594.5(AGQSTW), V595(ACDEFGHILMNPQSTWY), 595.5(ADEFHILMQSTVW), N596(CDEFGMPTW), 596.5(DEN), T597(CDEGHIKLMPQRV), Q598(ACEFGHINSTVY), G599(C), L601(WY), P602(M), M604(ACS), V605(F), 605.5(N), 607.5(P), 610.5(F), F628(I), L633(FHMY), 640.5(N), S658(C), 658.5(C), T660(C), 662.5(W), N703(D), N705(DE), K706(EST), S707(D), V708(C), N709(DE), P723(E), R724(FHNTWY) | |
| .5(D), P30(D), E36(N), 38.5(K), 40.5(D), D41(AHQW), 41.5(D), S42(EGQ), R43(T), 43.5(DHPSTV), 45.5(M), V46(I), G49(H), 50.5(N), K51(AY), G58(ET), K61(-), 61.5(K), E63(M), E74(H), 107.5(E), 135.5(M), 137.5(M), K142(I), 145.5(M), 150.5(M), 179.5(D), D180(M), 180.5(M), 183.5(M), 190.5(F), P192(M), 193.5(W), A194(C), H229(V), H255(N), L256(ACS), 260.5(ACDEMT), S261(D), S262(T), 262.5(DE), Q263(VW), 263.5(D), S264(DEFLW), 264.5(D), 265.5(DE), 266.5(E), S267(E), 267.5(E), N268(ADEQ), 268.5(E), 269.5(D), N270(ACDGHQSY), H271(E), R307(DMN), P308(GM), T324(C), 324.5(C), Q325(C), 326.5(M), T330(Q), G355(AS), Q359(ADEHTV), F370(Y), T379(A), 379.5(DE), L380(EY), 380.5(E), N381(CD), N382(DE), 382.5(D), 383.5(E), 384.5(D), Q385(CGW), 385.5(DP), A386(E), 386.5(CDEP), V387(E), 387.5(EGP), G388(E), R389(ALMPSTY), S390(DT), 394.5(N), 404.5(N), G406(M), 408.5(C), 415.5(Q), 417.5(M), Y424(C), 424.5(F), Q428(EHS), S429(Y), D431(M), 431.5(Y), R432(I), L433(D), 433.5(F), L437(AHNY), I438(CGNT), D439(K), L442(FI), Y444(FH), 444.5(CLM), L445(CFMVY), 445.5(ACGHLMNQSTVY), S446(CDEGHILMNTV), 446.5(AFGHILMNPQSTVWY), R447(ACEFGHILMNQSTV), 447.5(CFGILMNPVWY), T448(CFGILMNPQVWY), 448.5(CEFILMPWY), N449(ACDEFGILMPSVW), 449.5(PY), T450(CDE), S452(DEFLV), 452.5(I), G453(L), 453.5(I), T454(DEFILM), 454.5(DEF), T455(DEL), T456(D), 456.5(DE), Q457(ADEILMV), 457.5(DEW), S458(CDEFMPVWY), 458.5(CDEFILMWY), R459 (-ACDEFGHILMNPQSTVWY), L460(ACFHINPSTVWY), 460.5(W), Q461(CDEGKNTV), F462(Y), S463(ACDGNQV), 463.5(F), Q464(ACIKLMSTV), 464.5(S), A465(CGP), G466(ACDNQ), A467(CDFGHMPQY), S468(CEFLPQY), D469(ACEHMNQRSTV), 469.5(DE), I470(CFLM), R471(ACDEGKMQSTV), D472(Y), Q473(FHMSY), S474(I), R475(K), 475.5(SW), N476(STW), W477(Y), 477.5(L), L478(FI), P479(GIT), 479.5(D), G480(Y), P481(A), 481.5(HY), C482(FGQY), 482.5(FM), Y483(ACFHILMQTV), 483.5(FQ), R484(K), 484.5(N), Q485(ACFGHILNSTVY), 485.5(EKQY), Q486(FGINSVWY), 486.5(FV), R487(H), 487.5(FW), V488(ACEFGHLMNQTWY), | 0.8-fold |

TABLE 9-continued

| Amino acid alterations that reduce delivery to blood. | |
|---|---|
| Amino acid alteration | Fold increase of efficiency |
| 488.5(ACFGILMPQVWY), S489(-ACFGHIKLMPQTVY), 489.5(CDEPY), K490(-ACDEFGHILMNPQRSTVWY), 490.5(ACFGHIMNPQSTV), T491(ADEM), 491.5(ACFILMPQTVWY), S492(CDEILMT), 492.5(ADEGILMPSV), A493(DEILPRV), 493.5(DIKLMPV), D494(R), 494.5(GIMPTV), N495(-AFILMPQSTVY), 495.5(AFGILMPSTVWY), N496(-ACFGHILMQSTVW), 496.5(FT), N497(-EITV), 497.5(ADEGILMQT), S498(-ADEFGILMPQRVWY), 498.5(DEFGLMPQY), E499(I), 499.5(ADEGHILMNPQRSTVWY), Y500 (-ACDEGIKLMNPQST), 500.5(AEFGHILMNPQSTVW), S501 (-ACEGILMNPTVWY), 501.5(ACFGHILMNPQRSTVWY), W502 (-ACEGILMPQSVY), 502.5(AFGHILMNPQSTVWY), T503(-ADEFGIPSV), 503.5(AFGILMNPQSTVW), G504(-ACFILMNPQSTVWY), 504.5(ACFGHILMNPQSVWY), A505(-CEFGHILMNPQSTVWY), 505.5(ACFGILMPQSTVWY), T506(-ACFGILMNPQSV), 506.5(ACIPSTVW), K507(ACHILMNQSTVW), Y508(-DIMV), H509(CEFN), 509.5(K), L510(I), N511(ACDELMQWY), 512.5(S), R513(CHIV), D514(ACEGILMQSTV), S515(CIV), L516(ACIMSTV), V517(IL), 517.5(C), N518(CHILMQRTVY), P521(CFLMNST), 521.5(S), A522(CPV), M523(LV), 523.5(A), A524(CGPST), 524.5(ACHSTW), S525(ACGHMNP), 525.5(ACFGHILMNQSTVWY), H526 (-ACDEFGIKLMNPQRSTVWY), 526.5(ACDEFGHILMNPQSTVY), K527 (-HR), 527.5(ACDEFGHILMPQSTVWY), 528.5(DEPT), 529.5(ADEGLMNPTV), E530(P), 530.5(ACDEFGHIKLMNQRSTVWY), 531.5(ADEFGILMNPQSTVY), K532(-HRW), 532.5(FHIPSTVWY), F533(ACGHILMNQSTVW), 533.5(FHY), F534(ILMVWY), 534.5(F), P535(-AF), Q536(-CDFNPWY), 536.5(L), S537(-ACDFGNQTY), G538(-), V539(AHLMNQST), 540.5(KM), I541(DPY), 541.5(DGH), F542(P), 542.5(Y), G543(APS), 543.5(ACDHILPQSTVY), K544 (-ACFGHILMNPQSTVY), 544.5(DE), Q545(-DEP), 545.5(W), G546(DE), 546.5(EILMT), S547(-CDEFGHILMNPQV), 547.5(ACDHNPVY), 548.5(CDEMP), K549(-ACDEFGHILMNPQSTVWY), 549.5(DE), T550(CDE), 550.5(DEG), N551(CDELY), 551.5(CDEN), V552(ACELMNST), I554(CEHPQSTW), 555.5(N), K556(ACDEGLMNQSTVWY), 556.5(Q), V557(LM), M558(ACDHINQSTVW), 558.5(E), I559(CV), 559.5(A), T560(AV), 560.5(A), D561(AEFGHILMNQTVY), E562(AD), E563(D), I565(T), R566(ACDEFGHILMNQSTVWY), T567(Q), 567.5(E), T568(PV), 569.5(M), P570(CQS), 570.5(M), V571(ACHLMQST), 571.5(G), A572(CGSY), T573(ACDGINSV), 573.5(MT), E574(CDFLMQW), 574.5(DV), Q575(DFGIKLMNTVW), 575.5(AFWY), Y576(ACGHIS), 576.5(EFWY), 577.5(ACHIMNQSTV), S578(DEFGHILNVWY), 578.5(AEFGHILNST), V579(ACEFGHLMNQST), 579.5(FLY), S580 (-GMNPQ), T581(CEGKNP), N582(FILMTVWY), 583.5(Q), Q584(V), 584.5(FLNT), R585(K), 585.5(AFGILMPQSTVY), 586.5(AGMPQS), N587(GILMQTV), 587.5(AFIMNQV), 588.5(ILMV), Q589(APSTV), 589.5(AFPV), A590(GMPQV), 590.5(ACGPQST), A591(CDHIT), 591.5(AFGILMNPSTV), T592(-ACDGMNP), 592.5(ACFGILMNPSTY), A593(-DEN), 593.5(AFGNPSTW), D594(E), 594.5(AGHINQSTVWY), V595(ACDEFGHILMNPQSTWY), 595.5(ADEFHILMQSTVW), N596(CDEFGMPTW), 596.5(DEN), T597(CDEGHIKLMNPQRV), Q598(ACEFGHILMNSTVY), G599(CSW), L601(IWY), P602(M), M604(ACQS), V605(F), 605.5(N), 607.5(P), 610.5(F), K620(N), G626(A), F628(IM), P630(HIQ), L633(FHMY), 640.5(N), 657.5(C), S658(CE), 658.5(CQ), T660(C), 660.5(E), F661(LQ), S662(C), 662.5(FMW), A663(Y), 663.5(DM), 664.5(DE), A667(C), S674(E), 697.5(GN), N703(D), 703.5(E), N705(DE), K706(DEGST), S707(D), 707.5(Y), V708(CE), N709(DE), V710(E), 711.5(Y), T716(CE), N717(E), 720.5(N), S721(TV), E722(D), P723(CE), R724(FHNSTWY), 735.5(M) | |
| 3.5(DT), 4.5(N), Y6(I), D9(AV), R20(Q), K24(G), P27(T), P30(D), 32.5(L), P34(L), 34.5(V), 35.5(IN), E36(N), R37(Q), H38(L), 38.5(FK), K39 (-LPWY), 39.5(DP), D40(P), 40.5(DY), D41(AHKQTW), 41.5(DNV), S42(EGLQ), 42.5(AKNSTY), R43(AGPSTW), 43.5(DHPRSTV), 45.5(M), V46(IK), L47(F), P48(L), G49(HM), 50.5(N), K51(AMNY), P55(Y), 55.5(K), F56(V), G58(CEST), L59(AIQ), D60(N), K61(-Q), 61.5(K), G62(E), E63(CM), E67(DTV), A71(IT), L73(N), E74(DH), K77(Y), 78.5(Q), Q82(FM), 83.5(H), D84(I), D87(EQ), L91(W), K92(Y), A98(N), E99(K), Q101(IV), E102(QY), E106(H), D107(Q), 107.5(E), S109(N), F110(VY), R116(M), A117(N), A121(IL), L126(C), E127(F), L129(C), V132(AES), E133(-), 133.5(CFLPRSW), E134(-K), 134.5(W), 135.5(DEMW), 136.5(CNY), K137(L), 137.5(IM), 139.5(ADGT), P140(DHIT), 140.5(EN), G141(I), K142(CDEFHIT), 142.5(C), K143(-), P145(AY), 145.5(M), V146(NW), 146.5(DFNY), 147.5(DE), H148(DGNW), 148.5(E), 149.5(E), P150(DM), 150.5(DMP), V151(D), 151.5(WY), 152.5(M), S157(WY), K161(W), A162(H), T176(N), 177.5(IV), 178.5(D), 179.5(DN), D180(M), 180.5(M), S181(DF), 181.5(TWY), V182(W), P183(C), 183.5(LMY), | 0.9-fold |

TABLE 9-continued

| Amino acid alterations that reduce delivery to blood. | |
|---|---|
| Amino acid alteration | Fold increase of efficiency |
| P185(W), L188(Y), 188.5(EY), 189.5(Q), Q190(EW), 190.5(F), 191.5(W), P192(CMQW), 192.5(CDHM), A193(D), 193.5(DEPW), A194(CMW), P195(A), 195.5(TY), S196(FH), L198(C), N201(SV), 202.5(F), G206(E), G208(ET), A209(M), M211(V), N215(DI), G217(V), H229(DV), D231(C), S232(T), M235(V), T251(S), H255(N), L256(ACS), K258(LQ), 260.5(ACDEMQT), S261(DG), S262(T), 262.5(DEINT), Q263(EVW), 263.5(D), S264(DEFLMTW), 264.5(D), G265(-), 265.5(ADET), 266.5(AE), S267(ENT), 267.5(E), N268(ADEQ), 268.5(E), 269.5(D), N270(ACDGHQSY), H271(EIN), S276(T), H288(N), R307(-CDFMNS), 307.5(K), P308(-GMW), L311(I), N312(M), L315(I), T324(CL), 324.5(CL), Q325(CHIK), 325.5(I), 326.5(M), 327.5(P), G328(AHS), T329(CN), T330(Q), T331(L), I332(V), 332.5(K), L354(HT), G355(ACS), S356(N), Q359(ACDEGHNSTV), F370(Y), T379(ACV), 379.5(DE), L380(EY), 380.5(E), N381(CDGMQ), N382(DE), 382.5(D), 383.5(E), 384.5(D), Q385(CGSW), 385.5(ADEPTV), A386(CEFHNP), 386.5(CDEP), V387(DELM), 387.5(EGKP), G388(E), R389(ALMPQSTY), 389.5(N), S390(DT), 394.5(N), P399(EMQ), Q401(R), R404(K), 404.5(N), G406(M), 407.5(H), N408(HW), 408.5(C), F409(Y), T410(DHNY), S412(H), 412.5(Q), Y413(FW), T414(DK), 415.5(DQ), 416.5(EN), D417(NS), 417.5(KM), V418(IM), Y424(C), 424.5(F), A425(FGQ), S427(D), Q428(EHS), S429(CY), L430(I), D431(FM), 431.5(Y), R432(I), L433(ADMT), 433.5(F), L437(AHMNSY), I438(ACGHLNST), D439(K), L442(CFIV), Y443(F), Y444(FH), 444.5(CLM), L445(CFMVY), 445.5(ACGHILMNQSTVY), S446(ACDEGHILMNTV), 446.5(AFGHILMNPQSTVWY), R447(ACEFGHIKLMNQSTV), 447.5(CFGILMNPVWY), T448(ACFGILMNPQVWY), 448.5(ACEFILMPWY), N449(ACDEFGILMPSTVW), 449.5(PY), T450(CDEI), S452(DEFLV), 452.5(IV), G453(EL), 453.5(I), T454(DEFILM), 454.5(DEFL), T455(ADEL), T456(DP), 456.5(DEGLP), Q457(ADEILMSTV), 457.5(DEPW), S458(ACDEFMNPTVWY), 458.5(CDEFILMPTWY), R459(-ACDEFGHILMNPQSTVWY), L460(ACFHIMNPSTVWY), 460.5(W), Q461(CDEFGKMNTV), F462(Y), S463(ACDGMNQTV), 463.5(F), Q464(ACIKLMSTV), 464.5(S), A465(CGP), G466(ACDNQ), 466.5(E), A467(CDFGHIMPQSVY), S468(CEFILNPQVY), D469(ACEHMNQRSTV), 469.5(DE), I470(CFLMV), R471(ACDEGKMQSTV), D472(Y), Q473(ACFHMSY), S474(CI), R475(K), 475.5(SW), N476(STW), W477(Y), 477.5(L), L478(FI), P479(GIT), 479.5(D), G480(Y), P481(AV), 481.5(HY), C482(FGIQVY), 482.5(FM), Y483(ACFHILMQTV), 483.5(FQ), R484(K), 484.5(N), Q485(ACFGHILNSTVY), 485.5(EKQY), Q486(FGIMNSTVWY), 486.5(FV), R487(-H), 487.5(FW), V488(ACEFGHILMNQTWY), 488.5(ACFGILMPQVWY), S489(-ACFGHIKLMPQTVY), 489.5(CDEPQY), K490(-ACDEFGHILMNPQRSTVWY), 490.5(ACFGHILMNPQSTVWY), T491(ADEILMPQSVW), 491.5(ACFGILMPQTVWY), S492(ACDEILMNQTV), 492.5(ADEGILMPQSV), A493(DEILPRV), 493.5(ADGIKLMPV), D494(R), 494.5(GILMPTV), N495(-AFGILMPQSTVY), 495.5(AFGILMNPSTVWY), N496(-ACFGHILMQSTVWY), 496.5(FLNT), N497(-EILTV), 497.5(ADEGILMQTV), S498(-ADEFGILMPQRVWY), 498.5(ADEFGLMPQY), E499(DI), 499.5(ADEGHILMNPQRSTVWY), Y500(-ACDEFGIKLMNPQSTV), 500.5(AEFGHILMNPQSTVWY), S501 (-ACEFGILMNPTVWY), 501.5(ACFGHILMNPQRSTVWY), W502 (-ACEFGILMPQSTVY), 502.5(AFGHILMNPQSTVWY), T503 (-ADEFGIPQSVY), 503.5(AFGILMNPQSTVW), G504 (-ACFHILMNPQSTVWY), 504.5(ACFGHILMNPQSVWY), A505 (-CDEFGHILMNPQSTVWY), 505.5(ACFGILMPQSTVWY), T506 (-ACFGILMNPQSV), 506.5(ACIPSTVW), K507(ACHILMNQRSTVWY), Y508(-DIMSTV), H509(CEFNQ), 509.5(K), L510(I), 510.5(K), N511(ACDEGLMQSWY), 512.5(S), R513(CHIV), D514(ACEGILMQSTV), S515(CITV), L516(ACIMSTV), V517(CIL), 517.5(C), N518(CHILMQRTVY), P521(CFLMNSTV), 521.5(MS), A522(CPSV), M523(LV), 523.5(A), A524(CGPST), 524.5(ACHSTW), S525(ACGHMNP), 525.5(ACFGHILMNPQSTVWY), H526 (-ACDEFGIKLMNPQRSTVWY), 526.5(ACDEFGHILMNPQSTVWY), K527(-FHR), 527.5(ACDEFGHILMPQSTVWY), 528.5(DEPT), 529.5(ADEGLMNPTV), E530(DP), 530.5(ACDEFGHIKLMNQRSTVWY), E531(C), 531.5(ADEFGILMNPQSTVY), K532(-HRW), 532.5(FHIPSTVWY), F533(ACGHILMNQSTVW), 533.5(FHLY), F534(ILMVWY), 534.5(F), P535(-AF), Q536(-CDEFGNPTVWY), 536.5(L), S537(-ACDFGHNQTY), G538(-), V539(AHILMNQST), L540(M), 540.5(KMN), I541(-ACDGHPQTY), 541.5(DEGHMQST), F542(KP), 542.5(Y), G543(APS), 543.5(ACDHILMPQSTVY), K544 (-ACFGHILMNPQRSTVY), 544.5(ADEV), Q545(-DEFHLPVY), 545.5(CDNPTW), G546(ACDEMNPS), 546.5(CDEGILMPQSTV), S547 (-CDEFGHILMNPQVY), 547.5(ACDFGHLNPQSTVWY), | |

TABLE 9-continued

| Amino acid alterations that reduce delivery to blood. | |
|---|---|
| Amino acid alteration | Fold increase of efficiency |
| 548.5(CDELMPW), K549(-ACDEFGHILMNPQSTVWY), 549.5(ADELQTV), T550(ACDEGLNQ), 550.5(ADEGPST), N551(CDEFLMQSY), 551.5(CDENV), V552(ACEILMNST), 552.5(V), I554(ACEFHLMPQSTVW), 555.5(N), K556(ACDEGLMNQSTVWY), 556.5(Q), V557(ILM), M558(ACDHINQSTVWY), 558.5(E), I559(CFMQV), 559.5(A), T560(ACSV), 560.5(A), D561(AEFGHILMNQSTVY), E562(AD), E563(DG), I565(T), 565.5(Y), R566(ACDEFGHILMNQSTVWY), T567(AGPQS), 567.5(E), T568(PV), 569.5(M), P570(CQS), 570.5(M), V571(ACHLMQST), 571.5(G), A572(CGSY), 572.5(V), T573(ACDGINSVW), 573.5(MT), E574(CDFLMQW), 574.5(DV), Q575(-DFGIKLMNTVWY), 575.5(AFWY), Y576(ACFGHIS), 576.5(EFWY), 577.5(ACHIMNQSTV), S578(ADEFGHILNVWY), 578.5(ACEFGHILNST), V579(ACDEFGHILMNQST), 579.5(FGILMY), S580(-GMNPQT), T581(CEGKNP), N582(FILMSTVWY), 583.5(Q), Q584(AV), 584.5(FLNQT), R585(K), 585.5(AFGILMPQSTVY), G586(LMQ), 586.5(AGMPQST), N587(GILMQTV), 587.5(AFILMNQV), 588.5(ILMV), Q589(APSTV), 589.5(AFPV), A590(GILMNPQV), 590.5(ACGPQST), A591(CDHILMT), 591.5(AFGILMNPSTV), T592(-ACDEGMNPS), 592.5(ACFGILMNPSTVY), A593(-DEFNPY), 593.5(AFGMNPQSTVW), D594(E), 594.5(AFGHINQSTVWY), V595(ACDEFGHILMNPQSTWY), 595.5(ADEFHILMNQSTVW), N596(ACDEFGMPQTW), 596.5(DEN), T597(CDEGHIKLMNPQRVY), Q598(ACEFGHILMNSTVY), G599(CSW), V600(C), L601(FIMVWY), P602(M), M604(ACQS), V605(F), 605.5(N), 607.5(P), 610.5(F), Y612(F), Q614(N), P616(Q), A619(C), K620(ACMN), I621(AKL), H623(P), T624(V), D625(S), G626(A), F628(HIM), P630(CGHIQTV), 630.5(CHV), L633(FHMY), M634(C), 640.5(N), H641(M), Q645(LM), 655.5(IW), N656(FQ), 657.5(CH), S658(CEHMQ), 658.5(CEFGMQ), T659(CDHMS), 659.5(DEHPQY), T660(CDM), 660.5(DEF), F661(ELQTW), 661.5(LPS), S662(CDGP), 662.5(CDEFHMPW), A663(DEFNY), 663.5(CDEMW), A664(DEG), 664.5(ADEGNS), K665(P), 665.5(NP), F666(H), 666.5(V), A667(C), 667.5(Q), F669(Y), S674(E), E681(M), E697(M), 697.5(GNPW), I698(V), 699.5(E), Y700(F), 701.5(A), S702(N), N703(D), 703.5(E), N705(DEM), 705.5(E), K706(DEGST), S707(D), 707.5(Y), V708(CE), N709(CDE), V710(E), 711.5(QY), T716(CEM), N717(DE), V719(C), 720.5(N), S721(CIMQTV), E722(D), P723(ACEHIQTV), R724(FHNSTWY), P725(L), L735(IV), 735.5(LMV) | |

The preceeding describes a wide range of individual amino acid mutations that are tolerated and affect viral tropism, positively or negatively. It is specifically comtemplated herein that combinations of these various mutations can be made to further alter viral tropism, or other properties. In one embodiment, for example, at least 2 of the single amino acid mutations described herein are introduced in combination. For example, 2 mutations that influence tropism for liver can be combined. It is anticipated that the resulting virus will also have increased tropism for liver. In further embodiments, at least 3, 4, 5, 6, 7, 8, 9, 10, 11, 12, 13, 14, 15, or more mutations described herein are introduced in combination. We have demonstrated herein that a wide range of mutations are tolerated, however, no more than 40% of the amino acids should change relative to a reference sequence (e.g., SEQ ID NO: 1). In certain embodiments, no more than 35%, 30%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1% of amino acids, or fewer, are changed relative to a reference sequence (e.g., SEQ ID NO: 1).

Mutations that are at equivalent positions in other homologous viruses can be made and used for improving virus packaging and virus infectivity. Examples of other homologous viruses include any of AAV serotypes 1, and 3-12, as well as other natural isolates or synthetic sequences. Corresponding positions in homologous viruses can be inferred from sequence homology to AAV2. In one embodiment, the mutations described herein are introduced into the corresponding amino acid sequence of an AAV1, AAV3, AAV3B, AAV4, AAV5, AAV6, AAV7, AAV8, AAV9, AAV10, AAV11, AAV12, and AAV13 capsid polypeptide.

Site-directed mutagenesis is known in the art and can be used to introduce a point mutation(s) (e.g., amino acid substitutions, insertions, or deletations) or other mutations or combinations thereof to a viral capsid polypeptide. Site-directed mutatgenesis is further described in, e.g., Li B, et al. *Hum Gene Ther Methods.* 2015 December: 26(6):211-20, and Bachman, J. *Methods Enzymol.* 2013; 529:241-248, which are incorporated herein by reference in their entirety.

Combinations of mutations can be used to achieve a particular vector targeting goal. For example, it may be desirable to use a virus that has improved nucleic acid delivery in a first tissue and reduced nucleic acid delivery in one or more second tissues. Such a virus, whether achieved through a single mutation or multiple mutations, can have increased tissue specificity.

Mutatable Subregions of AAV2 Capsid Protein

It was found herein that particular regions of AAV2 capsid protein tolerate amino acid alterations, e.g., deletion, insertion, or substitution better than others, and that changes to certain regions that tolerate such change have pronounced impact on viral vector tropism. The region of the AAV2 capsid polypeptide of SEQ ID NO: 1 from amino acids 440 to 600 is identified herein as both tolerant of a variety of changes and highly influential for viral tropism, with certain mutations influencing tropism towards or away from certain tissues or cell types, as indicated in the Tables herein. Within this region, sub-regions including amino acids 440-460, 475-505, 518-532 and 560-590 are seen, for example, in the heat maps provided herein, to be particularly important for changes in viral tropism, and one of these sub-regions, from amino acids 561-588 is shown herein to tolerate extensive mutation. This region, which was found in single amino acid mutation studies to be important for tropism, was selected for initial studies of the effect of combinations of mutations. It was found that combinations of two to at least 8 different single amino acid mutations within this region were well tolerated, and further influenced tropism, as shown in the SEQ ID Nos: 3-20.

SEQ ID NO: 2 is an amino acid sequence encoding the amino acid region between amino acids 440-600 of SEQ ID NO: 1.

(SEQ ID NO: 2)

```
QYLYYLSRTNTPSGTTTQSRLQFSQAGASDIRDQSRNWLPGPCYRQQRV

SKTSADNNNSEYSWTGATKYHLNGRDSLVNPGPAMASHKDDEEKFFPQS

GVLIFGKQGSEKTNVDIEKVMITDEEEIRTTNPVATEQYGSVSTNLQRG

NRQAATADVNTQGV
```

TABLE 10

Amino acid alterations between amino acids 440-600 of SEQ ID NO: 1 conferring more efficient delivery to blood.

| Amino acid alteration | Fold increase of efficiency |
|---|---|
| 445.5(D), S446(-), 446.5(DE), R447(-PWY), 447.5(DEHQ), T448(-DEH), 448.5(D), N449(H), T450(FS), 452.5(P), G453(V), T454(APQ), T455(GMS), T456(A), 456.5(A), 457.5(MT), Q464(R), 464.5(Y), S468(M), C482(MSW), Y483(W), R484(ILQV), 485.5(M), Q486(DE), R487(ACDEFGILMNPQSTVWY), 488.5(DE), S489(DE), 490.5(DE), T491(FN), 491.5(DE), A493(FS), 493.5(ENST), 494.5(E), N495(DEW), 495.5(DE), N496(DE), 496.5(DE), N497(AMP), 498.5(ST), 500.5(D), S501(D), 501.5(DE), 502.5(DE), 503.5(DE), G504(DE), 504.5(E), 505.5(E), K507(-EF), P521(I), M523(C), S525(T), 525.5(DE), K527(PQW), D528(Q), E531(DGMN), K532(ADEFGILMNPQSTVY), 532.5(DEMN), F533(DEY), 533.5(CDEGSV), 536.5(V), V539(C), V571(DE), Q575(A), Y576(M), 577.5(E), V579(VV), 579.5(CDEN), S580(ADE), 580.5(DEILMPY), T581(DSWY), 581.5(DEFILMPQV), N582(-ACDEPQ), 582.5(GP), L583 (-DEGPT), 583.5(DEIPV), Q584(-DEFLNTY), 584.5(ADEIMVY), R585 (-ADEFGHILMNPQSTVWY), 585.5(DE), G586(-DEP), 586.5(DEFHINVY), N587(-DE), 587.5(DEGPY), R588(-ACDEFGHILMNPQSTVWY), 588.5(DEFQTY), Q589(DEFMNY), 589.5(DEGINS), A590(DEW), 590.5(DEFY), A591(EFPQSY), 591.5(CDEQWY), T592(FY), 592.5(DEQ), A593(GLMTVW), 593.5(CDEILY), 594.5(CDEP), 595.5(C), N596(S), T597(AS), V600(AILST) | 1.1-fold |
| 445.5(D), S446(-), 446.5(DE), R447(-P), 447.5(DEHQ), T448(-DE), N449(H), T454(P), 464.5(Y), C482(M), R484(ILQV), 485.5(M), Q486(DE), R487(ACDEFGILMNPQSTVWY), 488.5(E), S489(DE), 490.5(DE), T491(N), N495(DEW), 495.5(DE), N496(DE), 496.5(DE), S501(D), 501.5(D), 502.5(DE), 503.5(DE), G504(DE), K507(-E), 525.5(D), E531(GMN), K532(ADEFGILMNPSTVY), 532.5(DEM), F533(DE), 533.5(CDEGSV), V571(DE), 577.5(E), V579(V), 579.5(CDE), S580(DE), 580.5(DEILMY), T581(W), 581.5(DEFILMPQV), N582(-ACDEP), 582.5(GP), L583(-DEPT), 583.5(DEIPV), Q584(-DEFLTY), 584.5(DEIV), R585(-ADEFGHILMNPQSTVWY), 585.5(DE), G586(-DE), 586.5(DEFHY), N587(-DE), 587.5(DEP), R588 (-ACDEFGHILMNPQSTVWY), 588.5(DEFY), Q589(DEFY), 589.5(DEIN), A590(DEW), 590.5(DE), A591(PY), 591.5(CDEY), T592(FY), 592.5(DE), 593.5(CDE), 594.5(CDE), 595.5(C), N596(S) | 1.5-fold |
| 445.5(D), S446(-), 446.5(DE), R447(-P), 447.5(EHQ), T448(D), T454(P), 464.5(Y), R484(ILQV), 485.5(M), Q486(DE), R487(ACDEFGILMNPQSTVWY), 488.5(E), S489(DE), 490.5(D), N495(DEW), 495.5(DE), N496(DE), 496.5(DE), S501(D), 501.5(D), 502.5(E), 503.5(DE), G504(DE), K507(-), K532(ADEGILMNPSTV), 532.5(DE), F533(DE), 533.5(CDEGSV), V571(DE), 577.5(E), 579.5(DE), S580(DE), 580.5(DEILMY), T581(W), 581.5(DEFILMPQV), N582(-DEP), 582.5(GP), L583(-DEP), 583.5(DEIPV), Q584(-DEFY), 584.5(DEIV), R585(-ADEFGHILMNPQSTVWY), 585.5(DE), G586(-DE), 586.5(DEY), N587(-DE), 587.5(DEP), R588(-ACDEFGHILMNPQSTVWY), 588.5(DE), Q589(DE), 589.5(DEIN), A590(DEW), 590.5(DE), A591(PY), 591.5(DE), T592(FY), 592.5(DE), 593.5(DE), and 594.5(CDE) | 2-fold |
| N496(DE), S501(D), G504(D), K532(DE), 581.5(DEIPV), N582(DE), 582.5(G), L583(-DE), 583.5(DEP), Q584(-DE), 584.5(DE), R585 (-ADEFGHILMNPQSTVWY), 585.5(DE), G586(-D), 586.5(DE), N587(-DE), 587.5(DEP), R588(-ACDEFGHILMNPQSTVY), 588.5(DE), 589.5(DE), A590(DE), 590.5(D), 593.5(E), and 594.5(E) | 5-fold |
| R585(D) | 10-fold |

TABLE 11

Amino acid alterations between amino acids 440-600 of SEQ ID NO: 1 conferring more efficient delivery to heart.

| Amino acid alteration | Fold increase of efficiency |
|---|---|
| Y444(F), 448.5(S), N449(A), T450(M), S452(M), T454(LQ), 455.5(A), T456(AV), Q457(DLV), S458(AP), 458.5(Q), R459(FH), Q464(AI), A467(CGNPQ), S468(ADG), D469(AENQST), I470(LMV), R471(CKM), C482(M), Q486(N), R487(ACGIMQSTV), S489(AD), 490.5(N), T491(FLW), 492.5(M), A493(M), N496(DHSY), N497(PV), S498(FM), Y500(M), T506(S), V517(I), S525(AG), H526(CNST), E531(D), K532(ADEFGILMNQRST), I541(C), K544(CGTVY), Q545(E), K549(Q), N551(Y), V552(Q), K556(DNY), D561(Q), R566(ASV), T567(S), S578(TV), V579(V), S580(A), T581(WY), 581.5(IV), N582(DE), L583(DE), 584.5(EIV), R585(-ADFGHILMNQSTVWY), G586(DE), N587(DE), 587.5(D), R588(ACDEFHILMNQSTVY), 588.5(DE), Q589(M), A590(P), A591(ETY), 591.5(CDE), T592(F), 594.5(D), T597(ANSW), Q598(L), V600(AS) | 1.1-fold |
| D469(AQS), I470(LM), R471(K), R487(A), S489(D), 490.5(N), T491(W), N496(D), S498(M), K532(ADEL), D561(Q), N582(DE), L583(E), 584.5(V), R585(-AGHIMNQSTVWY), N587(DE), R588(ADEFILMNQSTVY), 588.5(DE), Q589(M), 591.5(D), T597(W), and V600(A) | 1.5-fold |
| R471(K), K532(D), N582(D), L583(E), R585(Q), N587(DE), R588(MQTV), and 588.5(E) | 2-fold |

TABLE 12

Amino acid alterations between amino acids 440-600 of SEQ ID NO: 1 conferring more efficient delivery to kidney.

| Amino acid alteration | Fold increase of efficiency |
|---|---|
| 446.5(D), 447.5(HQ), N449(ACGS), T456(AG), 456.5(G), R459(HK), Q464(A), A467(GNP), S468(AG), D469(AEQST), I470(LMV), R471(K), C482(M), Q486(D), R487(P), S489(E), 490.5(N), T491(F), A493(FI), N495(E), 495.5(DE), N496(EHS), 496.5(D), N497(P), S498(M), Y500(M), S501(D), 501.5(D), G504(D), N518(S), H526(CS), K532(DER), 532.5(D), F533(Y), K544(ILTV), T550(G), K556(N), D561(Q), R566(AV), S578(TV), V579(V), S580(A), 580.5(IMY), 581.5(EFILMPQV), N582(-ACDEP), 582.5(GP), L583(-DEIP), 583.5(DEIPV), Q584(-EFY), 584.5(DEILV), R585(-DEINPQVW), 585.5(D), G586(-), 586.5(DEIY), N587(-D), 587.5(DEP), R588(-ACDEGHLNPQTV), 588.5(DE), Q589(MP), 589.5(DE), A590(DEPV), 590.5(DE), A591(PST), 591.5(C), A593(M), 593.5(CE), T597(ASW), Q598(L), V600(A) | 1.1-fold |
| D469(AQ), I470(L), R471(K), 490.5(N), 495.5(DE), N496(EHS), S498(M), S501(D), K532(D), 580.5(I), 581.5(EILMPV), N582(-D), 582.5(GP), L583(DE), 583.5(DEIPV), Q584(-EFY), 584.5(IL), R585(-IP), G586(-), N587(-), 587.5(P), R588(-CDGV), 588.5(D), 589.5(DE), A591(P), 591.5(C), 593.5(C), T597(W), and V600(A) | 1.5-fold |
| R471(K), K532(D), 581.5(IM), L583(DE), 583.5(D), 584.5(L), G586(-), N587(-), 587.5(P), R588(-), 591.5(C), and 593.5(C) | 2-fold |

TABLE 13

Amino acid alterations between amino acids 440-600 of SEQ ID NO: 1 conferring more efficient delivery to liver.

| Amino acid alteration | Fold increase of efficiency |
|---|---|
| Y444(F), N449(S), T450(IV), S452(A), 455.5(A), T456(V), Q457(T), S458(AP), R459(HKT), L460(CN), A467(CGPQ), S468(G), D469(AENQST), I470(LMV), R471(CKM), C482(IM), Y483(M), Q486(N), 490.5(N), T491(DE), A493(MP), N496(HS), S498(AFLM), Y500(M), T503(V), T506(ACV), K507(S), V517(I), S525(G), H526(ACNST), K532(HINQWY), F533(Y), K544(C), 545.5(D), T550(E), I554(L), K556(ENY), M558(F), D561(Q), E563(D), R566(ACGNSTV), T567(S), S578(DEIT), V579(V), S580(A), T581(DM), L583(I), A590(IP), A591(DEQS), T592(S), A593(DET), N596(C), T597(ACDHLNQW), | 1.1-fold |

TABLE 13-continued

Amino acid alterations between amino acids 440-600 of SEQ ID NO: 1 conferring more efficient delivery to liver.

| Amino acid alteration | Fold increase of efficiency |
|---|---|
| Q598(ILMV), V600(AST) | |
| R459(H), L460(N), A467(CGPQ), D469(AEQST), I470(LM), R471(K), C482(I), Q486(N), N496(H), S498(M), H526(CNS), K532(N), K544(C), T550(E), K556(Y), R566(AGTV), A590(P), A591(E), A593(DE), T597(HNQ) | 1.5-fold |
| A467(G), D469(AEQS), I470(L), R471(K), Q486(N), N496(H), S498(M), H526(S), T550(E), A593(DE), and T597(N) | 2-fold |

TABLE 14

Amino acid alterations between amino acids 440-600 of SEQ ID NO: 1 conferring more efficient delivery to lung.

| Amino acid alteration | Fold increase of efficiency |
|---|---|
| Y444(F), N449(Q), T450(I), S452(M), T454(IQ), T455(G), S458(AP), 458.5(Q), R459(F), Q461(G), A467(CGNPQ), S468(G), D469(AENQST), I470(LMV), R471(K), 490.5(N), T491(QW), N497(P), N518(M), P521(V), F533(Y), V539(C), K544(C), Q545(N), T550(A), K556(N), D561(Q), S578(T), S580(A), Q589(M), A590(P), A593(T), T597(AS), V600(A), | 1.1-fold |
| S264(G), A467(G), D469(AQT), I470(M), R471(K), 490.5(N), and V600(A) | 1.5-fold |

TABLE 15

Amino acid alterations between amino acids 440-600 of SEQ ID NO: 1 conferring more efficient delivery to spleen.

| Amino acid alteration | Fold increase of efficiency |
|---|---|
| L445(I), S458(A), R459(K), S468(G), D469(Q), T491 (LQ), Y500(W), F533(Y), I541(C), M558(F), V579(V), S580(A), Q589(MN), A590(P), A591(S), A593(MT), T597(AMY), V600(AIT) | 1.1-fold |
| Q589(M), and V600(A) | 1.5-fold |

Figure 3:
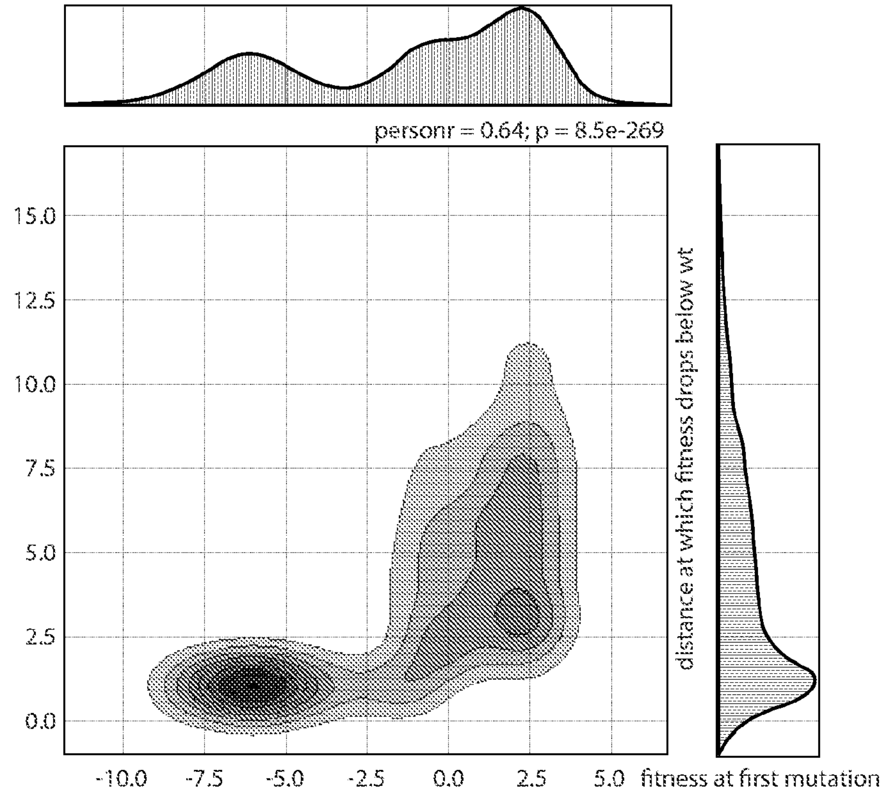
FIG. 3 shows a chart plotting the fitness at first mutation versus the distance at which fitness drops below wild-type (e.g., when the virus is no longer viable). On the x-axis, 0.0 indicates to a neutral mutation (e.g., a mutation that does not alter fitness of the virus), a positive value indicates to a beneficial mutation (e.g., a mutation that increases the fitness of the virus), and a negative value indicates a deleterious mutation (e.g., a mutation that decreases the fitness of the virus). Values on the y-axis indicate the number of mutations relative to wild-type.
Figure 4:
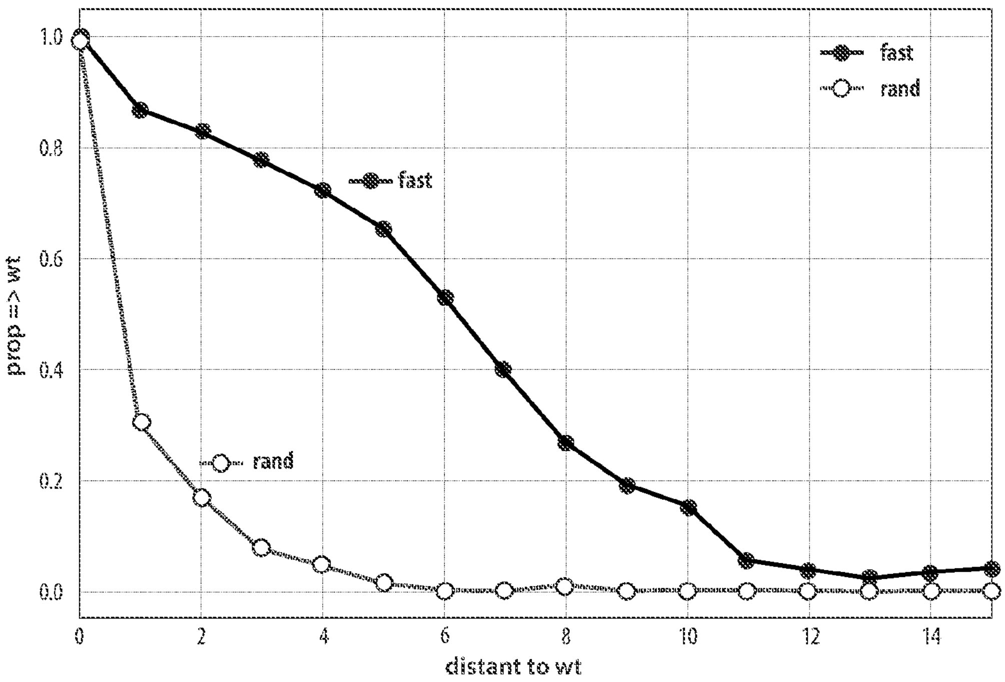
FIG. 4 is a line graph of path proportions showing at what mutation rate the mutation library fails. Random mutations result in a sharp decline at 1 mutation relative to wild-type, whereas fast (e.g., deep search mutations) mutations can tolerate up to 6 mutations. Deep search mutations are more than 40× more efficient that random search at distances greater than or equal to 6 mutations relative to wild-type.
Figure 5:
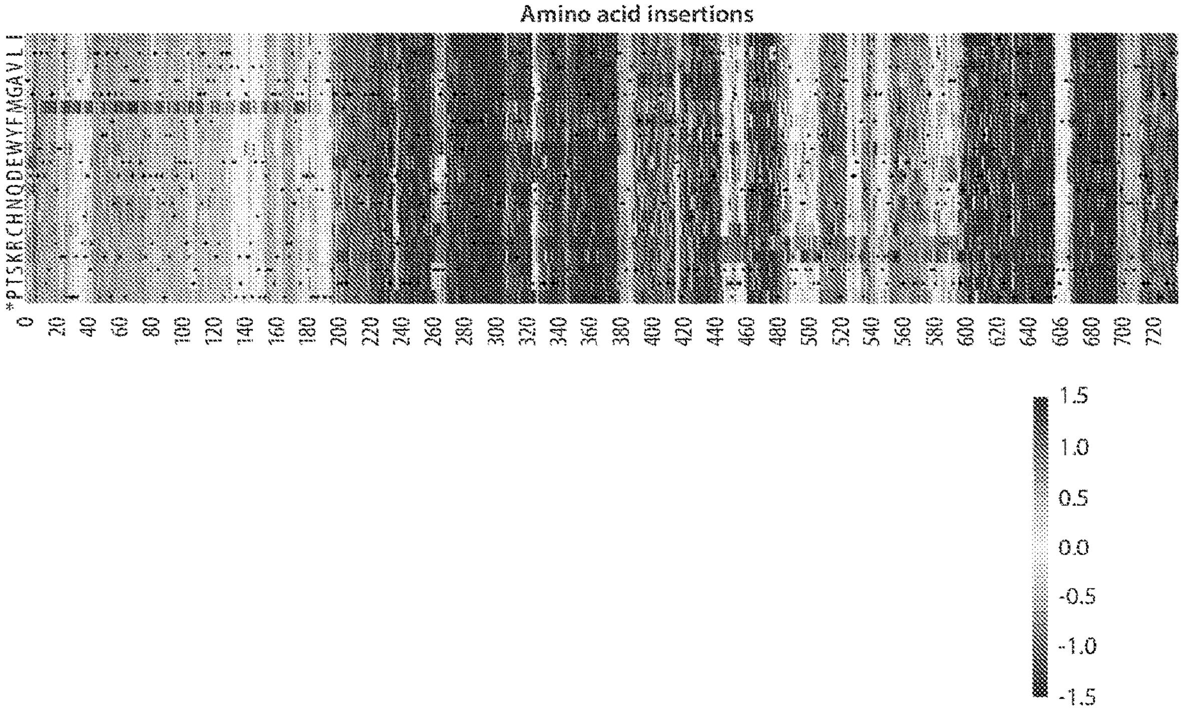
FIG. 5 shows a heat map of amino acid insertions introduced into the AAV2 viral capsid polypeptide that are beneficial, neutral, or deleterious to viral packaging.
Figure 6:
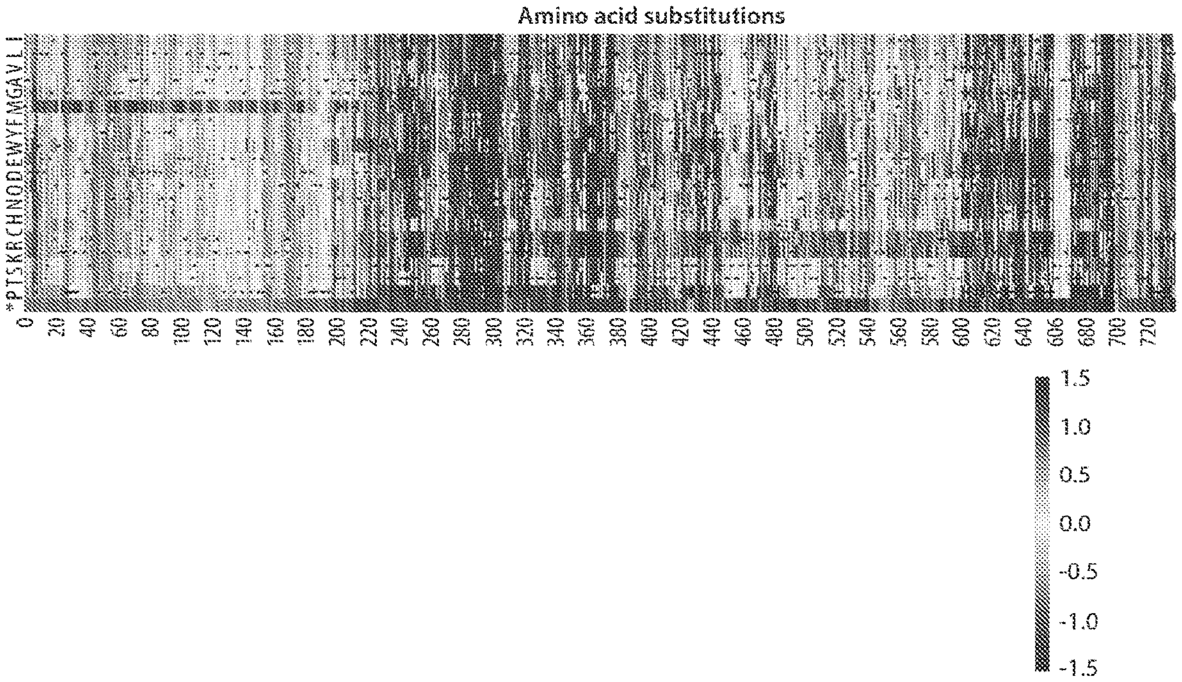
FIG. 6 shows a heat map of amino acid substitutions introduced into the AAV2 viral capsid polypeptide that are beneficial, neutral, or deleterious to viral packaging.

Interestingly, when combinations of mutations were examined, it was found that if a single mutation identified to be beneficial, e.g., for a change in tropism, is introduced, the resulting polypeptide tends to tolerate further mutation to include other single amino acid changes found to be beneficial. This is illustrated in, e.g., FIG. 3, which shows fitness at first mutation versus the number of mutations away from wild-type that will be tolerated before the virus is no longer viable. On the x-axis is the fitness at first mutation, i.e., whether a single mutation is neutral, deleterious, or beneficial. On the y-axis, is the number of mutations tolerated before the virus is no longer viable. The figure shows that if a virus has a first mutation that is beneficial, it will tolerate significantly more mutations, as compared to a virus with a first mutation that is neutral or deleterious. Thus, it is anticipated that combinations of mutations that do not interfere with viral fitness will be well tolerated.

Further identified herein are sub-regions (e.g., regions within the full length polypeptide) within the viral capsid polypeptide that are more likely to tolerate an amino acid change. One aspect herein is an AAV2 capsid polypeptide comprising a mutation in the sub-region of amino acids selected the group consisting of: 440-460 of SEQ ID NO: 1, 475-505 of SEQ ID NO: 1, 518-532 of SEQ ID NO: 1, and 560-590 of SEQ ID NO: 1 that alters tissue tropism of a virus comprising the viral capsid polypeptide. In further embodiments, at least 3, 4, 5, 6, 7, 8, 9, 10, 11, 12, 13, 14, 15, or more mutations described herein are introduced in combination into a sub-region. Though a wide range of mutations are tolerated, no more than 40% of the amino acids within a sub-region should change relative to a reference sequence (e.g., SEQ ID NO: 1). In certain embodiments, no more than 35%, 30%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1% of amino acids within a sub-region, or fewer, are changed relative to a reference sequence (e.g., SEQ ID NO: 1).

In one embodiment, a mutation described herein more efficiently increases viral tropism when introduced into a particular sub-region of the viral capsid polypeptide. In one embodiment, delivery is at least 1.1-fold more efficient as compared to a wild-type viral capsid polypeptide. In another embodiment, the delivery of a nucleic acid is at least 1.5-fold, at least 2-fold, at least 4-fold, at least 5-fold, at least 10-fold, or more, more efficient as compared to a virus comprising the wildtype SEQ ID NO: 1 capsid polypeptide.

One aspect of the technology is a method of altering tropism of a virus comprising modifying a capsid polypeptide corresponding to the polypeptide of SEQ ID NO: 1 to introduce a mutation in at least 2 regions selected from the group consisting of: amino acids 440-460 of SEQ ID NO: 1, amino acids 475-505 of SEQ ID NO: 1, amino acids 518-532 of SEQ ID NO: 1, and amino acids 560-590 of SEQ ID NO: 1.

One aspect is an AAV2 capsid polypeptide comprising a mutation in the region of amino acids 561-588 of SEQ ID NO: 1 that increases tissue tropism of a virus to the kidney, wherein the mutated region of amino acid 561-588 of SEQ ID NO: 1 has a sequence selected from the group consisting of:

(SEQ ID NO: 4)
DEEEIRQTNPVATEGYGEVSTNLMHGNK;

(SEQ ID NO: 5)
DEEEIRTTNPVATEQYGIVnStTNLNEGNR;

(SEQ ID NO: 6)
DEEEIRTTNPVATECYGSVSTDLQSGNL;

(SEQ ID NO: 7)
DENEIRTTNPVATEIYGSVSTeNLQNnGdNR;

(SEQ ID NO: 8)
DEEEIRTTNPVATEQYGSVSeTNpLvQNGdDR;

(SEQ ID NO: 9)
DEEEIRTTNPVATEQYGDVSENLMHFQN.

An AAV2 capsid polypeptide comprising a mutation in the region of amino acids 561-588 of SEQ ID NO: 1 that increases tissue tropism of a virus to the liver, wherein the mutated region of amino acid 561-588 of SEQ ID NO: 1 has a sequence selected from the group consisting of:

(SEQ ID NO: 10)
DEEEIRTTNPVATEQYGVVSDNLQRGNR;

(SEQ ID NO: 11)
DECEIRTTNPVATEQYGSVGENLQRGNR;

(SEQ ID NO: 12)
DEEEIRTTNPVATEQYGVVSENLQRGNR;

(SEQ ID NO: 13)
DESEITTTNPVATEQYGWVSTNQQRGNR;

(SEQ ID NO: 14)
HELEIATTNPVATEQYGSASTNIQRGNR;

(SEQ ID NO: 15)
DEEEIATTNPVATEQYGGVSTNLQRGNR.

An AAV2 capsid polypeptide comprising a mutation in the region of amino acids 561-588 of SEQ ID NO: 1 that increases tissue tropism of a virus to the lung, wherein the mutated region of amino acid 561-588 of SEQ ID NO: 1 has a sequence selected from the group consisting of:

(SEQ ID NO: 16)
DEEEIVTTNPVATEQYGNVSTNLQRGNR;

(SEQ ID NO: 17)
DEDEISTTNPVATEQYGSCSTNLQRGNR;

(SEQ ID NO: 18)
QEEEIRTTNPVATEQYGSVSTNLQRGDR;

(SEQ ID NO: 19)
NEEEIRTTNPCATEVYGSVSTNLQRGNR;

(SEQ ID NO: 20)
DEQEIVTTNPVATEVYGTVSTNLQRGNR.

One aspect of the technology described herein is a nucleic acid encoding any of the viral capsid polypeptides described herein.

Another aspect of the technology described herein is a viral particle comprising any of the viral capsid polypeptides described herein.

Corresponding Mutations

Mutations at corresponding locations in, for example homolgous viral capsid polypeptides, would be expected to have similar effects on viral tropism. Corresponding locations can include, for example, a location relative to the full length capsid polypeptide (e.g., SEQ ID NO: 1), or for that matter, a location relative to a sub-domain or sub-region of the the full length capsid polypeptide (e.g., SEQ ID NO: 2). In one aspect, a viral capsid polypeptide is provided herein that bears a mutation that corresponds to a mutation of the polypeptide of SEQ ID NO: 1 as described herein or selected from the group consisting of the mutations in Tables 1-9 relative to SEQ ID NO: 1. In one embodiment, a homologous viral capsid polypeptide has at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more sequence identity to wild-type AAV2 capsid protein (e.g., SEQ ID NO: 1). In another embodiment, the viral capsid polypeptides of AAV serotypes 1, and 3-13 are homolgous to a AVV2 capsid polypeptide.

One aspect described herein is a viral capsid polypeptide comprising a region corresponding to the amino acid sequence of SEQ ID NO: 2, wherein the region corresponding to the amino acid sequence of SEQ ID NO: 2 comprises a mutation relative to SEQ ID NO: 2 that alters tissue tropism of a virus comprising the viral capsid polypeptide, wherein the mutation is selected from the mutations in any one of Tables 10-15. In one embodiment, a homologous viral capsid polypeptide has at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more sequence identity to SEQ ID NO: 2.

As noted elsewhere herein, the identification of amino acid sites or regions of amino acid sequence in the AAV2 capsid polypeptide of SEQ ID NO: 1 that tolerate change in general, i.e., that permit packaging and infection by viral particles, as well as regions that influence tropism and/or packaging, either positively or negatively, can be used to guide changes in the capsid polypeptides of other AAV serotypes to similarly influence function or provide for modified properties. Thus, through use of sequence alignment, a mutation or set of mutations that provides a desired change in tropism and/or packaging for the AAV2 capsid polypeptide of SEQ ID NO: 1 can be introduced to the corresponding location of the capsid polypeptide of another AAV serotype to similarly influence those properties in that serotype. As but one example, it was determined herein that the region from amino acids 440 to 600 of the AAV2 capsid polypeptide of SEQ ID NO: 1 is important in determining viral tropism, and indeed, that there are sub-regions within that region, e.g., amino acids 561-588, that robustly influence tropism. It is contemplated that the introduction of changes identified herein in this amino acid 440 to 600 region, or in the amino acid 561-588 sub-region of the AAV2 capsid polypeptide to the corresponding region or sub-region of another AAV serotype capsid polypeptide will influence tropism of that AAV serotype in a similar manner.

Viral Packaging

One embodiment of the technology described herein relates to a method of increasing viral packaging by modification of an AAV2 capsid polypeptide to comprise at least one mutation in the region of amino acids selected the group consisting of: 34-38 of SEQ ID NO: 1, 133-152 of SEQ ID NO: 1, 188-194 of SEQ ID NO: 1, and 654-662 of SEQ ID NO: 1.

One embodiment of the technology described herein relates to a method of increasing viral packaging efficiency by modification of an AAV2 capsid polypeptide comprising any non-positive amino acid insertion, substitution, or deletion in the region of amino acids selected from the group consisting of: 442-452 of SEQ ID NO: 1, 489-506 of SEQ ID NO: 1, 541-551 of SEQ ID NO: 1, and 577-596 of SEQ ID NO: 1. In another embodiment, packaging efficiency is increased by the mutation of a plurality of amino acids to any non-positive amino acid insertion, substitution, or deletion in the region of amino acids selected from the group consisting of: 442-452 of SEQ ID NO: 1, 489-506 of SEQ ID NO: 1, 541-551 of SEQ ID NO: 1, and 577-596 of SEQ ID NO: 1.

TABLE 16

Amino acid alterations conferring more efficient viral packaging.

| Amino acid alteration | Fold increase of efficiency |
|---|---|
| D13(N), T14(HQ), I19(AV), Q21(F), W22(Y), W23(EFHIKLNQTVY), K24(M), L25(CI), K26(H), 28.5(AV), P29(ADFGIVY), P31(HIKNQT), 32.5(Q), K33(AFILNPQRST), P34(A), 34.5(AY), A35(-E), 35.5(CKPQSTVW), E36(GV), 36.5(ADGLV), R37(G), 37.5(ADEGNPQRV), H38(ADEGKPQVY), 38.5(ADE), K39(A), R43(T), P48(Y), E63(DHIP), V65(NS), N66(D), E67(A), A70(KQ), L73(N), K77(E), A78(K), D80(EHNQ), R81(H), D84(ET), S85(QT), N88(FV), K92(ACFLT), A98(Q), E99(DKQTV), Q101(HN), E102(Y), R103(AT), K105(DHN), E106(DTW), 108.5(H), S109(A), F110(K), L114(F), G115(A), R116(AFGIKLQST), A117(FLQSTW), V118(CFGILSTWY), Q120(EN), K123(C), R124(ADEHKNQT), V125(CFGILT), L126(ACDFGHNSTVY), E127(ADFGHIMNPSTY), L129(AFGHNPSWY), 129.5(P), G130(DHQ), L131(ACFGHQRWY), V132(CHY), 132.5(DE), 133.5(EKNT), E134(AHIKLNPQSTV), 134.5(ADEGHIKLNPQRSTVY), P135 (-ACDEFGHKNQRSTVWY), 135.5(CEFKMY), V136(ACDEFGHIKNPQRSTWY), 136.5(ADEFGNPSTW), K137(ET), 137.5(AKT), T138(-DHY), 138.5(ADEGINPQSTWY), A139(-DEGNPVW), 139.5(ACDEFGHILNPQSTVWY), P140(-ADEFNQSTVW), 140.5(ACDEFGHILNPSTVWY), G141(-ACDEFLNPQSTVWY), 141.5(ADFGHILPQSTVY), K142(-AEFGHILNQRSTVY), 142.5(FT), K143(-), P145(CFHLQT), 145.5(ACFGHILNPSVWY), V146(FGINPQWY), 146.5(DEGINQTVY), E147(DI), 147.5(ACDEFGHILNPQSTVY), H148 (-ACDEFGLNPQSTVWY), 148.5(CDEGLNPQSTVY), 149.5(PS), P150(FINWY), 150.5(ACEFGHIKLPQRSTVWY), V151(IQY), 151.5(ACDEHILPQRVWY), E152(LSWY), 152.5(F), S157(TWY), T159(FILQVY), K161(CF), A162(CIKNQSTVW), Q164(ACDFHKLNPRVWY), P166(H), Q175(WY), 175.5(D), 177.5(CFW), A179(P), D180(W), 180.5(S), S181(DEQ), 181.5(CST), V182(CIW), Q186(IVWY), 188.5(DST), G189(DENY), 189.5(CDEFGHINSTY), Q190 (-CDENSTW), 190.5(ADEFGIKLNPQSTVW), P191 (-CDEFGHIKLMNQSTVWY), 191.5(ADEFGHILMNPQSTVY), P192 (-ADEFQRSTY), 192.5(AGKQST), A193(EFKP), 193.5(AEP), A194(ST), 194.5(EY), P195(-D), S196(A), T200(CY), T202(CW), T205(AH), A209(S), E216(D), 237.5(D), 262.5(D), Q263(G), S267(T), N270(CDS), Y275(W), S276(A), R310(K), T324(S), 324.5(R), T344(AEHS), S346(DEKN), L354(IV), H358(ACQS), Q359(DE), L362(F), F370(Y), M371(LTV), V372(I), G376(A), L380(V), N381(C), N382(D), Q385(W), V387(L), P399(A), N408(T), T410(N), T414(Y), V418(M), Y424(F), A425(C), L433(TV), I438(ACLNTV), L442(F), Y443(F), Y444(F), L445(CMV), 445.5(ACDIMNQSTV), S446(-ACEHMNQTV), 446.5(ACDEFILMNPQSTVW), R447(-ACDEFGHILMNPQSTVWY), 447.5(CDEFGHILMNPQVWY), T448(-DEFHILMNPQVWY), 448.5(ADEFLMPY), N449(ACDEFGILMPQSVW), T450(EIS), 450.5(E), S452(DFL), 452.5(P), G453(EL), T454(EIM), 454.5(DE), T455(ADE), T456(D), 456.5(DG), Q457(ADELSV), 457.5(DE), S458(DENPTW), 458.5(DEFMWY), R459(-ACDEFGHILMNPQSTV), L460(ACIMNPSTV), Q461(E), S463(N), Q464(AIV), A467(GMNPS), S468(AGHMQ), D469(AEST), I470(CLMV), R471(ACKMQST), D472(Y), Q473(FH), C482(M), Y483(CIMVW), R484(IKLQV), 484.5(N), Q485(ACFIV), Q486(DEGNSTV), R487(ACDEFGHILMNPQSTVWY), V488(ACFILMWY), 488.5(DEP), S489(ADEGHMPQW), K490 (-ACDEFGHILMNPQRSTVWY), 490.5(DFGIMNQTVWY), T491(ADEFGMQSWY), 491.5(ADEFILNPQTV), S492(DEHMT), 492.5(ADEGILMQV), A493(DEFILMV), 493.5(DEINSV), 494.5(DEM), N495(ADEFILMPQVWY), 495.5(DEFGWY), N496(ACDEFGHILMQSVWY), 496.5(DE), N497(-AEILMTV), 497.5(DEGIMQST), S498(-ADEFGLMQTWY), 498.5(ADFGLMQS), E499(D), 499.5(ADELMNPQSTV), Y500(-ADEGLMNPQSTVW), 500.5(ADEFGLMNPQST), S501(-CDEFGILMNPQTV), 501.5(ACDEGHILMNQSTVWY), W502(P), 502.5(ADEFGHILMNPQSTVWY), T503(AFIPVY), 503.5(ADEFILMNSTVW), G504(ACDEFILMNPVWY), 504.5(ACEFILMQSTVWY), A505(EGLSY), 505.5(CEFILMV), T506(ACILMNPV), 506.5(ACIV), K507(-CFHILMNQSTVWY), 510.5(K), N511(ACDM), R513(V), S515(TV), L516(ACIMSTV), V517(I), N518(QT), P521(ILT), A522(P), M523(CQ), A524(G), 524.5(T), S525(CG), H526 (-ACDEGILMNPQRSTVW), K527(FHR), E531(DM), K532 | 1.1-fold |

TABLE 16-continued

Amino acid alterations conferring more efficient viral packaging.

| Amino acid alteration | Fold increase of efficiency |
|---|---|
| (-ADEFGHILMNPQRSTVWY), 532.5(AE), F533(ACDEGHILMNQSTV), 533.5(CDEGS), F534(MW), P535(-), Q536(-CDEFPTVY), 536.5(CV), S537(-ACDFGNQTY), G538(-), V539(CMST), I541(CH), K544(AILMQT), 544.5(D), Q545(EM), 545.5(E), G546(H), 546.5(D), K549(CNQT), 549.5(E), T550(AD), N551(DEMY), I554(QV), K556(DE), M558(N), D561(Q), R566(ACGMNSTVW), V571(ACES), A572(G), T573(CG), E574(D), Q575(GILMNTV), Y576(CM), 577.5(E), S578(DEGILNWY), 578.5(A), V579(ACEGIMNSTWY), 579.5(DEN), S580(-DEGINPQT), 580.5(DEL), T581(-DEMNPSWY), 581.5(DEILPQ), N582(-ACDEFILMPQSTVWY), 582.5(GP), L583(DEGIPTV), 583.5(DEPQV), Q584(DEGILTV), 584.5(ADEFGILMQSTVY), R585(-ADEFGHIKLMNPQSTVWY), 585.5(ADEFGILMNPQSTVY), G586(-DELMP), 586.5(ADEFGHILMNPQSTV), N587(-DEGILMPQTV), 587.5(ADEFILMNPQSTVY), R588(-ACDEFGHILMNPQSTVWY), 588.5(DEILMQTVY), Q589(ADEFMNPSTVY), 589.5(ADEFNPSTV), A590(DEGIMPSV), 590.5(ADEFGPST), A591(DEFILMPTVY), 591.5(ACDEFGILMNPQSTVY), T592(-ACDEFGLMNPQSY), 592.5(ACDEFGILMNQSTVWY), A593(-DEFL), 593.5(ACDEFGILMNPQSTVWY), D594(E), 594.5(ACDEFGHILMPQSTVWY), V595(ACEGHILMNPQTW), 595.5(CDEILMTV), N596(CDE), T597(CDEGHILNQSVW), Q598(ACEFHILMSTVY), V600(L), L601(FIMVY), V605(I), W606(F), Q607(M), D608(N), P616(Q), H627(C), P630(ACM), H641(ENT), I646(V), L647(M), N656(A), S658(FNQ), 658.5(NT), T659(NS), T660(H), 660.5(T), F661(Y), S662(M), 662.5(FGSW), A663(CGHIQT), 663.5(DEQ), A664(QT), 664.5(EH), K665(HR), F666(MW), A667(FS), S679(M), V708(W), T716(A), N734(C) | |
| W23(EN), P29(AFGIV), P31(NT), P34(A), 34.5(A), E36(V), 36.5(AG), R37(G), 37.5(ADEGV), H38(ADEGQV), 38.5(AE), R43(T), N66(D), A78(K), Q101(H), K105(N), A117(W), R124(DN), V125(T), L126(FHNY), E127(D), L129(HSY), L131(Y), 132.5(E), 133.5(EN), 134.5(ADEIKNT), P135(ADEFHKNQTW), V136(DEHKPST), 136.5(ADE), 137.5(KT), 138.5(AE), A139(E), 139.5(AEFLNPQSTY), P140(-), 140.5(CDFIPY), G141(-DE), K142(-EGILQSTVY), K143(-), V146(GW), 146.5(DN), H148 (-DEQW), 148.5(EY), 149.5(P), P150(FWY), 150.5(ACEFILQVY), 151.5(CPQY), T159(IY), A162(VW), Q164(Y), Q175(Y), 177.5(W), 180.5(S), 181.5(T), V182(W), Q186(VW), G189(DE), 189.5(C), Q190(D), 190.5(EQW), P191(DEFLSWY), 191.5(ILTY), P192(EFT), 192.5(T), T205(H), N270(CD), V372(I), G376(A), N382(D), Q385(W), T410(N), A425(C), I438(AV), Y444(F), L445(C), 445.5(DMNQST), S446(-CNQV), 446.5(ADEFILNPSTVW), R447(-ACDEFGILMNPQSTVWY), 447.5(DEFHILMNPQVWY), T448(-DEFHILMNPQVWY), 448.5(DEP), N449(ACDEFIMP), T450(E), S452(DF), T454(IM), 454.5(DE), T455(DE), 456.5(D), Q457(DE), 457.5(DE), S458(DE), 458.5(DEFW), R459(ACDEGLNPQSTV), L460(ACNSV), Q461(E), S463(N), Q464(AIV), A467(M), D469(E), I470(LM), R471(ACKMQST), D472(Y), Q473(H), C482(M), Y483(V), R484(IKLQ), Q485(C), Q486(DEN), R487(ACDEFGHILMNPQSTVWY), V488(CFMWY), 488.5(D), S489(ADEGMPQW), K490(ACDEFGHILNPQSTVWY), 490.5(DV), T491(DEMQW), 491.5(DEINPQT), S492(E), 492.5(DELQV), A493(EM), 493.5(DN), 494.5(DE), N495(ADEILPQVW), 495.5(DEFWY), N496(ACDEFGHILMVWY), 496.5(DE), N497(-ELV), 497.5(DEMQ), S498(ADEFGLMQWY), 498.5(DFGLMQS), 499.5(ADELMNPQSTV), Y500(-AELNPQSW), 500.5(EGLMNQST), S501(-CDEILMNPTV), 501.5(ACDEGHILMNSTVW), 502.5(ADEFILMSTVWY), T503(PV), 503.5(DEILMNTVW), G504(ACDEFIMVWY), 504.5(CEFILMSTVW), A505(E), 505.5(EIMV), T506(ACILMNV), 506.5(ACV), K507 (-CFHILMNQSTVWY), 510.5(K), N511(D), R513(V), L516(ACSTV), V517(I), H526(ACDEGILMNPQSTV), K527(FHR), K532 (-AFGILMNPQSTVWY), 532.5(E), F533(ACDEGILMNSTV), 533.5(D), Q536(-CPY), 536.5(CV), S537(-CDGNTY), G538(-), T550(D), N551(E), R566(ACGNSTVW), V571(ES), Q575(GIL), 577.5(E), S578(DEILWY), V579(ACGSY), 579.5(DE), S580(-DENPQ), 580.5(DE), T581(-DENP), 581.5(DEQ), N582(-ACDEFILMPQTVWY), 582.5(GP), L583(DEGIP), 583.5(DPQV), Q584(DEIV), 584.5(ADEFGILMQSTVY), R585 (-ADEFGHILMNPQSTVWY), 585.5(ADEFGILMNPQSTVY), G586(-M), 586.5(ADEFGILMNPQSTV), N587(-DEGILMPQTV), 587.5(ADEFILMNQSTVY), R588(-ACDEFGHILMNPQSTVWY), 588.5(DEILMTV), Q589(ADEPSTV), 589.5(ADEFNPTV), A590(DEGIPV), 590.5(ADEGPST), A591(DEFILMTVY), 591.5(ACDEFGILMNPQSTV), T592(-ACDEGNPSY), 592.5(ACDEFGILMNQSTVWY), A593(-DE), 593.5(ACDEFGILMNPQSTVWY), D594(E), 594.5(ADEFHILMPQTVWY), V595(ACEGHLMNPT), 595.5(CDEILV), N596(CDE), T597(DEGHINQVW), Q598(ACEFVY), V600(L), L601(IMY), 662.5(F), 663.5(Q), V708(W) | 1.5-fold |

TABLE 16-continued

| Amino acid alterations conferring more efficient viral packaging. | |
|---|---|
| Amino acid alteration | Fold increase of efficiency |
| P29(AV), 34.5(A), 37.5(AEGV), H38(AEGV), 38.5(A), Q101(H), R124(N), P135(DW), 138.5(E), A139(E), P140(-), K142(I), P150(Y), 150.5(Y), 181.5(T), V182(W), Q186(W), 191.5(Y), N270(D), 445.5(DQ), 446.5(DEN), R447(ACDEILMNPQSTVW), 447.5(DEFHILMNPQWY), T448 (-DEFHILPQW), 448.5(DE), N449(ADEF), T450(E), T454(M), 454.5(DE), T455(E), Q457(DE), S458(DE), 458.5(DEW), R459(ACDEPQTV), L460(NS), Q461(E), D469(E), R471(ACKMQST), Y483(V), R484(ILQ), Q485(C), Q486(DEN), R487(ACDEGHILMNPQSTVWY), V488(FMWY), S489(DEGW), K490(ACDEGHLNPQSTVWY), T491(Q), 491.5(DE), S492(E), 492.5(DEQ), A493(E), 493.5(D), 494.5(DE), N495(DEIP), 495.5(DEFWY), N496(DEFGHIMW), 496.5(DE), N497(EV), 497.5(DEMQ), S498(DEFGLMWY), 498.5(DFLMQ), 499.5(ADEMNPQS), Y500(-AELNPQS), 500.5(EGMNQST), S501(ILMNTV), 501.5(ACDEGHILNSTVW), 502.5(ADEFVWY), T503(PV), 503.5(DELTV), G504(DEFMW), 504.5(FIVW), A505(E), 505.5(EI), T506(ILMNV), 506.5(V), K507(-CFHILMNQSTVWY), 510.5(K), R513(V), L516(AST), H526(ACEGIMNQTV), K527(FH), K532(AFGILMPQSTVWY), F533(ACDEGISTV), Q536(-P), 536.5(V), S537(-DNY), G538(-), R566(ACW), V571(E), Q575(IL), 577.5(E), S578(DEIWY), V579(A), 579.5(DE), S580(DENQ), 580.5(DE), T581 (-DEN), 581.5(DEQ), N582(-DEFILMPTVWY), L583(D), 583.5(DQ), Q584(DEV), 584.5(ADEFILMQSTVY), R585(-ADFGHILMNPQSTVWY), 585.5(ADEFIMNPQSTVY), 586.5(ADEFGILMPQSTV), N587(DEGILMPQTV), 587.5(ADEFILMQTV), R588 (-ACDEFGHILMNPQSTVWY), 588.5(DEILMV), Q589(ADEPSTV), 589.5(ADEFNPTV), A590(DEGP), 590.5(ADEGPS), A591(DEFILMTVY), 591.5(ADEFGILMNPQSTV), T592(DEGY), 592.5(ACDEFGILMNSTVWY), A593(-DE), 593.5(ACDEFGILMNSTWY), 594.5(ADEFILMPQTVWY), V595(AGHLMN), 595.5(CDIV), N596(DE), T597(DEINQVW), Q598(CFVY), L601(Y) | 2-fold |
| 448.5(D), S458(E), R471(AMST), R484(ILQ), Q486(E), R487(CGILPQSTVY), V488(Y), K490(E), N495(E), 495.5(D), N496(DEF), 496.5(DE), 497.5(E), S498(D), 498.5(Q), S501(IL), 501.5(DE), K507(CFHILMSTVWY), Q536(-), S537(-), 577.5(E), S578(DE), 579.5(DE), S580(E), 580.5(E), T581(DE), N582(FIPW), Q584(DE), 584.5(D), R585(FIVWY), 585.5(ADNY), 586.5(EILMPV), N587(M), 587.5(DILV), R588(ADFHILMNPSTVWY), 588.5(DE), Q589(DP), 589.5(P), A590(DE), 590.5(DEGP), A591(DE), 591.5(DEFILMV), T592(DE), 592.5(DEFNSW), A593(DE), 593.5(DE), 594.5(DEFV), 595.5(CV), N596(D) | 5-fold |
| R471(AMS), R487(I), K507(CIVWY), S578(D), 580.5(E), T581(DE), N582(F), R588(FL), 590.5(D), 591.5(DE), T592(DE), 592.5(D), 593.5(D), 594.5(D) | 10-fold |

In one embodiment, a mutation in the viral capsid polypeptide that alters viral tropism as described herein, is combined with a mutation or mutations that increase viral packaging (e.g., any mutation of Table 16).

In another embodiment, a mutation in the viral capsid polypeptide that alters viral tropism as described herein, is combined with a mutation in the region of amino acids selected the group consisting of: 34-38 of SEQ ID NO: 1, 133-152 of SEQ ID NO: 1, 188-194 of SEQ ID NO: 1, and 654-662 of SEQ ID NO: 1 that increases viral packaging.

In yet another embodiment, a mutation in the viral capsid polypeptide that alters viral tropism, as described herein, is combined with any non-positive amino acid insertion, substitution, or deletion in the region of amino acids selected the group consisting of: 442-452 of SEQ ID NO: 1, 489-506 of SEQ ID NO: 1, 541-551 of SEQ ID NO: 1, and 577-596 of SEQ ID NO: 1 that increases viral packaging.

Any region is the packaging heat map that tolerates change, e.g, neutral or positive regions, can potentially tolerate the insertion of additional functional peptide sequences, e.g., an epitope, a tag, a ligand, or other structural sequence that would not necessarily interrupt packaging of a virus.

Methods for Delivering Nucleic Acid

Provide herein is a method of delivering a nucleic acid to a cell comprising contacting a cell with a viral particle comprising any of the viral capsid polypeptides described herein. In one embodiment, the contacting occurs in vitro. In one embodiment, the contacting occurs ex vivo. In another embodiment, the contacting occurs in vivo, e.g., via local or systemic administration.

In one embodiment, the delivering of a nucleic acid is at least 1.1-fold more efficient as compared to a wild-type viral capsid polypeptide. In one embodiment, the the delivering of a nucleic acid is at least 1.5-fold, at least 2-fold, at least 4-fold, at least 5-fold, at least 10-fold, or more, more efficient as compared to a wild-type viral capsid polypeptide. Methods for measuring tropism are described herein above.

In one aspect, a nucleic acid is delivered to a blood cell by contacting a blood cell with a viral particle comprising a viral capsid polypeptide comprising a mutation of Table 1. The cell can be any type blood cell. Exemplary blood cells include, but are not limited to, red blood cells, platelets, neutrophils, eosinophils, basophils, lymphocytes, or monocytes.

In one aspect, a nucleic acid is delivered to a heart cell by contacting a heart cell with a viral particle comprising a viral capsid polypeptide comprising a mutation of Table 2. Exemplary heart cells include, but are not limited to, cardiomyocyte, endocardial cells, or cardiac smooth muscle cells.

In one aspect, a nucleic acid is delivered to a kidney cell by contacting a kidney cell with a viral particle comprising a viral capsid polypeptide comprising a mutation of Table 3. Exemplary kidney cells include, but are not limited to, kidney glomerulus parietal cells, kidney glomerulus podocytes, kidney proximal tubule brush border cells, loop of Henle thin segment cells, thick ascending limb cells, kidney distal tubule cells, collecting duct principal cells, collecting duct intercalated cells, and interstitial kidney cells.

In one aspect, a nucleic acid is delivered to a liver cell by contacting a liver cell with a viral particle comprising a viral capsid polypeptide comprising a mutation of Table 4. Exemplary liver cells include, but are not limited to, parenchymal cells, non-parenchymal cells, sinusoidal endothelial cells, phagocytic Kupffer cells, hepatic stellate cells, and intrahepatic lymphocytes.

In one aspect, a nucleic acid is delivered to a lung cell by contacting a lung cell with a viral particle comprising a viral capsid polypeptide comprising a mutation of Table 5. Exemplary lung cells include, but are not limited to, bronchioles, lung epithelial cells, lung smooth muscle cells, and alveoli.

In one aspect, a nucleic acid is delivered to a spleen cell by contacting a spleen cell with a viral particle comprising a viral capsid polypeptide comprising a mutation of Table 6. Exemplary spleen cells include, but are not limited to, splenic endothelial cells and splenic fibroblasts.

Method for Reducing Viral Tropism

One aspect of the technology described herein is a method for reducing tissue tropism of a virus comprising modifying a viral capsid polypeptide corresponding to the viral capsid polypeptide of SEQ ID NO: 1 by introducing a mutation set out in any of Tables 7-9. In one embodiment, the viral tropism for liver, spleen, or blood is reduced.

In one embodiment, the method for reducing viral tropism further comprises any mutation, or combination thereof, as described herein, that increases tropism for a tissue other than the tissue for which the tropism is reduced. For example, a viral capsid polypeptide bearing a mutation which reduces tropism for liver is combined a mutation that increases tropism for kidney. In this example, it is contemplated that this combination of mutations will result in increased tropism for kidney.

Further, one aspect provides a method of increasing delivery of a nucleic acid to a cell of a kidney, heart, or lung, comprising contacting a cell of a kidney, heart, or lung with a viral particle comprising a viral capsid polypeptide comprising a mutation that reduces delivery of a nucleic acid to a cell of a liver, blood, or spleen. In one embodiment, the mutation that reduces delivery of a nucleic acid to a cell of a liver, blood, or spleen is selected from any of Tables 7-9. In one embodiment, the contacting is performed in vivo, e.g., via local or systemic administration.

Another aspect provides a method of delivering a nucleic acid to a lung cell comprising contacting a lung cell with a viral particle comprising a viral capsid polypetide comprising a mutation of Table 5 and a mutation selected from any of Tables 7-9. In one embodiment, the contacting is performed in vivo, e.g., via local or systemic administration.

Another aspect provides a method of delivering a nucleic acid to a heart cell, the method comprising contacting a heart cell with a viral particle comprising a viral capsid polypetide comprising a mutation of Table 2 and a mutation selected from any of Tables 7-9. In one embodiment, the contacting is performed in vivo, e.g., via local or systemic administration.

Yet another aspect provides a method of delivering a nucleic acid to a kidney cell comprising contacting a kidney cell with a viral particle comprising a viral capsid polypetide comprising a mutation of Table 3 and a mutation selected from any of Tables 7-9. In one embodiment, the contacting is performed in vivo, e.g., via local or systemic administration.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Some embodiments of the technology described herein can be defined according to any of the following numbered paragraphs:

1. A viral capsid polypeptide bearing a mutation relative to SEQ ID NO: 1 (WT AAV2) that alters tissue tropism of a virus comprising the viral capsid polypeptide, wherein the mutation is selected from the mutations in any one of Tables 1-9.
2. The viral capsid polypeptide of paragraph 1, wherein the tissue is heart, kidney, liver, lung, spleen, or blood.
3. The viral capsid polypeptide of any of the proceeding paragraphs, wherein the tropism to the tissue is increased.
4. The viral capsid polypeptide of any of the proceeding paragraphs, wherein the tropism to the tissue is decreased.
5. A nucleic acid encoding the viral capsid polypeptide of any of the proceeding paragraphs.
6. A viral particle comprising a viral capsid polypeptide of any of the proceeding paragraphs.
7. A viral capsid polypeptide bearing a mutation that corresponds to a mutation of the polypeptide of SEQ ID NO: 1, the mutation selected for the group consisting of the mutations in Tables 1-9 relative to SEQ ID NO: 1.
8. A viral capsid polypeptide comprising a region corresponding to the amino acid sequence of SEQ ID NO: 2, wherein the region corresponding to the amino acid sequence of SEQ ID NO: 2 comprises a mutation relative to SEQ ID NO: 2 that alters tissue tropism of a virus comprising the viral capsid polypeptide, wherein the mutation is selected from the mutations in any one of Tables 10-15
9. The viral capsid polypeptide of any of the proceeding paragraphs, wherein the tissue is heart, kidney, liver, lung, spleen, or blood.
10. The viral capsid polypeptide of any of the proceeding paragraphs, wherein the tropism to the tissue is increased.
11. The viral capsid polypeptide of any of the proceeding paragraphs, wherein the tropism to the tissue is decreased.
12. A nucleic acid encoding the viral capsid polypeptide of any of the proceeding paragraphs.
13. A viral particle comprising a viral capsid polypeptide of any of the proceeding paragraphs.
14. A method of delivering a nucleic acid to a cell, the method comprising; contacting the cell with a viral particle comprising a viral capsid polypeptide of any of the proceeding paragraphs.
15. A method of delivering a nucleic acid to a blood cell, the method comprising; contacting a blood cell with a viral particle comprising a viral capsid polypeptide comprising a mutation of Table 1.
16. A method of delivering a nucleic acid to a heart cell, the method comprising; contacting a heart cell with a viral particle comprising a viral capsid polypeptide comprising a mutation of Table 2.

17. A method of delivering a nucleic acid to a kidney cell, the method comprising;

contacting a kidney cell with a viral particle comprising a viral capsid polypeptide comprising a mutation of Table 3.

18. A method of delivering a nucleic acid to a liver cell, the method comprising; contacting a liver cell with a viral particle comprising a viral capsid polypeptide comprising a mutation of Table 4.

19. A method of delivering a nucleic acid to a lung cell, the method comprising; contacting a lung cell with a viral particle comprising a viral capsid polypeptide comprising a mutation of Table 5.

20. A method of delivering a nucleic acid to a spleen cell, the method comprising; contacting a spleen cell with a viral particle comprising a viral capsid polypeptide comprising a mutation of Table 6.

21. The method of any of the proceeding paragraphs, wherein the delivering is at least 1.1-fold more efficient as compared to a wild-type viral capsid polypeptide.

22. A method of reducing tissue tropism of a virus comprising a viral capsid polypeptide corresponding to the viral capsid polypeptide of SEQ ID NO: 1, the method comprising introducing a mutation set out in any of Tables 7-9.

23. A method of increasing delivery of a nucleic acid to a cell of a kidney, heart, or lung, the method comprising; contacting a cell of a kidney, heart, or lung with a viral particle comprising a viral capsid polypeptide comprising a mutation that reduces delivery of a nucleic acid to a cell of a liver, blood, or spleen.

24. The method of paragraph 23, wherein the mutation that reduces delivery of a nucleic acid to a cell of a liver, blood, or spleen is selected from any of Tables 7-9.

25. A method of delivering a nucleic acid to a lung cell, the method comprising; contacting a lung cell with a viral particle comprising a viral capsid polypetide comprising a mutation of Table 5 and a mutation selected from any of Tables 7-9.

26. A method of delivering a nucleic acid to a heart cell, the method comprising; contacting a heart cell with a viral particle comprising a viral capsid polypetide comprising a mutation of Table 2 and a mutation selected from any of Tables 7-9.

27. A method of delivering a nucleic acid to a kidney cell, the method comprising;

contacting a kidney cell with a viral particle comprising a viral capsid polypetide comprising a mutation of Table 3 and a mutation selected from any of Tables 7-9.

28. An AAV2 capsid polypeptide comprising a mutation in the region of amino acids selected the group consisting of: 440-460 of SEQ ID NO: 1, 475-505 of SEQ ID NO: 1, 518-532 of SEQ ID NO: 1, and 560-590 of SEQ ID NO: 1 that alters tissue tropism of a virus comprising the viral capsid polypeptide.

29. The AAV2 capsid polypeptide of paragraph 28, wherein the tissue is kidney, liver, or lung.

30. The AAV2 capsid polypeptide of paragraph 28, wherein the tropism is increased.

31. An AAV2 capsid polypeptide comprising a mutation in the region of amino acids 561-588 of SEQ ID NO: 1 that increases tissue tropism of a virus to the kidney, wherein the mutated region of amino acid 561-588 of SEQ ID NO: 1 has a sequence selected from the group consisting of: DEEEIATTNPVATEQYGDVSENLMHFQN (SEQ ID NO: 3);

(SEQ ID NO: 4)
DEEEIRQTNPVATEGYGEVSTNLMHGNK;

(SEQ ID NO: 5)
DEEEIRTTNPVATEQYGIVnStTNLNEGNR;

(SEQ ID NO: 6)
DEEEIRTTNPVATECYGSVSTDLQSGNL;

(SEQ ID NO: 7)
DENEIRTTNPVATEIYGSVSTeNLQNnGdNR;

(SEQ ID NO: 8)
DEEEIRTTNPVATEQYGSVSeTNpLvQNGdDR;

(SEQ ID NO: 9)
DEEEIRTTNPVATEQYGDVSENLMHFQN.

32. An AAV2 capsid polypeptide comprising a mutation in the region of amino acids 561-588 of SEQ ID NO: 1 that increases tissue tropism of a virus to the liver, wherein the mutated region of amino acid 561-588 of SEQ ID NO: 1 has a sequence selected from the group consisting of: DEEEIRTTNPVATEQYGVVSDNLQRGNR (SEQ ID NO: 10):

(SEQ ID NO: 10)
DEEEIRTTNPVATEQYGVVSDNLQRGNR;

(SEQ ID NO: 11)
DECEIRTTNPVATEQYGSVGENLQRGNR;

(SEQ ID NO: 12)
DEEEIRTTNPVATEQYGVVSENLQRGNR;

(SEQ ID NO: 13)
DESEITTTNPVATEQYGWVSTNQQRGNR;

(SEQ ID NO: 14)
HELEIATTNPVATEQYGSASTNIQRGNR;

(SEQ ID NO: 15)
DEEEIATTNPVATEQYGGVSTNLQRGNR.

33. An AAV2 capsid polypeptide comprising a mutation in the region of amino acids 561-588 of SEQ ID NO: 1 that increases tissue tropism of a virus to the lung, wherein the mutated region of amino acid 561-588 of SEQ ID NO: 1 has a sequence selected from the group consisting of: DEEEIVTTNPVATEQYGNVSTNLQRGNR (SEQ ID NO: 16):

(SEQ ID NO: 17)
DEDEISTTNPVATEQYGSCSTNLQRGNR;

(SEQ ID NO: 18)
QEEEIRTTNPVATEQYGSVSTNLQRGDR;

(SEQ ID NO: 19)
NEEEIRTTNPCATEVYGSVSTNLQRGNR;

(SEQ ID NO: 20)
DEQEIVTTNPVATEVYGTVSTNLQRGNR.

34. A method of altering tropism of a virus comprising a capsid polypeptide corresponding to the polypeptide of SEQ ID NO: 1, the method comprising introducing a mutation in at least 2 regions selected from the group consisting of: amino acids 440-460 of SEQ ID NO: 1, amino acids 475-505 of SEQ ID NO: 1, amino acids 518-532 of SEQ ID NO: 1, and amino acids 560-590 of SEQ ID NO: 1.

35. A viral capsid polypeptide bearing a mutation relative to SEQ ID NO: 1 (WT AAV2) that alters packaging efficiency of a virus comprising the viral capsid polypeptide, wherein the mutation is selected from the mutations in Table 16.

REFERENCES

1. Adachi, Kei, Enoki, Tatsuji, Kawano, Yasuhiro, Veraz, Michael, and Nakai Hiroyuki, *Drawing a high-resolution functional map of adeno-associated virus capsid by massively parallel sequencing*. Nature Communications 5, 3075 (2014)
2. Grimm, D. and Zolotukhin, S. *E Pluribus Unum: 50 Years of Research, Millions of Viruses, and One Goal-Tailored Acceleration of AAV Evolution.* Molecular Therapy 23, 1819-1831 (2015).

What is claimed is:

1. An AAV2 capsid polypeptide comprising:

a mutation in the region of amino acids 561-588 of SEQ ID NO: 1 that increases tissue tropism of a virus to the kidney, wherein the region of amino acid 561-588 of SEQ ID NO: 1 has a sequence selected from the group consisting of: SEQ ID NO: 3, SEQ ID NO: 4, SEQ ID NO: 5, SEQ ID NO: 6, SEQ ID NO: 7, SEQ ID NO: 8, or SEQ ID NO: 9;

a mutation in the region of amino acids 561-588 of SEQ ID NO: 1 that increases tissue tropism of a virus to the liver, wherein the region of amino acid 561-588 of SEQ ID NO: 1 has a sequence selected from the group consisting of: SEQ ID NO: 10, SEQ ID NO: 11, SEQ ID NO: 12, SEQ ID NO: 13, SEQ ID NO: 14, or SEQ ID NO: 15; or a mutation in the region of amino acids 561-588 of SEQ ID NO: 1 that increases tissue tropism of a virus to the lung, wherein the region of amino acid 561-588 of SEQ ID NO: 1 has a sequence selected from the group consisting of: SEQ ID NO: 16, SEQ ID NO: 17, SEQ ID NO: 18, SEQ ID NO: 19, or SEQ ID NO: 20.

2. The AAV2 capsid polypeptide of claim 1, wherein the AAV2 capsid polypeptide comprises a mutation in the region of amino acids 561-588 of SEQ ID NO: 1 that increases tissue tropism of a virus to the kidney, wherein the region of amino acid 561-588 of SEQ ID NO: 1 has a sequence selected from the group consisting of: SEQ ID NO: 3, SEQ ID NO: 4, SEQ ID NO: 5, SEQ ID NO: 6, SEQ ID NO: 7, SEQ ID NO: 8, or SEQ ID NO: 9.

3. The AAV2 capsid polypeptide of claim 1, wherein the AAV2 capsid polypeptide comprises a mutation in the region of amino acids 561-588 of SEQ ID NO: 1 that increases tissue tropism of a virus to the liver, wherein the region of amino acid 561-588 of SEQ ID NO: 1 has a sequence selected from the group consisting of: SEQ ID NO: 10, SEQ ID NO: 11, SEQ ID NO: 12, SEQ ID NO: 13, SEQ ID NO: 14, or SEQ ID NO: 15.

4. The AAV2 capsid polypeptide of claim 1, wherein the AAV2 capsid polypeptide comprises a mutation in the region of amino acids 561-588 of SEQ ID NO: 1 that increases tissue tropism of a virus to the lung, wherein the region of amino acid 561-588 of SEQ ID NO: 1 has a sequence selected from the group consisting of: SEQ ID NO: 16, SEQ ID NO: 17, SEQ ID NO: 18, SEQ ID NO: 19, or SEQ ID NO: 20.

5. A nucleic acid encoding the AAV2 capsid polypeptide of claim 1.

6. A viral particle comprising the AAV2 capsid polypeptide of claim 1.

7. A viral particle comprising the AAV2 capsid polypeptide of claim 2.

8. A viral particle comprising the AAV2 capsid polypeptide of claim 3.

9. A viral particle comprising the AAV2 capsid polypeptide of claim 4.

10. A method of delivering a heterologous nucleic acid to a cell, the method comprising contacting the cell with a viral particle comprising the heterologous nucleic acid and the AAV2 capsid polypeptide of claim 1.

11. The method of claim 10, wherein the cell is a kidney cell.

12. The method of claim 11, wherein the AAV2 capsid polypeptide comprises a mutation in the region of amino acids 561-588 of SEQ ID NO: 1 that increases tissue tropism of a virus to the kidney, wherein the region of amino acid 561-588 of SEQ ID NO: 1 has a sequence selected from the group consisting of: SEQ ID NO: 3, SEQ ID NO: 4, SEQ ID NO: 5, SEQ ID NO: 6, SEQ ID NO: 7, SEQ ID NO: 8, or SEQ ID NO: 9.

13. The method of claim 10, wherein the cell is a liver cell.

14. The method of claim 13, wherein the AAV2 capsid polypeptide comprises a mutation in the region of amino acids 561-588 of SEQ ID NO: 1 that increases tissue tropism of a virus to the liver, wherein the region of amino acid 561-588 of SEQ ID NO: 1 has a sequence selected from the group consisting of: SEQ ID NO: 10, SEQ ID NO: 11, SEQ ID NO: 12, SEQ ID NO: 13, SEQ ID NO: 14, or SEQ ID NO: 15.

15. The method of claim 10, wherein the cell is a lung cell.

16. The method of claim 15, wherein the AAV2 capsid polypeptide comprises a mutation in the region of amino acids 561-588 of SEQ ID NO: 1 that increases tissue tropism of a virus to the lung, wherein the region of amino acid 561-588 of SEQ ID NO: 1 has a sequence selected from the group consisting of: SEQ ID NO: 16, SEQ ID NO: 17, SEQ ID NO: 18, SEQ ID NO: 19, or SEQ ID NO: 20.

* * * * *